(12) United States Patent
Zhang et al.

(10) Patent No.: US 11,084,790 B2
(45) Date of Patent: Aug. 10, 2021

(54) INSOLUBLE COMPLEX OR SOLVATE THEREOF, PHARMACEUTICAL COMPOSITION AND USE THEREOF

(71) Applicant: Fruithy Holdings Limited, Hong Kong (CN)

(72) Inventors: Shanchun Zhang, Hefei (CN); Yihua Wang, Hefei (CN); Jiashi Peng, Hefei (CN); Kaisheng Cheng, Hefei (CN); Xiao Wang, Hefei (CN); Shu Gao, Hefei (CN); Hongzhang Sun, Hefei (CN); Xiaorong Lu, Hefei (CN)

(73) Assignee: Fruithy Holdings Limited, Hong Kong (CN)

( * ) Notice: Subject to any disclaimer, the term of this patent is extended or adjusted under 35 U.S.C. 154(b) by 8 days.

(21) Appl. No.: 16/325,997

(22) PCT Filed: Mar. 26, 2018

(86) PCT No.: PCT/CN2018/080424
§ 371 (c)(1),
(2) Date: Feb. 15, 2019

(87) PCT Pub. No.: WO2018/177232
PCT Pub. Date: Oct. 4, 2018

(65) Prior Publication Data
US 2021/0087144 A1    Mar. 25, 2021

(30) Foreign Application Priority Data

Mar. 27, 2017 (CN) .......................... 201710188001.7

(51) Int. Cl.
| C07D 211/60 | (2006.01) |
| A61K 47/54 | (2017.01) |
| A61P 23/02 | (2006.01) |
| A61K 9/00 | (2006.01) |
| C07C 65/11 | (2006.01) |

(52) U.S. Cl.
CPC .......... C07D 211/60 (2013.01); A61K 9/0019 (2013.01); A61K 47/542 (2017.08); A61P 23/02 (2018.01); C07C 65/11 (2013.01)

(58) Field of Classification Search
None
See application file for complete search history.

(56) References Cited

U.S. PATENT DOCUMENTS 8,920,843 B2    12/2014    Sawan et al.

FOREIGN PATENT DOCUMENTS

| CN | 104370934 | 2/2015 |
| EP | 2398468 B1 | 11/2016 |
| WO | WO 2004/112713 | 12/2004 |
| WO | WO 2011/057593 A2 | 5/2011 |
| WO | WO 2018/122626 | 7/2018 |

OTHER PUBLICATIONS

AU Examination Report No. 1 for App No. AU2018241564 dated Dec. 16, 2019 (6 pages).
Balbach, S. et al., "Pharmaceutical evaluation of early development candidates: The 100 mg approach", International Journal of Pharmaceutics, 275:1-12 (2004).
Caira M.R., "Crystalline Polymorphsim of Organic Compounds", Design of Organic Solids, Weber E et al, "ED", Springer, 1998 (46 pages).
Singhal, D. et al., "Drug polymorphism and dosage form design: a practical perspective", Advanced Drug Delivery Reviews, 56:335-347 (2004).
Jesper Ostergasrd, et al., "Bupivacaine salts of diflunisal and other aromatic hydroxycarboxylic acids; Aqueous solubility and release characteristics from solutions and suspensions using a rotating dialysis cell model," European Journal of Pharmaceuticals Sciences 26 (2005) 280-287.
Naomi I. Nakano, et al., Dissolution of bupivacaine 3-hydroxy-2-naphthoate into phosphate buffers, J. Pharm. Pharmacol. (1979), 31:622-626.
ISA/CN, International Search Report for PCT/CN2018/080424 (dated Jun. 28, 2018).

(Continued)

*Primary Examiner* — Zinna Northington Davis
(74) *Attorney, Agent, or Firm* — Sterne, Kessler, Goldstein & Fox P.L.L.C.

(57) ABSTRACT

The present invention provides a complex of formula (I) or a solvate thereof (wherein n is 1 to 4), a pharmaceutical composition, and use of the pharmaceutical composition in the prevention or treatment of surgical pain, intraoperative pain and postsurgical pain. The technical solution according to the present invention provides a medicament which can be produced by a simple production process and can stably release a local anesthetic in body for a long period. The medicament can be released for at least three days or more, which can prolong the analgesic effect on the postsurgical pain, can be used conveniently by the physician and the patient, and has a good treatment compliance.

Formula (I)

23 Claims, 16 Drawing Sheets

(56) References Cited

OTHER PUBLICATIONS

Nakano, N., et al., "3-Hydroxy-2-naphthoates of Lidocaine, Mepivacaine, and Bupivacaine and Their Dissolution Characteristics," *Chemical and Pharmaceutical Bulletin*, 26(3): 936-941 (1978).
Written Opinion and Search Report for Singapore Patent Application 11201906132U, dated Nov. 2, 2020, Intellectual Property Office of Singapore, 8 pages.

INSOLUBLE COMPLEX OR SOLVATE THEREOF, PHARMACEUTICAL COMPOSITION AND USE THEREOF

CROSS-REFERENCE TO RELATED APPLICATIONS

This application is a U.S. National Phase application under 35 U.S.C. § 371 of International Patent Application No. PCT/CN2018/080424, filed Mar. 26, 2018, which claims priority to Chinese Application No. 201710188001.7, filed Mar. 27, 2017. The entire contents of the parent applications are hereby incorporated by reference.

TECHNICAL FIELD

The present invention relates to the technical field of medicinal chemistry, and particularly to an insoluble complex or a solvate thereof, a pharmaceutical composition (i.e., a long-acting solid microparticle suspension injection), and medical use of the pharmaceutical composition.

BACKGROUND 1-butyl-N-(2,6-dimethylphenyl)-2-piperidinecarboxamide hydrochloride (also referred to as bupivacaine hydrochloride) is a local anesthetic widely used in surgical local anesthesia and postsurgical analgesia worldwide. It is used in local infiltration anesthesia, peripheral nerve block, and intrathecal block in a form of injection administration.

Postsurgical pain is an instant acute pain after surgery (usually lasting for no more than 7 days), which is an acute nociceptive pain in nature, and it is also the most common acute pain and requires most urgent treatment in clinical practice. If the acute pain is not sufficiently controlled in the original stage, it will easily become a postsurgical chronic pain. Clinically, opioids are commonly used to treat postsurgical pain, but they have adverse effects such as respiratory depression, addiction and the like. Local anesthetics are the most important analgesics, including procaine, lidocaine, tetracaine, bupivacaine, and ropivacaine. However, the effective times of the existing local anesthetic drugs are relatively short (usually lasting for no more than 7 hours). Thus, a constant incision analgesia device is clinically used to instill an amide-based anesthetic at the wound so as to maintain a certain treatment concentration. However, this device still has certain disadvantages. For example, a medicament storage bag must be carried, which is inconvenient for the patient; the placement of a osmotic catheter in body increases the local irritation, and some complications may occur; it is difficult to take out the osmotic catheter after treatment; and so on. Therefore, it becomes a research hotspot to develop a long-acting local anesthetic at present.

In order to achieve the purpose of prolonging the sustained action time of the soluble medicaments such as bupivacaine hydrochloride, the researchers from various countries have attempted to use various technologies. *J. Pharm. Pharmacol.* 1979, 31: 622-626 reported a bupivacaine 3-hydroxyl-2-naphthoate, and the research showed that this insoluble salt exhibited a "separation" phenomena between the acid radical and basic group solubilities in a physiological environment (37° C., pH 7.4, 0.5 M phosphate buffer), where the ratio between the acid radical and the basic group in the solution varied over time. *European Journal of Pharmaceutical Sciences* 26 (2005) 280-287 reported a series of bupivacaine hydroxy aryl carboxylates. A successful example is a bupivacaine liposome suspension for injection developed by using a multilamellar liposome as a carrier material (trade name: Exparel®), which is widely used in the alleviation of postsurgical pains of various types. The injection of a single dose into a surgical site can produce a significant analgesic effect lasting for up to 72 h. However, Exparel® utilizes a complex liposome formulation technology, and the complex production process is its significant disadvantage.

Therefore, there is an urgent need for a medicament which can be produced by a simple production process and can stably release a local anesthetic in body for a long period. The medicament can be released for at least three days or more, which can prolong the analgesic effect on the postsurgical pain, can be used conveniently by the physician and the patient, and has a good treatment compliance.

SUMMARY

The present invention discloses an insoluble complex or a solvate thereof. The present invention further discloses a pharmaceutical composition comprising the complex or the solvate thereof, i.e., a long-acting solid microparticle suspension injection.

The formulation using the insoluble complex or a solvate thereof can release a drug in body sustainably, maintain the drug concentration for 24 hours or more, and achieve an analgesic effect on postsurgical pain lasting for 24 hours or more.

According to one aspect of the invention, the present invention provides a complex of formula (I) or a solvate thereof:

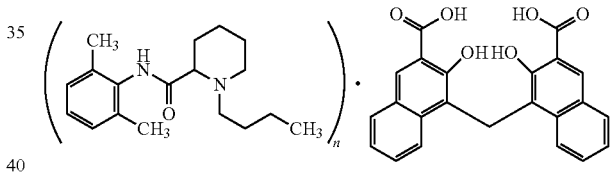

wherein n is 1 to 4.

Preferably, n is 2.

Preferably, the solvate is a methanol solvate, an ethanol solvate, or a hydrate.

Preferably, the complex or the solvate is an ethanol solvate having a polymorph A, wherein an X-ray powder diffraction pattern thereof, measured with Cu—Kα radiation, has diffraction peaks at about 4.9±0.2, 9.8±0.2, and 12.0±0.2 represented by 2θ.

Preferably, the complex or the solvate has a polymorph A, wherein a X-ray powder diffraction thereof, measured with Cu—Kα radiation, has diffraction peaks at about 4.9±0.2, 9.8±0.2, 10.9±0.2, 12.0±0.2, 12.9±0.2, 13.7±0.2, 14.7±0.2, 15.6±0.2, 16.3±0.2, 17.6±0.2, 18.9±0.2, 19.7±0.2, 20.2±0.2, 24.7±0.2, and 26.1±0.2 represented by 2θ.

Preferably, the X-ray powder diffraction pattern of the polymorph A is substantially as shown in FIG. 1.

Preferably, the complex or the solvate thereof is a methanol solvate having a polymorph B, wherein an X-ray powder diffraction pattern thereof, measured with Cu—Kα radiation, has diffraction peaks at about 10.9±0.2, 12.6±0.2, and 13.7±0.2 represented by 2θ.

Preferably, the complex or the solvate has a polymorph B, wherein the X-ray powder diffraction, measured with Cu—Kα radiation, has diffraction peaks at about 10.9±0.2, 12.6±0.2, 13.7±0.2, 14.2±0.2, 15.7±0.2, 16.7±0.2, 17.3±0.2, 18.3±0.2, 18.9±0.2, 19.4±0.2, 25.1±0.2, 26.4±0.2, 29.0±0.2, and 34.6±0.2 represented by 2θ.

Preferably, the X-ray powder diffraction pattern of the polymorph B is substantially as shown in FIG. 2.

Preferably, the complex or the solvate thereof is a hydrate having a polymorph C, wherein an X-ray powder diffraction pattern thereof, measured with Cu—Kα radiation, has diffraction peaks at about 10.8±0.2, 12.6±0.2, and 13.7±0.2 represented by 2θ.

Preferably, the complex or the solvate has a polymorph C, wherein the X-ray powder diffraction, measured with Cu—Kα radiation, has diffraction peaks at about 10.8±0.2, 12.6±0.2, 13.7±0.2, 16.5±0.2, 18.2±0.2, 19.4±0.2, 20.0±0.2, and 27.0±0.2 represented by 2θ.

Preferably, the X-ray powder diffraction pattern of the polymorph C is substantially as shown in FIG. 3.

Preferably, the complex or the solvate thereof is in an amorphous form.

Preferably, the complex or the solvate thereof has a median particle size $D_{50}$ in a range of 0.1 to 50 μm.

According to another aspect of the invention, the present invention provides a method for preparing the complex or the solvate thereof as described above, comprising mixing bupivacaine and pamoic acid in a molar ratio of greater than 1:1 and less than or equal to 4:1 in a solvent and heating the resultant mixture, wherein the solvent is selected from a group consisting of methanol, acetone, ethanol, dimethylsulfoxide, N, N-dimethylformamide, water and a mixed solvent thereof.

Preferably, in the above preparation method, the molar ratio between the bupivacaine and the pamoic acid is greater than or equal to 2:1.

According to yet another aspect of the invention, the present invention provides a method for preparing the polymorph A of the complex or the solvate thereof as described above, comprising mixing bupivacaine and pamoic acid in a molar ratio of greater than or equal to 2:1 in a solvent and heating the resultant mixture, wherein the solvent comprises ethanol and optionally comprises one or more selected from a group consisting of methanol, acetone, dimethylsulfoxide, N,N-dimethylformamide and water.

According to yet another aspect of the invention, the present invention provides a method for preparing the polymorph B of the complex or the solvate thereof as described above, comprising mixing bupivacaine and pamoic acid in a molar ratio of greater than or equal to 2:1 in a solvent and heating the resultant mixture, wherein the solvent comprises methanol and optionally comprises one or more selected from a group consisting of acetone, dimethylsulfoxide, N,N-dimethylformamide and water.

According to yet another aspect of the invention, the present invention provides a method for preparing the polymorph C of the complex or the solvate thereof as described above, comprising converting the polymorph A, the polymorph B or the amorphous form of the complex or the solvate thereof as described above into a bis(bupivacaine) pamoate hydrate in water.

According to yet another aspect of the invention, the present invention provides a method for preparing the amorphous form of the complex as described above, comprising converting the polymorph A, the polymorph B or the polymorph C of the complex or the solvate thereof as described above into amorphous powders by heating it to remove the solvent; or preparing amorphous powders from bupivacaine and pamoic acid by a melting method.

According to yet another aspect of the invention, the present invention provides a pharmaceutical composition comprising a pharmaceutically effective amount of the complex or the solvate thereof as described above and a pharmaceutically acceptable excipient.

Preferably, the pharmaceutically acceptable excipient comprises one or more selected from a group consisting of a suspending agent, a surfactant, a filler, a preservative, an isoosmotic adjusting agent, a pH modifier, a buffer and water.

Preferably, the complex or the solvate thereof is solid particles having a median particle size $D_{50}$ in a range of 0.2 to 20 μm.

Preferably, the pharmaceutical composition is a suspension, and comprises 1 to 300 mg, preferably 5 to 100 mg of the complex or the solvate thereof per 1 mL of the suspension.

Preferably, the pharmaceutical composition contains no water, and comprises 10 wt % or more, preferably 20 wt % or more of the complex or the solvate thereof.

Preferably, the suspending agent is one or more selected from a group consisting of carboxymethyl cellulose or a sodium salt thereof, hydroxypropyl cellulose, methyl cellulose, hydroxyethyl cellulose, hydroxypropyl methylcellulose, sodium hyaluronate, and polyvinylpyrrolidone, preferably one or more of sodium carboxymethyl cellulose and polyvinylpyrrolidone; the surfactant is one or more selected from a group consisting of polysorbate-20 (Tween-20), polysorbate-40 (Tween-40), polysorbate-60 (Tween-60), polysorbate-65 (Tween-65), polysorbate-80 (Tween-80), polysorbate-85 (Tween-85), polyoxyethylated castor oil, polyoxyethylated hydrogenated castor oil, lecithin, polyvinylpyrrolidone, polyethylene glycols, polyethylene oxide and polypropylene oxide ethers (Poloxamer 188, Poloxamer 407, and the like), and polyethylene glycol 15-hydroxystearate, preferably one or more of Tween-20, Tween-80, polyethylene glycol 15-hydroxystearate and Poloxamer 188; the filler is one or more selected from a group consisting of mannitol, sucrose, maltose, xylitol, lactose, glucose, starch, sorbitol and analogs thereof, preferably, one or more of mannitol, lactose and sucrose; the preservative is one or more selected from a group consisting of benzoic acid, benzyl alcohol, butylated hydroxytoluene ether, butylated hydroxytoluene, chlorobutanol, gallate, hydroxybenzoate, ethylenediamine tetraacetic acid and a salt thereof, phenol, chlorocresol, m-cresol, methylbenzethonium chloride, myristyl-γ-methylpyridine chloride, phenylmercuric acetate, and thimerosal, preferably one or more of benzyl alcohol and hydroxybenzoate; the isoosmotic adjusting agent is one or more selected from a group consisting of mannitol, sorbitol, sodium chloride, glucose, sucrose, fructose, and lactose, preferably one or more of mannitol, sodium chloride and glucose; and the buffer is one or more selected from a group consisting of a phosphate, an acetate, a citrate, and a tris(hydroxymethyl)aminomethane buffer solution, preferably a phosphate.

According to one aspect of the invention, the present invention provides use of the pharmaceutical composition described above in the prevention or treatment of surgical pain, intraoperative pain, and postsurgical pain.

Preferably, in the above use, the pharmaceutical composition is administrated via subcutaneous injection, intracutaneous injection, or intramuscular injection.

The technical solution according to the present invention provides a medicament which can be produced by a simple production process and can stably release a local anesthetic in body for a long period. The medicament can be released for at least three days or more, which can prolong the analgesic effect on the postsurgical pain, can be used conveniently by the physician and the patient, and has a good treatment compliance.

BRIEF DESCRIPTION OF THE DRAWINGS

Drawings are provided below to describe embodiments according to the present invention in detail, in which.

DESCRIPTION OF EMBODIMENTS

Figure 1:
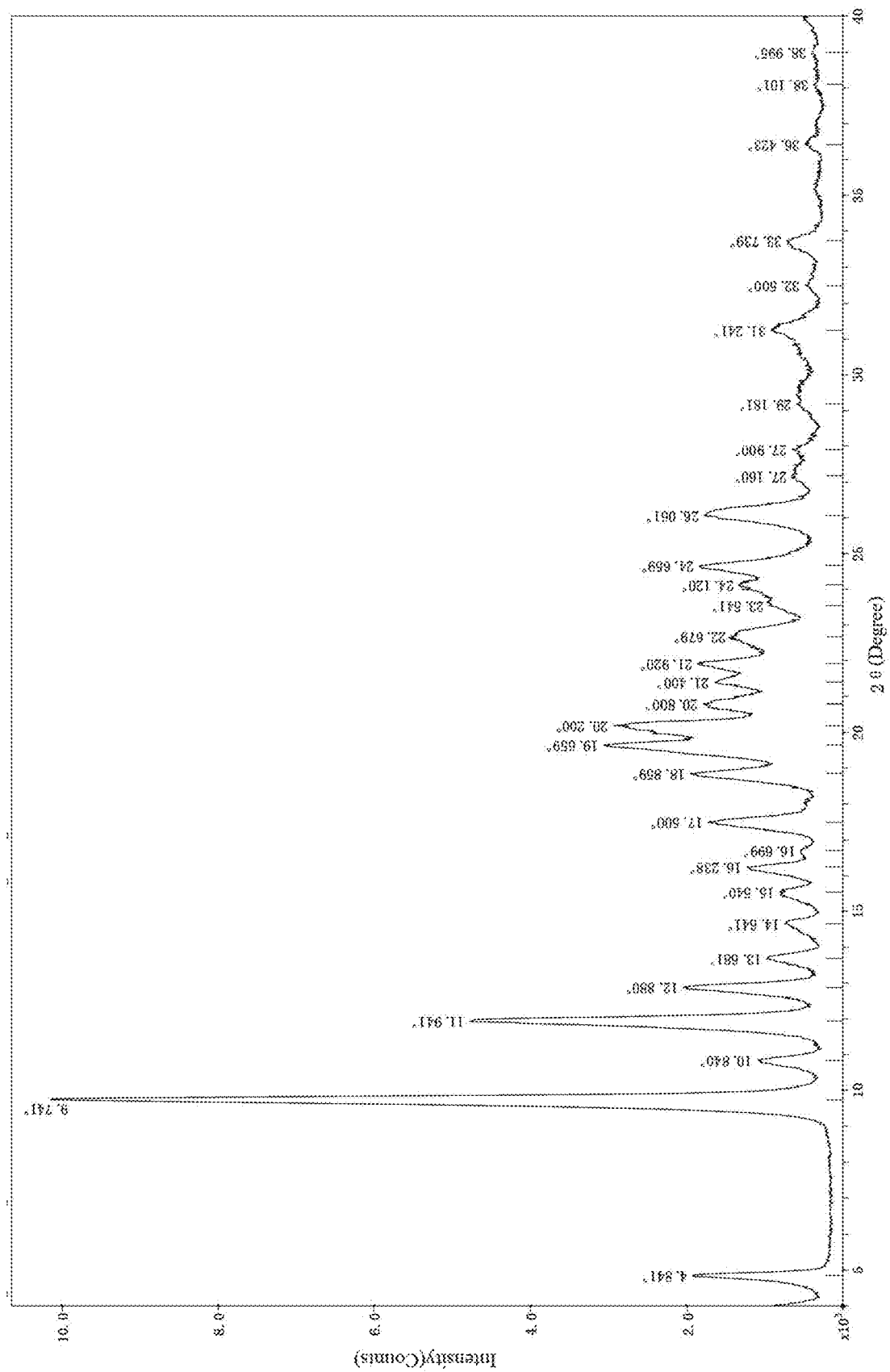
FIG. 1 shows an X-ray diffraction pattern of bis(bupivacaine) pamoate powders (polymorph A).

The present invention will be further described in detail below with reference to particular embodiments. It will be appreciated that other embodiments are contemplated and can be implemented without departing from the scope or spirit of the present invention. Therefore, the following detailed description is non-limiting.

Unless otherwise indicated, all numbers used in the description and claims to represent characteristic dimensions, amounts, and physical and chemical properties should be understood to be modified with the term "about" in all cases. Therefore, unless contradictorily specified, all numerical parameters listed in the above description and the appended claims are approximate values, and those skilled in the art can seek to attain the desired properties by appropriately changing these approximate values from the teaching of the present invention. Use of a numerical range indicated with endpoints includes all numbers and any range in the range. For example, a range of 1 to 5 includes 1, 1.1, 1.3, 1.5, 2, 2.75, 3, 3.80, 4, 5, and so forth.

The insoluble complex of the present invention has a structure and composition according to formula (I).

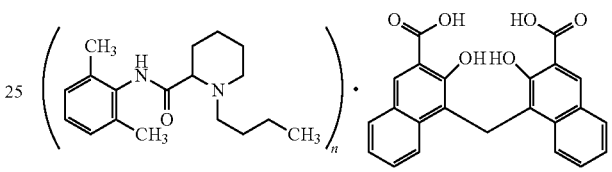

In formula (I), n is 1 to 4.

The complex provided in the present invention is consisted of bupivacaine and pamoic acid in a certain molecular proportion, including 1:1, 2:1, 3:1 and 4:1.

It is known in the art that bupivacaine is a chiral compound having two configurations of levorotatory bupivacaine and dextrorotatory bupivacaine. Particular chiral configurations of bupivacaine are not particularly limited according to the technical solutions of the present invention. That is, a bupivacaine racemate (i.e., a mixture of levorotatory bupivacaine and dextrorotatory bupivacaine in a molar ratio of 1:1) may be used, and either of levorotatory bupivacaine and dextrorotatory bupivacaine or a mixture thereof in any ratio may also be used.

The present invention provides not only a non-solvate of a bupivacaine-pamoic acid complex, but also a solvate thereof, wherein the solvent includes, but not limited to, methanol, ethanol, acetone and water.

The "insoluble" of the present invention means that the solubility thereof (calculated as bupivacaine) in pure water or a 0.01 M phosphate buffered saline at pH 7.4 is less than 0.01 g/mL.

The complex of the present invention refers to a solid bound by a non-covalent action such as ionic bond, hydrogen bond, van de Waals force, π-π packing action and the like, which may be in a salt form or in a co-crystal form. The complex has a property significantly different from that of a single component thereof or a simple mixture with respect to physics, chemistry or mechanics. Reference can be made to Journal of China Pharmaceutical University 2012, 43(5): 475-480, for the definitions of co-crystal and a salt.

The present invention provides bis(bupivacaine) pamoate in a solid state with a stable molecular composition proportion, wherein one molecule of pamoic acid is bound to two molecules of bupivacaine in a stable molecular proportion to form a salt.

Said bis(bupivacaine) pamoate may exist in a solvate form, and the solvent of the solvate is one or more selected from a group consisting of methanol, acetone, ethanol and water. A methanol solvate, an ethanol solvate, or a hydrate is preferable.

The bis(bupivacaine) pamoate or a solvate thereof provided in the present invention appears to be crystalline powders or amorphous powders, which have different X-ray powder diffraction characteristics.

The X-ray powder diffraction pattern, measured with Cu—Kα radiation, of typical crystalline powders of bis(bupivacaine) pamoate provided in the present invention, has diffraction peaks at about 4.9±0.2, 9.8±0.2, 10.9±0.2, 12.0±0.2, 12.9±0.2, 13.7±0.2, 14.7±0.2, 15.6±0.2, 16.3±0.2, 17.6±0.2, 18.9±0.2, 19.7±0.2, 20.2±0.2, 24.7±0.2, and 26.1±0.2 represented by 2θ. The crystalline powders of bis(bupivacaine) pamoate are defined as polymorph A, and the X-ray powder diffraction pattern thereof is substantially as shown in FIG. 1.

Figure 2:
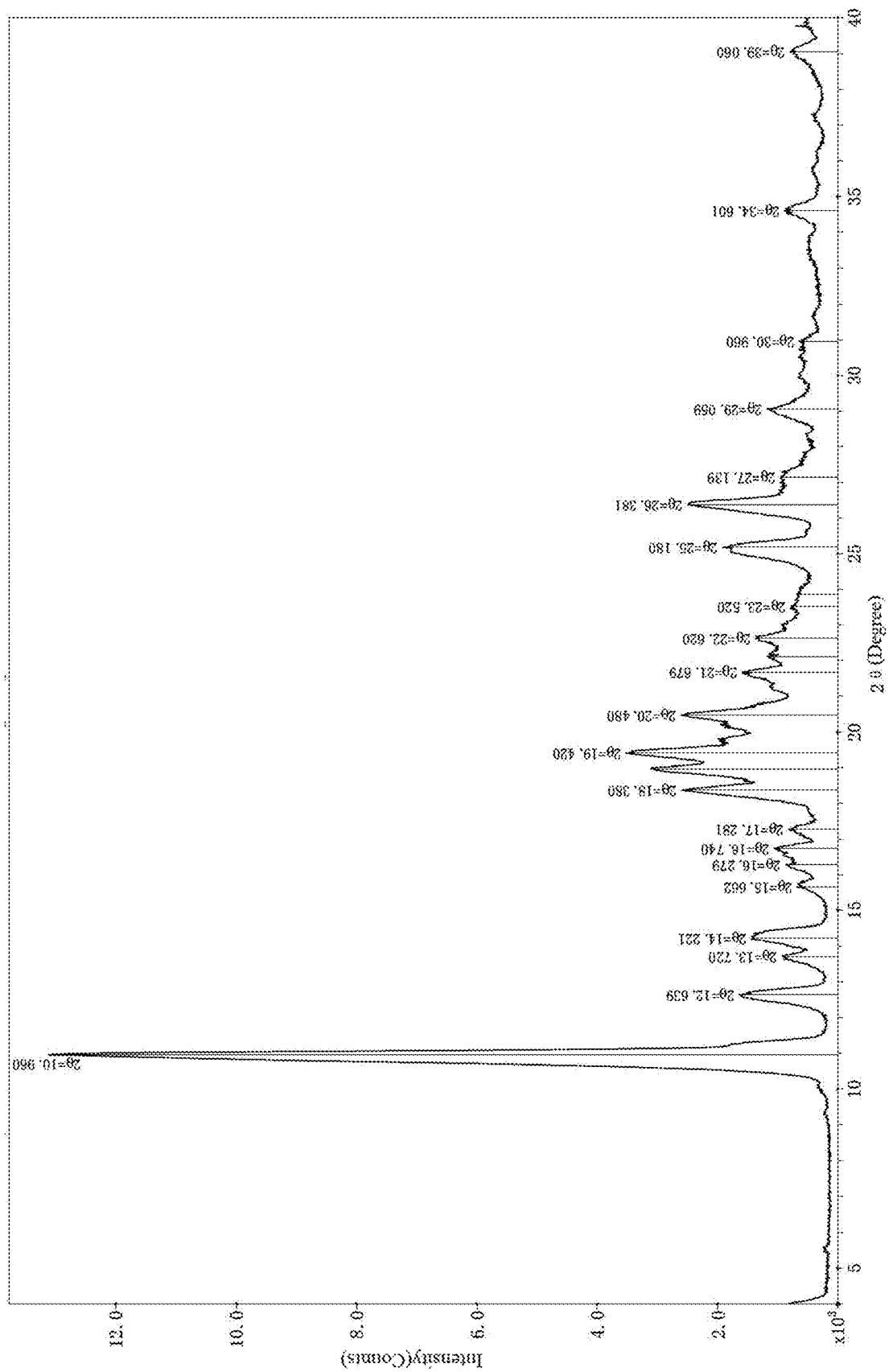
FIG. 2 shows an X-ray diffraction pattern of bis(bupivacaine) pamoate powders (polymorph B).

The X-ray powder diffraction pattern, measured with Cu—Kα radiation, of further crystalline powders of bis(bupivacaine) pamoate provided in the present invention, has diffraction peaks at about 10.9±0.2, 12.6±0.2, 13.7±0.2, 14.2±0.2, 15.7±0.2, 16.7±0.2, 17.3±0.2, 18.3±0.2, 18.9±0.2, 19.4±0.2, 25.1±0.2, 26.4±0.2, 29.0±0.2, and 34.6±0.2 represented by 2θ. The crystalline powders of bis(bupivacaine) pamoate are defined as polymorph B, and the X-ray powder diffraction pattern thereof is substantially as shown in FIG. 2.

Figure 3:
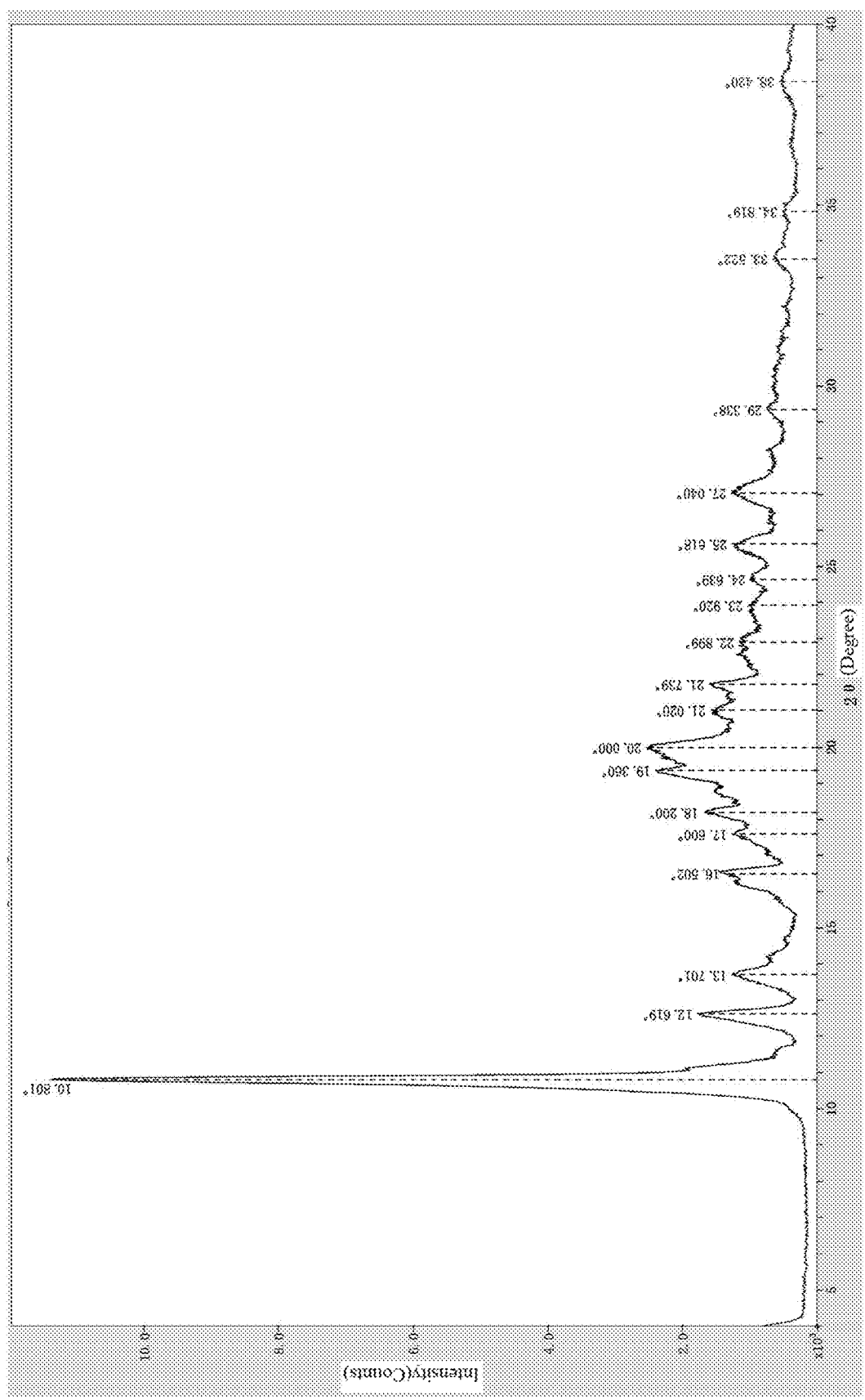
FIG. 3 shows an X-ray diffraction pattern of bis(bupivacaine) pamoate powders (polymorph C).

The present invention also provides further typical crystalline powders of bis(bupivacaine) pamoate, wherein the X-ray powder diffraction, measured with Cu—Kα radiation, has diffraction peaks at about 10.8±0.2, 12.6±0.2, 13.7±0.2, 16.5±0.2, 18.2±0.2, 19.4±0.2, 20.0±0.2, and 27.0±0.2 represented by 2θ. The crystalline powders of bis(bupivacaine) pamoate are defined as polymorph C, and the X-ray powder diffraction pattern thereof is substantially as shown in FIG. 3.

Figure 16:
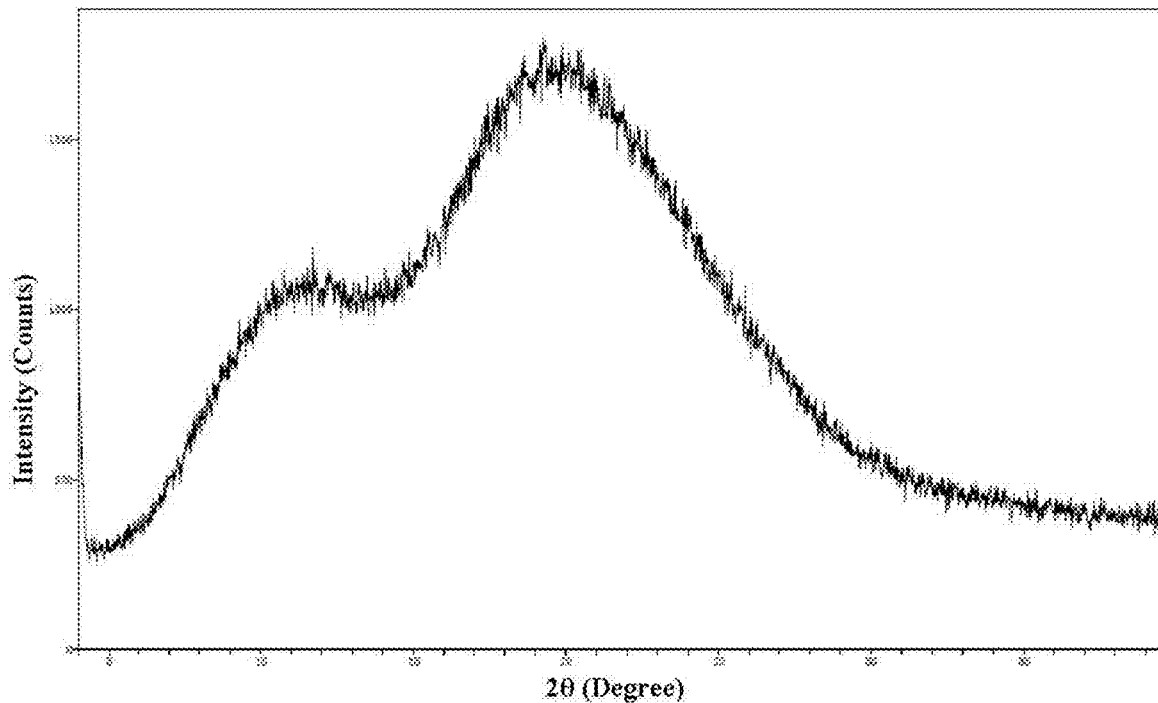
FIG. 16 shows an X-ray powder diffraction pattern of the amorphous bis(bupivacaine) pamoate prepared in Preparation Example 30.

The present invention also provides amorphous powders of bis(bupivacaine) pamoate, and the X-ray powder diffraction pattern thereof is substantially as shown in FIG. 16.

The X-ray powder diffraction patterns of the compounds provided in the present invention are measured with a DX-27mini diffractometer (Dandong Haoyuan Instrument). The measurement parameters are as follows: wavelength=1.5406 angstrom (Cu/κα1); stepping measurement; increment 0.02°; initial angle 4°; terminal angle 40°; scan rate 1.0 second/step; tube voltage 35 KV; and tube current 15 mA.

It is well known by those skilled in the art that an error for the 2θ value diffraction peak position within ±0.2° is acceptable. Further, since there are differences in peak identification in X-ray powder diffraction patterns due to sample preparation, instrument difference and software processing, for example, the amount of peaks may be more or less, polymorphs are considered to be the same if the amount of peaks differ by no more than 20%.

It can be determined by those skilled in the art that a single polymorph or a mixed polymorph comprising crystalline powders in different crystalline states or amorphous form also falls within the present invention.

The embodiments of the present invention provides methods for preparing bis(bupivacaine) pamoate in different solvent systems, wherein 2.0 molar equivalents or more of bupivacaine and pamoic acid are heated in different solvent systems to form a salt, and then the temperature is decreased to crystallize the salt to obtain bis(bupivacaine) pamoate. In order to stably obtain a salt in a molar ratio of 2:1, it is generally required to form a salt with 2.0 molar ratio or more of bupivacaine free base and 1 molar ratio of pamoic acid in the solvent system. The 2:1 salt formed is precipitated out from the solvent in a solid form, and the excess bupivacaine free base and a portion of the 2:1 salt remain in the solvent.

The present invention provides methods for preparing different crystalline powders from the solvent systems such as methanol/acetone, anhydrous methanol, methanol/water, ethanol, ethanol/dimethylsulfoxide, ethanol/dimethylsulfoxide/water, water and the like.

In the present invention, it is preferable to prepare crystalline powders from a system of ethanol, ethanol/dimethylsulfoxide, methanol/acetone, methanol/water, methanol, or water. The range for the particle diameter of the solid powders, expressed as median particle diameter $D_{50}$, is 0.1 to 50 μm, preferably 1 μm to 50 μm, and more preferably 1 μm to 20 μm.

In the present invention, it is preferable to prepare crystalline powders from a system of ethanol, ethanol/dimethylsulfoxide, methanol/acetone, methanol/water, methanol, or water.

In addition to the methods for preparing bis(bupivacaine) pamoate with a solvent crystallization process, the present invention provides other methods for preparing a solid salt or a co-crystal well known by those skilled in the art, including, but not limited to, the methods for preparing a bupivacaine pamoate salt or a co-crystal thereof with a good solvent-poor solvent crystallization process, a spray drying process, a film evaporation process, and a solvent-free melting process, as well as a preparation method by hot melt extrusion.

The present invention also provides a preparation method for converting crystalline powders containing an organic solvent solvate of bis(bupivacaine) pamoate into a hydrate of bis(bupivacaine) pamoate without any organic solvent remained, wherein the organic solvent refers to one or more of methanol, ethanol, isopropanol, n-butanol, acetonitrile, diethyl ether, acetone, tetrahydrofuran, dichloromethane, dioxane, ethyl acetate, methyl t-butyl ether, toluene, n-hexane, petroleum ether, N,N-dimethylformamide, N,N-dimethylacetamide, N-methylpyrrolidone, pyridine, and dimethylsulfoxide.

A simple physical mixture of bupivacaine and pamoic acid appears to have two endothermic peaks in Differential Thermal Analysis (DTA), which are consistent with the endothermic peak of a single component of bupivacaine or pamoic acid respectively. The complex provided in the present invention has an endothermic peak which is not consistent with the endothermic peak of a single component of bupivacaine or pamoic acid, or has no obvious endothermic peak.

The polymorph A, polymorph B, polymorph C and amorphous form of bis(bupivacaine) pamoate provided in the present invention have different endothermic characteristics and solvates, appearing to have different endothermic peaks in Differential Thermal Analysis (DTA). In general, the polymorph A and the polymorph C each have a single endothermic peak, the polymorph B has two peaks, and the amorphous form has no obvious endothermic peak.

For comparison research, the embodiments of the present invention also provide a method for preparing a bupivacaine-pamoic acid salt (1:1 salt) and a method for preparing an insoluble salt formed from bupivacaine with other acids, including dibenzoyl tartaric acid, di-p-toluoyl tartaric acid, (R)-1,1'-Binaphthyl-2,2'-diyl hydrogenphosphate, D-camphorsulfonic acid and the like. The present invention also provides a method for preparing an insoluble salt formed from ropivacaine with different acids. These insoluble salts include a salt of basic group and acid radical in a molar ratio of 1:1 and a salt of basic group and acid radical in a molar ratio of 2:1.

The present invention provides a method for determining the solubility of the insoluble salt in a simulated body fluid and data for the ratio of acid radical and basic group in the suspension to illustrate the solubility and stability of the insoluble salt in the suspension. Most of the insoluble salts provided in the present invention have a low solubility, but the solubility of most insoluble salts is higher than that of bupivacaine free base or ropivacaine free base under the same condition. The suspensions of some insoluble salts are not stable, and the ratio of acid radical and basic group will vary over time.

It can be known by those skilled in the art that a lower solubility can enable a longer drug dissolution time in order to achieve the purpose of sustained release of a drug.

The bis(bupivacaine) pamoate provided in the present invention has unexpected effects. It has a very low solubility (a saturated solubility of 0.3 mM in 0.01 M PBS at pH 7.4), and can be stably present in a simulated body fluid medium. The ratio of acid radical and basic group in the solution remains stable (a ratio of 2:1). The bis(bupivacaine) pamoate is suitable to be formulated into a solid suspension injection for use.

The present invention provides a pharmaceutical composition comprising bis(bupivacaine) pamoate. It contains bis(bupivacaine) pamoate and a pharmaceutically acceptable excipient, and releases the drug for at least 12 hours, preferably for at least 24 hours, and more preferably for at least 72 hours.

The pharmaceutical composition may be a solid, an aqueous suspension, or a solid obtained by drying the suspension with a suitable process. The suitable drying process includes a lyophilization process, a spray drying process or other drying process.

The pharmaceutical composition is preferably an injectable composition, and may be an injection. Such an injection can be used in a manner of subcutaneous injection, intracutaneous injection, or intramuscular injection, and can locally and slowly release bupivacaine to exert a long-term analgesic effect.

The present invention provides that the active ingredient of the bis(bupivacaine) pamoate injection exists in a physical form of a solid microparticle suspension, which may be prepared from any crystalline powders of bis(bupivacaine) pamoate.

The solid microparticles in the bis(bupivacaine) pamoate injection provided in the present invention have a particle size (expressed as median particle size ($D_{50}$)) in a range of 0.2 μm to 50 μm, and preferably 1 μm to 20 μm.

The bis(bupivacaine) pamoate provided in the present invention can cooperate with a suitable solvent and an additive commonly used in the injection to be formulated into corresponding compositions for subcutaneous or intramuscular injection. The pharmaceutically acceptable excipient is one or more of the following: (1) a suspending agent, (2) a surfactant, (3) a filler, (4) a preservative, (5) an isoosmotic adjusting agent, (7) a buffer, and (8) water. The suspending agent is one or more selected from a group consisting of carboxymethyl cellulose or a sodium salt thereof, hydroxypropyl cellulose, methyl cellulose, hydroxyethyl cellulose, hydroxypropyl methylcellulose, sodium hyaluronate, and polyvinylpyrrolidone, preferably one or more of sodium carboxymethyl cellulose and polyvinylpyrrolidone; the surfactant is one or more selected from a group consisting of polysorbate-20 (Tween-20), polysorbate-40 (Tween-40), polysorbate-60 (Tween-60), polysorbate-65 (Tween-65), polysorbate-80 (Tween-80), polysorbate-85 (Tween-85), polyoxyethylated castor oil, polyoxyethylated hydrogenated castor oil, lecithin, polyvinylpyrrolidone, polyethylene glycols, polyethylene oxide and polypropylene oxide ethers (Poloxamer 188, Poloxamer 407, and the like), and polyethylene glycol 15-hydroxystearate, preferably one or more of Tween-20, Tween-80, polyethylene glycol 15-hydroxystearate and Poloxamer 188; the filler is one or more selected from a group consisting of mannitol, sucrose, maltose, xylitol, lactose, glucose, starch, sorbitol and analogs thereof, preferably, mannitol, lactose and sucrose; the preservative is one or more selected from a group consisting of benzoic acid, benzyl alcohol, butylated hydroxytoluene ether, butylated hydroxytoluene, chlorobutanol, gallate, hydroxybenzoate, ethylenediamine tetraacetic acid (EDTA) and a salt thereof, phenol, chlorocresol, m-cresol, methylbenzethonium chloride, myristyl-γ-methylpyridine chloride, phenylmercuric acetate, and thimerosal, preferably one or more of benzyl alcohol and hydroxybenzoate; the isoosmotic adjusting agent is one or more selected from a group consisting of mannitol, sorbitol, sodium chloride, glucose, sucrose, fructose, and lactose, preferably one or more of mannitol, sodium chloride and glucose; and the buffer is one or more selected from a group consisting of a phosphate, an acetate, a citrate, and a tris(hydroxymethyl) aminomethane (TRIS) buffer solution, preferably a phosphate.

The injection composition provided in the present invention contains 1 to 300 mg, and preferably 5 to 100 mg of bis(bupivacaine) pamoate per 1 mL suspension, based on the total volume of the aqueous composition; or contains not less than 10 wt %, and preferably not less than 20 wt % of bis(bupivacaine) pamoate, wherein the weight percentage of each component is calculated based on the total weight of the composition containing no water.

The present invention also provides a test on the dissolution of the bis(bupivacaine) pamoate injection and the results thereof, indicating the features of stable dissolution and drug sustained release thereof.

The injection composition provided in the present invention has an analgesic effect lasting for not less than 12 hours, preferably not less than 24 hours, and more preferably not less than 72 hours.

One preferred embodiment of the present invention provides the in vivo pharmacokinetic test and the results thereof, indicating that the complex of the present invention has a long-acting release feature exceeding 72 hours.

Therefore, the present invention also provides use of bis(bupivacaine) pamoate and an injection thereof in the prevention or treatment of surgical pain, intraoperative pain, and postsurgical pain, preferably, postsurgical pain. The typical postsurgical pain includes, but not limited to, postsurgical pains after surgical operations such as hemorrhoidectomy, colectomy, cyst resection and the like.

EXAMPLES

The examples provided below facilitate the understanding of the present invention, but not intended to limit the present invention.

All drugs or reagents used in the present invention are conventional commercial products, unless specifically indicated.

In the present invention, all conditions for High Performance Liquid Chromatography related to bupivacaine are as follows, unless specifically indicated.

The conditions for High Performance Liquid Chromatography:

HPLC-a: Stationary phase: octadecylsilyl silica gel, 250× 4.6 mm, 5 μm; mobile phase A: methanol, mobile phase B: 0.1% trifluoroacetic acid, eluting gradient: as follows, flow rate: 1.0 mL/min, column temperature: 35° C., and UV detection wavelength: 216 nm.

| Time/min | Mobile phase A (%) | Mobile phase B (%) |
|---|---|---|
| 0.01 | 55 | 45 |
| 10 | 55 | 45 |
| 14 | 90 | 10 |
| 23 | 90 | 10 |
| 30 | 55 | 45 |
| 35 | 55 | 45 |
| 36 | Stop | |

HPLC-b: Stationary phase: octadecylsilyl silica gel, 250× 4.6 mm, 5 μm; mobile phase: a 10 mmol/L phosphate buffered solution at pH 2.5-acetonitrile (50:50), isocratic elution, flow rate: 1.0 mL/min, column temperature: 40° C., and detection wavelength: 216 nm.

Preparation Example 1. Preparation of Mono(Bupivacaine) Dibenzoyl Tartarate

Bupivacaine (1 g, 3.47 mmol) and dibenzolyl tartaric acid (DBTA, 1.3 g, 3.64 mmol) were weighed and added into ethyl acetate (30 mL). The reaction mixture was stirred and heated to become clear gradually. The reaction mixture was heated and stirred for another 2 hours after a solid was precipitated, then cooled, and filtered. The filter cake was washed with ethyl acetate twice, and dried in vacuum at 60° C. for about 8 hours, to obtain 2.2 g of a white solid, i.e., mono(bupivacaine) dibenzoyl tartarate, with a yield of 95%. It was analyzed and identified through High Performance Liquid Chromatography (HPLC-a) and Nuclear Magnetic Resonance (NMR) that the molar ratio of bupivacaine to dibenzolyl tartaric acid was 1:1.

Endothermic Peak: 161.2° C. (Differential Thermal Analysis, SHIMADZU DTG-60A, temperature increasing rate: 10° C./min).

$^1$H-NMR (DMSO-d6, 300M, BRUKER AV-300): δ (ppm) 9.81(br, 1H, NH), 7.95 (d, 4H, PhCO), 7.67 (m, 2H, PhCO), 7.53 (t, 4H, PhCO), 7.10 (m, 3H, MePh), 5.73 (s, 2H, CHOBz), 3.60 (m, 1H), 3.35 (m, 1H), 2.6~3.0 (m, 3H), 2.14 (s, 6H, CH$_3$), 2.05 (m, 1H), 1.3~1.8 (m, 7H), 1.27 (m, 2H, Et), 0.88 (t, 3H, Et).

Preparation Example 2. Preparation of Bis(Bupivacaine) Dibenzoyl Tartarate

Bupivacaine (2 g, 6.98 mmol) and dibenzoyl tartaric acid (1 g, 2.79 mmol) were dissolved in 20 mL acetone. The reaction mixture was heated to clear, slowly cooled to room temperature, then subjected to crystallization for 1 h, and filtered. The filter cake was dried in vacuum at 50° C. to obtain 1.1 g of a solid, i.e., bis(bupivacaine) dibenzoyl tartarate, with a yield of 42%. It was analyzed and identified through High Performance Liquid Chromatography (HPLC-a) and Nuclear Magnetic Resonance (NMR) that the molar ratio of bupivacaine to dibenzolyl tartaric acid was 2:1.

Endothermic Peak: 110.1° C. (Differential Thermal Analysis, SHIMADZU DTG-60A, temperature increasing rate: 10° C./min).

$^1$H-NMR (DMSO-d6, 300M, BRUKER AV-300): δ (ppm) 7.94 (d, 4H, PhCO), 7.64 (m, 2H, PhCO), 7.53 (t, 4H, PhCO), 7.09 (m, 6H, MePh), 5.68 (s, 2H, CHOBz), 3.25-3.52 (m, 8H), 2.78 (m, 2H), 2.14 (s, 12H, CH$_3$), 1.8~2.05 (m, 2H), 1.3~1.8 (m, 14H), 1.29 (m, 4H, Et), 0.89 (t, 6H, Et).

Preparation Example 3. Preparation of Mono(Bupivacaine) Di-p-Toluoyl Tartarate

Bupivacaine (1 g, 3.47 mmol) and di-p-toluoyl tartaric acid (DTTA, 1.34 g, 3.47 mmol) were dissolved in 14 mL ethyl acetate. The reaction mixture was heated to reflux to become turbid gradually, slowly cooled to room temperature, then subjected to crystallization for 1 h, and filtered. The filter cake was dried in vacuum at 50° C. to obtain 1.3 g of a white solid, i.e., mono(bupivacaine) di-p-toluoyl tartarate, with a yield of 55.6%. It was analyzed and identified through High Performance Liquid Chromatography (HPLC-a) and Nuclear Magnetic Resonance (NMR) that the molar ratio of bupivacaine to di-p-toluoyl tartaric acid was 1:1.

Endothermic Peak: 161.1° C. (Differential Thermal Analysis, SHIMADZU DTG-60A, temperature increasing rate: 10° C./min).

$^1$H-NMR (DMSO-d6, 300M, BRUKER AV-300): δ (ppm) 9.87 (br, 1H, NH), 7.85 (d, 4H, PhCO), 7.34 (t, 4H, PhCO), 7.10 (m, 3H, MePh), 5.69 (s, 2H, CHOBz), 3.66 (m, 1H), 3.37 (m, 1H), 2.6~3.0 (m, 3H), 2.38 (s, 6H, Tol), 2.14 (s, 6H, CH$_3$), 2.05 (m, 1H), 1.3~1.8 (m, 7H), 1.27 (m, 2H, Et), 0.88 (t, 3H, Et).

Preparation Example 4. Preparation of Bis(Bupivacaine) Di-p-Toluoyl Tartarate

Bupivacaine (2.5 g, 8.67 mmol) and di-p-toluoyl tartaric acid (1.34 g, 3.47 mmol) were dissolved in 20 mL ethyl acetate. The reaction mixture was heated to reflux to become turbid gradually, heated and refluxed for another 20 min to precipitate a large amount of solid, then slowly cooled to room temperature, and filtered. The filter cake was dried in vacuum at 50° C. to obtain 2.2 g of a white solid, i.e., bis(bupivacaine) di-p-toluoyl tartarate, with a yield of 65.8%. It was analyzed and identified through High Performance Liquid Chromatography (HPLC-a) and Nuclear Magnetic Resonance (NMR) that the molar ratio of bupivacaine to di-p-toluoyl tartaric acid was 2:1.

Endothermic Peak: 160.9° C. (Differential Thermal Analysis, SHIMADZU DTG-60A, temperature increasing rate: 10° C./min).

$^1$H-NMR (DMSO-d6, 300M, BRUKER AV-300): δ (ppm) 9.83 (br, 2H, NH), 7.86 (d, 4H, PhCO), 7.35 (t, 4H, PhCO), 7.08 (m, 6H, MePh), 5.69 (s, 2H, CHOBz), 3.64 (m, 2H), 3.39 (m, 2H), 2.65~2.95 (m, 6H), 2.37 (s, 6H, Tol), 2.14 (s, 12H, CH$_3$), 1.95~2.05 (m, 2H), 1.3~1.8 (m, 14H), 1.28 (m, 4H, Et), 0.86 (t, 6H, Et).

Preparation Example 5. Preparation of Mono(Ropivacaine) Di-p-Toluoyl Tartarate

Ropivacaine (823 mg, 3 mmol) and di-p-toluoyl tartaric acid (1.22 g, 3 mmol) were dissolved in 20 mL acetone. The reaction mixture was heated to reflux to become turbid gradually, slowly cooled to room temperature, then placed in an ice water bath for crystallization for 1 h, and filtered. The filter cake was dried in vacuum at 50° C. to obtain 1.7 g of a white solid, i.e., mono(ropivacaine) di-p-toluoyl tartarate, with a yield of 83.3%. It was analyzed and identified through High Performance Liquid Chromatography (HPLC-a) and Nuclear Magnetic Resonance (NMR) that the molar ratio of ropivacaine to di-p-toluoyl tartaric acid was 1:1.

Endothermic Peak: 174.7° C. (decomposed at the same time, Differential Thermal Analysis, SHIMADZU DTG-60A, temperature increasing rate: 10° C./min).

$^1$H-NMR (DMSO-d6, 300M, BRUKER AV-300): δ (ppm) 9.88 (br, 1H, NH), 7.85 (d, 4H, PhCO), 7.33 (t, 4H, PhCO), 7.10 (m, 3H, MePh), 5.69 (s, 2H, CHOBz), 3.67 (m, 1H), 3.36 (m, 1H), 2.6~2.9 (m, 3H), 2.37 (s, 6H, Tol), 2.13 (s, 6H, CH$_3$), 2.08 (m, 1H), 1.4~1.9 (m, 7H), 0.88 (t, 3H, Et).

Preparation Example 6. Preparation of Bis(Ropivacaine) Di-p-Toluoyl Tartarate

Ropivacaine (1.375 g, 5 mmol) and di-p-toluoyl tartaric acid (773 mg, 2 mmol) were dissolved in 10 mL acetone, and heated to be dissolved to clear. The reaction mixture was slowly cooled to room temperature, then stirred overnight, and filtered. The filter cake was dried in vacuum at 50° C. to obtain 500 mg of a white solid, i.e., bis(ropivacaine) di-p-toluoyl tartarate, with a yield of 26.7%. It was analyzed and identified through High Performance Liquid Chromatography (HPLC-a) and Nuclear Magnetic Resonance (NMR) that the molar ratio of ropivacaine to di-p-toluoyl tartaric acid was 2:1.

Endothermic Peak: 147.4° C. and 162.1° C. (decomposed at the same time, Differential Thermal Analysis, SHIMADZU DTG-60A, temperature increasing rate: 10° C./min).

$^1$H-NMR (DMSO-d6, 300M, BRUKER AV-300): δ (ppm) 9.78 (br, 2H, NH), 7.85 (d, 4H, PhCO), 7.32 (t, 4H, PhCO), 7.07 (m, 6H, MePh), 5.66 (s, 2H, CHOBz), 3.51 (m, 2H), 3.30 (m, 2H), 2.60~2.79 (m, 6H), 2.37 (s, 6H, Tol), 2.12 (s, 12H, CH$_3$), 1.95~2.05 (m, 2H), 1.3~1.8 (m, 14H), 0.83 (t, 6H, Et).

Preparation Example 7. Preparation of Bupivacaine Binaphthol Phosphate

Bupivacaine (290 mg, 1 mmol) and binaphthol phosphate (1,1'-binaphthyl-2,2'-diyl hydrogenphosphate, 350 mg, 1 mmol) were dissolved in 15 mL methanol, and heated to be dissolved to clear. The reaction mixture was slowly cooled to room temperature, placed in an ice water bath for crystallization for 1 h, and filtered. The filter cake was dried in vacuum at 50° C. to obtain 320 mg of a solid, i.e., bupivacaine binaphthol phosphate, with a yield of 50%. It was analyzed and identified through High Performance Liquid Chromatography (HPLC-a) and Nuclear Magnetic Resonance (NMR) that the molar ratio of bupivacaine to binaphthol phosphate was 1:1.

Endothermic Peak: 280.0° C. (decomposed at the same time, Differential Thermal Analysis, SHIMADZU DTG-60A, temperature increasing rate: 10° C./min).

$^1$H-NMR (DMSO-d6, 300M, BRUKER AV-300): δ (ppm) 10.42 (s, 1H), 9.70 (br, 1H, NH), 8.04 (m, 4H), 7.41 (m, 4H), 7.31 (m, 2H), 7.20 (m, 2H), 7.13 (m, 3H, MePh), 4.05 (m, 1H), 3.38 (m, 1H), 2.9-3.1 (m, 3H), 2.20 (m, 1H), 2.14 (s, 6H, CH$_3$), 1.3~1.8 (m, 7H), 1.28 (m, 2H, Et), 0.86 (t, 3H, Et).

Preparation Example 8. Preparation of Bupivacaine Camphorsulfonate

Bupivacaine (1 g, 3.46 mmol) and D-camphorsulfonic acid (850 mg, 3.66 mmol) were dissolved in 30 mL acetone, and heated to be dissolved to clear. The reaction mixture was slowly cooled to room temperature, placed in an ice water bath for crystallization for 1 h, and filtered. The filter cake was dried in vacuum at 60° C. to obtain 760 mg of a solid, i.e., bupivacaine camphorsulfonate, with a yield of 41%. It was analyzed and identified through Nuclear Magnetic Resonance (NMR) that the molar ratio of bupivacaine to camphorsulfonic acid was 1:1.

Endothermic Peak: 224.8° C. (Differential Thermal Analysis, SHIMADZU DTG-60A, temperature increasing rate: 10° C./min).

$^1$H-NMR (DMSO-d6, 300M, BRUKER AV-300): δ (ppm) 10.2 (s, 1H), 9.70 (s, 1H), 7.14 (m, 3H, MePh), 4.16 (m, 1H), 3.55 (m, 1H), 2.9-3.25 (m, 3H), 2.9 (d, 1H), 2.68 (m, 1H), 2.40 (d, 1H), 2.20~2.30 (m, 2H), 2.16 (s, 3H), 1.5~2.0 (m, 8H), 1.1-1.4 (m, 4H), 1.04 (s, 3H), 0.88 (t, 3H), 0.74 (s, 3H).

Preparation Example 9. Preparation of Mono(Ropivacaine) Pamoate

Ropivacaine (3.02 g, 11 mmol) and pamoic acid (1.94 g, 5 mmol) were added into a mixed solvent of 30 mL methanol and 6 mL acetone, heated to clear, then distilled at normal pressure, and supplemented with 100 mL ethyl acetate gradually. About 50 mL solvent was remained, and a large amount of solid was precipitated. The reaction mixture was filtered. The filter cake was rinsed with ethyl acetate and dried in vacuum at 50° C. to obtain 2.7 g of a solid, i.e., mono(ropivacaine) pamoate, with a yield of 40.9%. It was analyzed and identified through High Performance Liquid Chromatography (HPLC-a) and Nuclear Magnetic Resonance (NMR) that the molar ratio of ropivacaine to pamoic acid was 1:1.

Endothermic Peak: 247.7° C. (decomposed at the same time, Differential Thermal Analysis, SHIMADZU DTG-60A, temperature increasing rate: 10° C./min).

$^1$H-NMR (DMSO-d6, 300M, BRUKER AV-300): δ (ppm) 10.23 (s, 1H, NH), 8.34 (s, 2H), 8.17 (d, 2H), 7.78 (d, 2H), 7.26 (m, 2H), 7.12 (m, 5H), 4.75 (s, 2H), 4.10 (m, 1H), 3.53 (m, 1H), 2.9~3.1 (m, 3H), 2.26 (m, 1H), 2.17 (s, 6H, Me), 1.4~1.9 (m, 7H), 0.91 (t, 3H, Et).

X-ray powder diffraction characteristic peak (wavelength=1.5406 angstrom, Cu/κα1):

| 2θ (°) | d (angstrom) |
| --- | --- |
| 7.08 | 12.475 |
| 8.22 | 10.747 |
| 10.24 | 8.632 |
| 10.76 | 8.215 |
| 12.42 | 7.1200 |
| 13.20 | 6.702 |
| 14.42 | 6.137 |
| 15.14 | 5.847 |
| 15.66 | 5.654 |
| 16.20 | 5.467 |
| 16.92 | 5.236 |
| 19.36 | 4.581 |
| 20.66 | 4.296 |
| 21.56 | 4.118 |
| 23.58 | 3.770 |
| 24.66 | 3.607 |
| 26.52 | 3.358 |

Preparation Example 10. Preparation of Mono(Bupivacaine) Pamoate

Bupivacaine (262 g, 0.91 mol) and pamoic acid (160 g, 0.41 mol) were added into a mixed solvent of 2 L methanol and 2 L acetone, heated to clear and refluxed for 2 h, then distilled at normal pressure, and supplemented with 4 L ethyl acetate gradually. About 2 L solvent was remained, and a large amount of solid was precipitated. The reaction mixture was filtered. The filter cake was rinsed with ethyl acetate and dried in vacuum at 60° C. to obtain 250 g of a light yellow solid, i.e., mono(bupivacaine) pamoate, with a yield of 90%. It was analyzed and identified through High Performance Liquid Chromatography (HPLC-a) and Nuclear Magnetic Resonance (NMR) that the molar ratio of bupivacaine to pamoic acid was 1:1.

Endothermic Peak: 256.7° C. (decomposed at the same time, Differential Thermal Analysis, SHIMADZU DTG-60A, temperature increasing rate: 10° C./min).

$^1$H-NMR (DMSO-d6, 300M, BRUKER AV-300): δ (ppm) 10.42 (s, 1H, NH), 8.37 (s, 2H), 8.19 (d, 2H), 7.79 (d, 2H), 7.27 (m, 2H), 7.13 (m, 5H), 4.77 (s, 2H), 4.21 (m, 1H), 3.51 (m, 1H), 3.07 (m, 3H), 2.30 (m, 1H), 2.17 (s, 6H, Me), 1.4~1.9 (m, 7H), 1.29 (m, 2H, Et), 0.91 (t, 3H, Et).

X-ray powder diffraction characteristic peak (wavelength=1.5406 angstrom, Cu/κα1):

| 2θ (°) | d (angstrom) |
|---|---|
| 7.04 | 12.549 |
| 8.14 | 10.854 |
| 10.22 | 8.649 |
| 10.68 | 8.277 |
| 14.18 | 6.241 |
| 15.08 | 5.871 |
| 15.38 | 5.757 |
| 16.00 | 5.535 |
| 16.40 | 5.401 |
| 20.60 | 4.308 |
| 21.44 | 4.141 |
| 23.68 | 3.754 |
| 24.40 | 3.645 |

Preparation Example 11. Preparation of Bis(Bupivacaine) Pamoate

Bupivacaine (7.21 g, 0.025 mol) and pamoic acid (3.88 g, 0.01 mol) were added into a mixed solvent of 50 mL methanol and 50 mL acetone, and heated to obtain a clear solution (about 100 mL, a small portion of which was used for single crystal cultivation). About 98 mL thereof was slowly cooled and left standing for 2 days for crystallization, and filtered. The filter cake was rinsed with a little amount of a mixed solvent of methanol/acetone (1:1, V/V), and then dried in vacuum at 60° C., to obtain 3.82 g of a light yellow crystalline solid, i.e., bis(bupivacaine) pamoate, with a yield of 39.6%. It was analyzed and identified through High Performance Liquid Chromatography (HPLC-a) and Nuclear Magnetic Resonance (NMR) that the molar ratio of bupivacaine to pamoic acid was 2:1.

Endothermic Peak: 117.2° C. and 145.4° C. (Differential Thermal Analysis, SHIMADZU DTG-60A, temperature increasing rate: 10° C./min).

$^1$H-NMR (DMSO-d6, 300M, BRUKER AV-300): δ (ppm) 10.36 (s, 2H, NH), 8.22 (m, 4H), 7.68 (d, 2H), 7.15 (m, 8H), 7.06 (m, 2H), 4.71 (s, 2H), 4.11 (m, 2H), 3.50 (m, 2H), 3.01 (m, 6H), 2.25 (m, 2H), 2.18 (s, 12H, Me), 1.4~1.9 (m, 14H), 1.30 (m, 4H, Et), 0.89 (t, 6H, Et).

Figure 4:
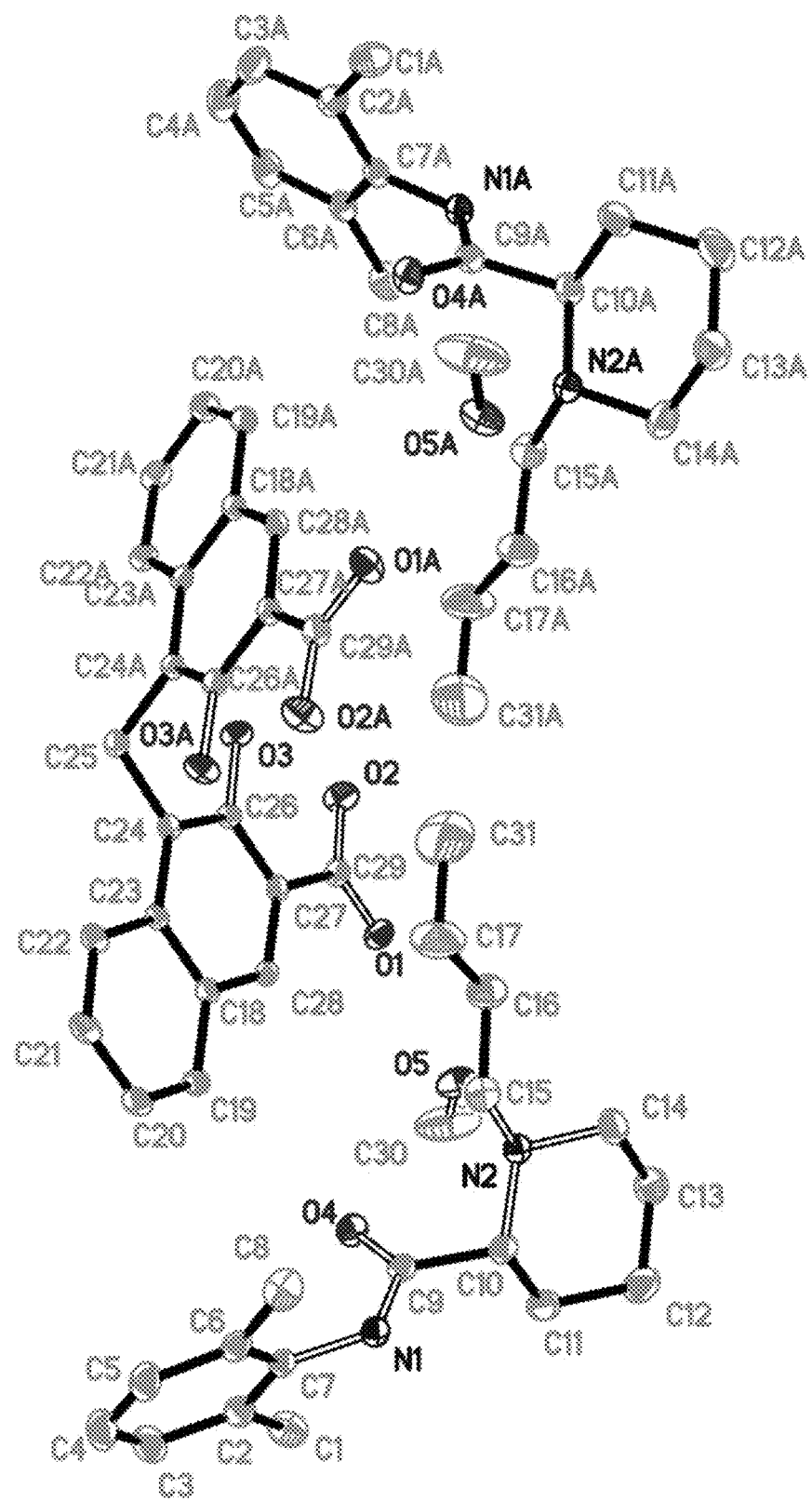
FIG. 4 shows an X-ray single crystal diffraction pattern of a bis(bupivacaine) pamoate.
Figure 5:
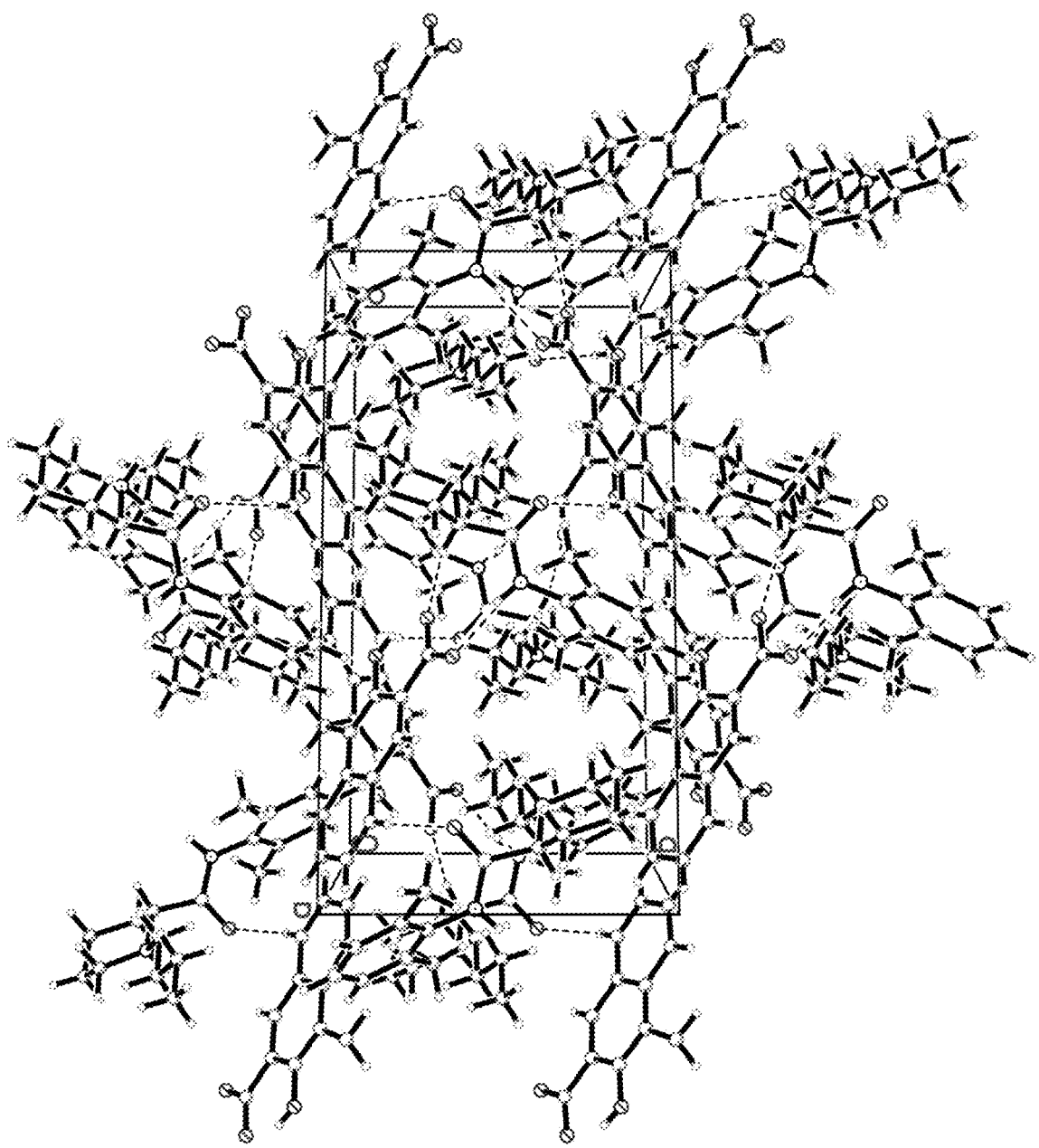
FIG. 5 shows a crystal cell packing diagram (a) of bis(bupivacaine) pamoate.
Figure 6:
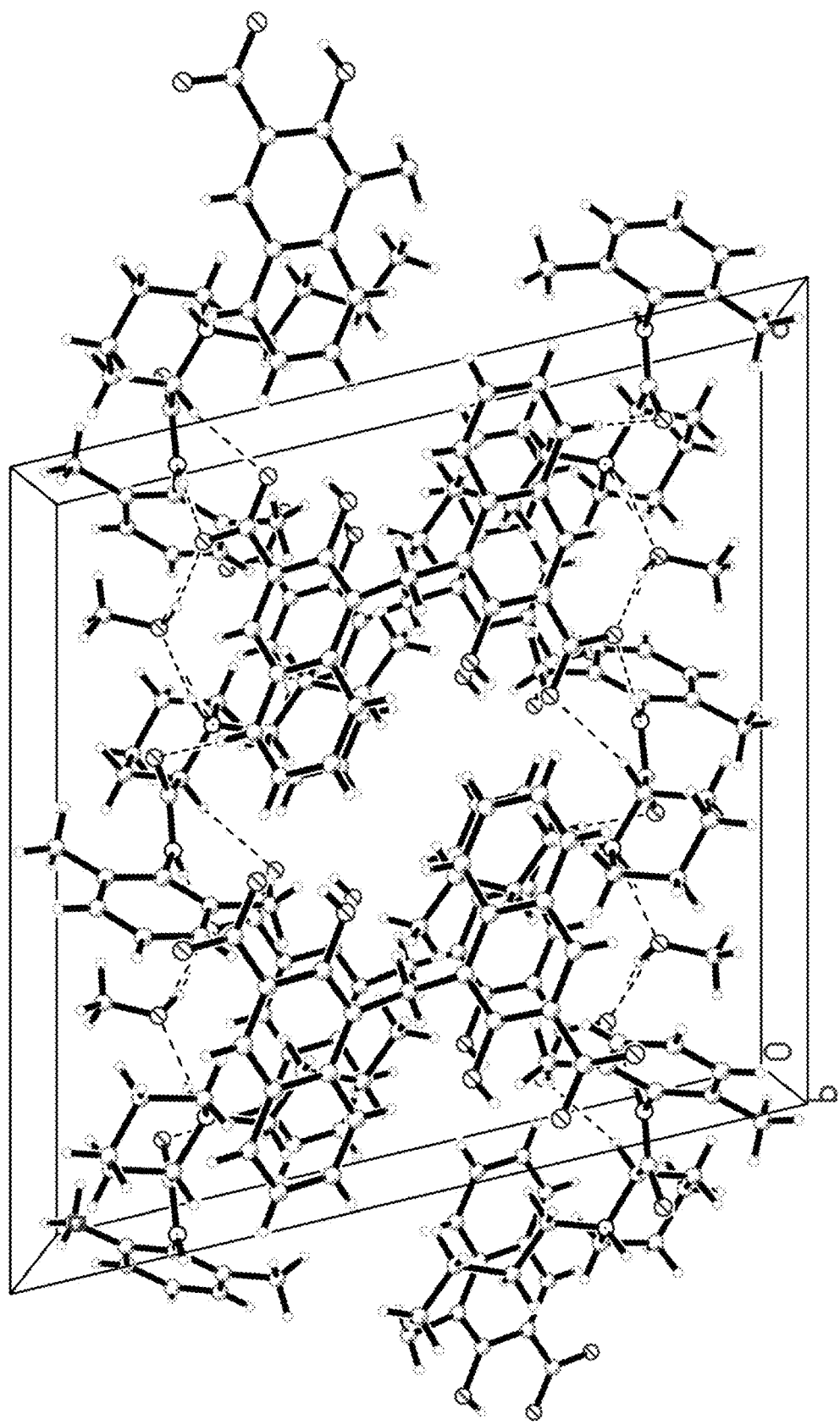
FIG. 6 shows a crystal cell packing diagram (b) of bis(bupivacaine) pamoate.
Figure 7:
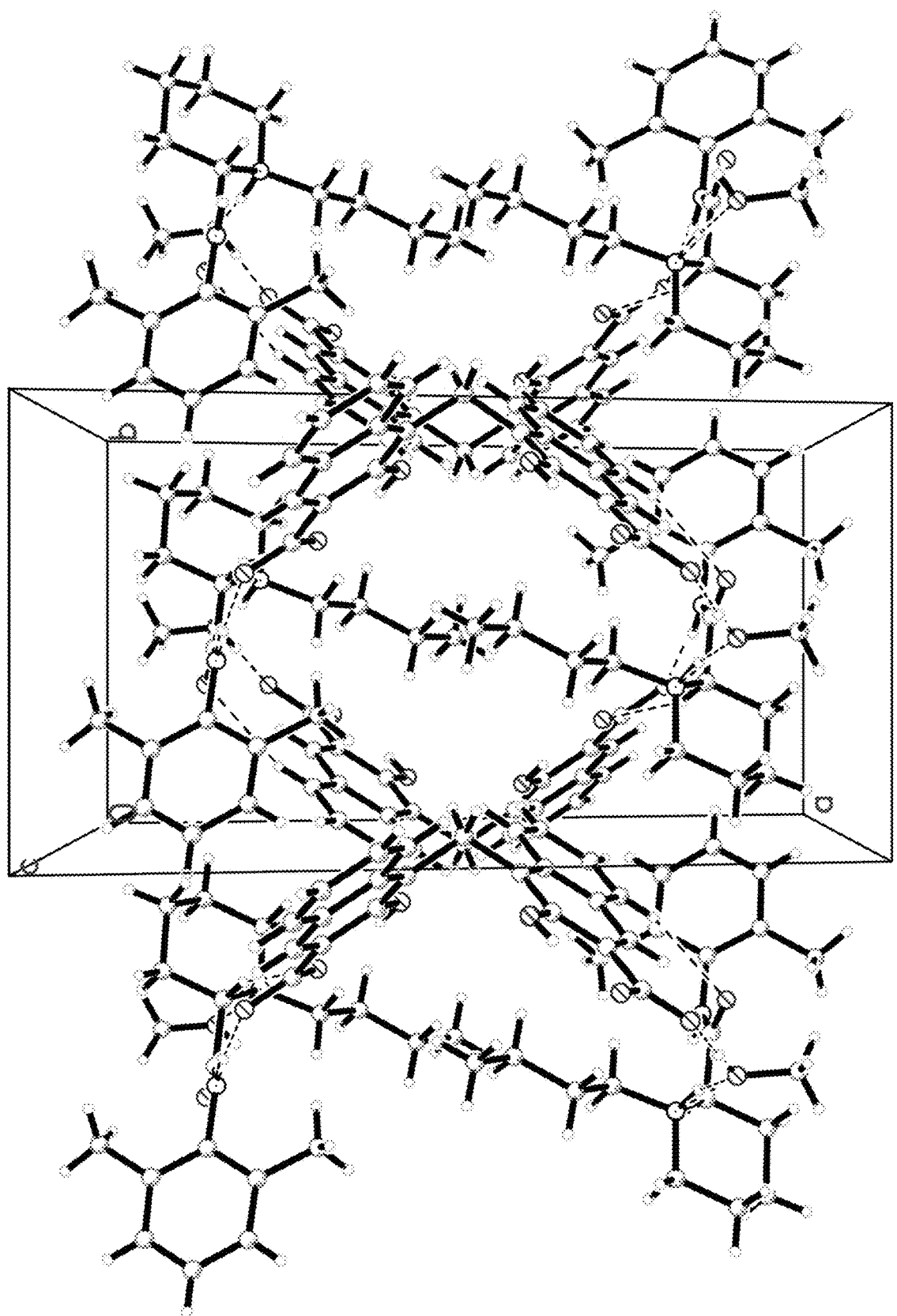
FIG. 7 shows a crystal cell packing diagram (c) of bis(bupivacaine) pamoate.

The above clear solution (about 2 mL) obtained by heating was diluted with acetone/methanol (1:1, V/V) by a factor of two, and then left standing at room temperature for crystallization for about 10 days, to obtain a bis(bupivacaine) pamoate single crystal. The single crystal test data were determined through Single Crystal X-ray diffraction (Bruker Kappa Apex Duo), and shown in the table below. The Single Crystal X-ray diffraction pattern is as shown in FIG. 4. The crystal cell packing diagrams are as shown in FIGS. 5, 6 and 7. The results indicated that the product was a methanol solvate of bis(bupivacaine) pamoate.

| | |
|---|---|
| Chemical formula | $C_{61}H_{80}N_4O_{10}$, i.e., $2(C_{18}H_{28}N_2O)\cdot C_{23}H_{16}O_6\cdot 2(CH_3OH)$ |
| Formula weight | 1029.29 |
| Temperature | 296(2) K |
| Wavelength | 0.71073 Å |
| Crystal system | Monoclinic |
| Space group | P2/c |
| Unit cell parameter | a = 18.23(2) Å α = 90°. |
| | b = 9.517(12) Å β = 103.44(2)°. |
| | c = 18.40(2) Å γ = 90°. |
| Volume | 3104(7) Å$^3$ |
| Z | 2 |
| Calculated density | 1.101 Mg/m$^3$ |
| Absorption coefficient | 0.074 mm$^{-1}$ |
| F(000) | 1108 |
| Crystal size | 0.280 × 0.260 × 0.220 mm$^3$ |
| θ range for data collection | 2.276 to 25.008°. |
| Index range | −19 <= h <= 21, −11 <= k <= 10, −21 <= 1 <= 21 |
| Collected diffraction points | 16083 |
| Independent diffraction points | 5475 [R(int) = 0.0336] |
| The integrity of θ = 25.008° | 99.8% |
| Fine tuning method | Full-matrix least-squares on F2 |
| Data/Limitation/Parameter | 5475/1/350 |
| F$^2$ fitting degree | 1.037 |
| R index [I > 2sigma(I)] | R1 = 0.0805, wR2 = 0.2436 |
| R index (full data) | R1 = 0.1109, wR2 = 0.2791 |
| Extinction coefficient | n/a |
| Maximal difference peak and hole | 1.317 and −0.316 e.Å$^{-3}$ |

Preparation Example 12. Preparation of Bis(Bupivacaine) Pamoate, Polymorph B

Bupivacaine (216 g, 0.75 mol) and pamoic acid (116 g, 0.3 mol) were added into a mixed solvent of 1000 mL methanol and 1000 mL acetone, and heated to clear. The solution was filtered while it was hot, then slowly cooled to room temperature, stirred and subjected to crystallization for 4 h, and filtered. The filter cake was washed in slurry with 500 mL of a mixed solvent of methanol/acetone (1:1, V/V), filtered, and then dried in vacuum at 60° C., to obtain 231 g of a light yellow solid, i.e., bis(bupivacaine) pamoate, with a yield of 79.9%. It was analyzed and identified through High Performance Liquid Chromatography (HPLC-a) and Nuclear Magnetic Resonance (NMR) that the molar ratio of bupivacaine to pamoic acid was 2:1, with methanol residue. The content of methanol was analyzed to be 5.26% through Gas Chromatography (GC).

Endothermic Peak: 119.0° C. and 138.5° C. (Differential Thermal Analysis, SHIMADZU DTG-60A, temperature increasing rate: 10° C./min).

Figure 13:
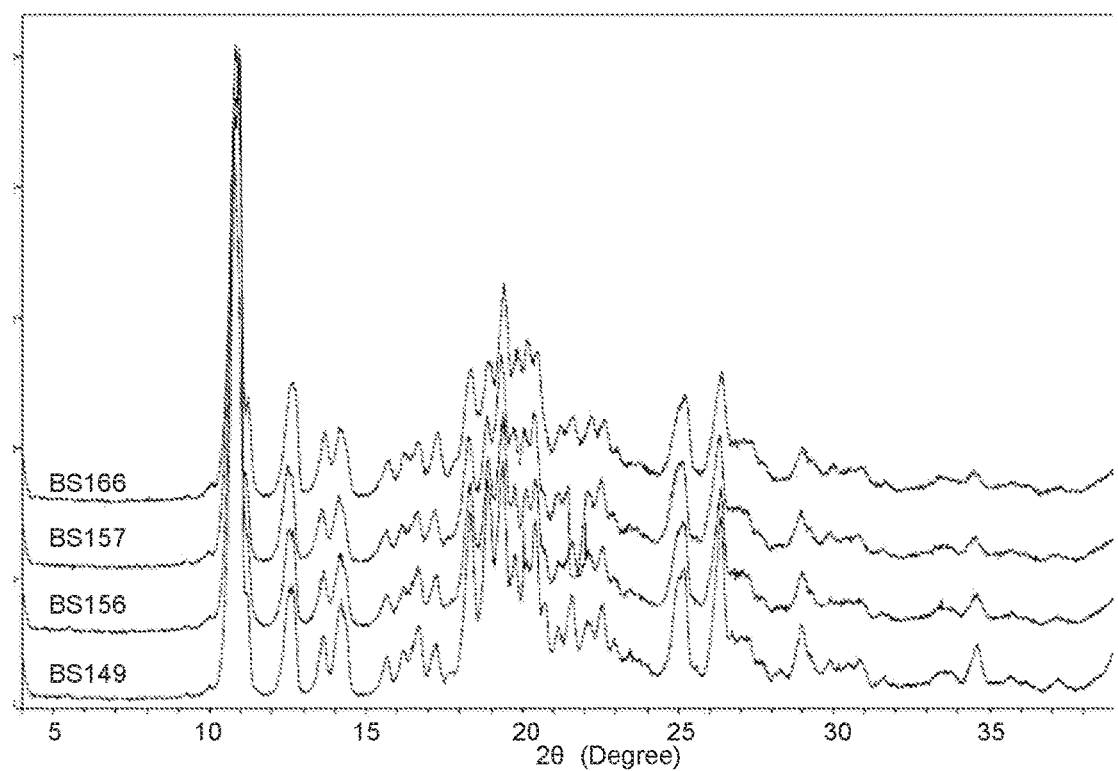
FIG. 13 shows a comparative X-ray powder diffraction pattern of bis(bupivacaine) pamoate having a polymorph B.

The X-ray powder diffraction patterns are as shown in FIG. 2 (polymorph B) and BS149 in FIG. 13.

Preparation Example 13. Preparation of Bis(Bupivacaine) Pamoate, Polymorph B

Bupivacaine (5.04 g, 17.5 mol) and pamoic acid (1.94 g, 5 mol) were added into 70 mL methanol, heated to clear, slowly cooled to room temperature, stirred and subjected to crystallization overnight, and filtered. The filter cake was rinsed with a little methanol, dried in vacuum at 50° C., to obtain 3.7 g of a yellow solid, i.e., bis(bupivacaine) pamoate, with a yield of 76.67%. It was analyzed and identified through High Performance Liquid Chromatography (HPLC-a) and Nuclear Magnetic Resonance (NMR) that the molar ratio of bupivacaine to pamoic acid was 2:1, with methanol residue.

Endothermic Peak: 121.4° C. and 138.5° C. (Differential Thermal Analysis, SHIMADZU DTG-60A, temperature increasing rate: 10° C./min).

It is shown from the X-ray powder diffraction pattern that the product has a polymorph B, as shown in B S166 of FIG. 13.

Preparation Example 14. Preparation of Bis(Bupivacaine) Pamoate, Polymorph B

Bupivacaine (5.04 g, 17.5 mol) and pamoic acid (1.94 g, 5 mol) were added into 47.5 mL methanol, heated to clear, supplemented with 2.5 mL water (corresponding to 95% methanol), slowly cooled to room temperature, stirred and subjected to crystallization overnight, and filtered. The filter cake was rinsed with a little methanol, dried in vacuum at 50° C., to obtain 3.9 g of a yellow solid, i.e., bis(bupivacaine) pamoate, with a yield of 80.8%. It was analyzed and identified through High Performance Liquid Chromatography (HPLC-a) and Nuclear Magnetic Resonance (NMR) that the molar ratio of bupivacaine to pamoic acid was 2:1, with methanol residue.

Endothermic Peak: 120.3° C. and 140.3° C. (Differential Thermal Analysis, SHIMADZU DTG-60A, temperature increasing rate: 10° C./min).

It was shown from the X-ray powder diffraction pattern that the product had a polymorph B, as shown in BS157 of FIG. 13.

Preparation Example 15. Preparation of Bis(Bupivacaine) Pamoate, Polymorph A 7.21 g (25 mmol) of bupivacaine was dissolved in 200 mL anhydrous ethanol, and heated to reflux. A solution of pamoic acid (3.88 g, 10 mmol) of pamoic acid dissolved in 10 mL dimethyl sulfoxide) was slowly added thereto dropwise. After that, the reaction mixture was kept refluxing for 2 h, then slowly cooled to 30° C., and filtered. The filter cake was washed with a little ethanol, and dried in vacuum at 50° C., to obtain 7.1 g of a yellow solid, i.e., bis(bupivacaine) pamoate, with a yield of 74%. It was analyzed and identified through High Performance Liquid Chromatography (HPLC-a) and Nuclear Magnetic Resonance (NMR) that the molar ratio of bupivacaine to pamoic acid was 2:1. It was analyzed through GC that the content of ethanol was 8.85%.

Endothermic Peak: 149.3° C. (Differential Thermal Analysis, SHIMADZU DTG-60A, temperature increasing rate: 10° C./min).

Figure 8:
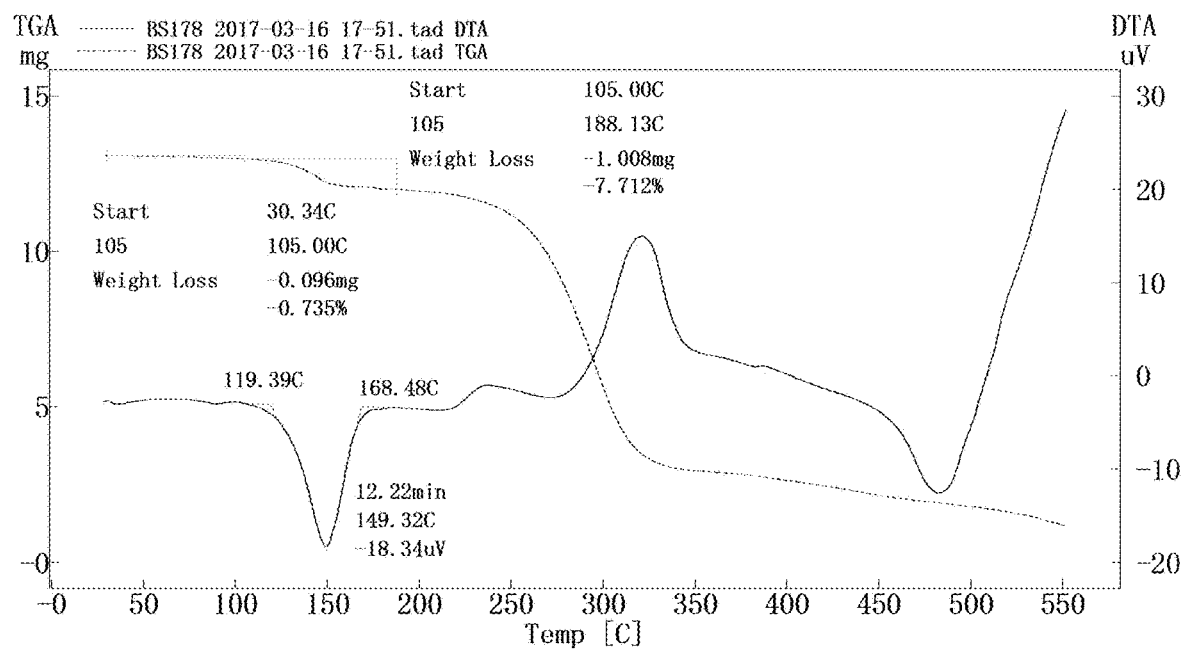
FIG. 8 shows a TGA-DTA graph of bis(bupivacaine) pamoate (polymorph A).

Weight loss when melted (from 105 to 188° C.): 7.712% (Thermalgravimetric Analysis, SHIMADZU DTG-60A, temperature increasing rate: 10° C./min). The TGA-DTA diagram is as shown in FIG. 8. The results indicated that the product was an ethanol solvate of bis(bupivacaine) pamoate.

Figure 12:
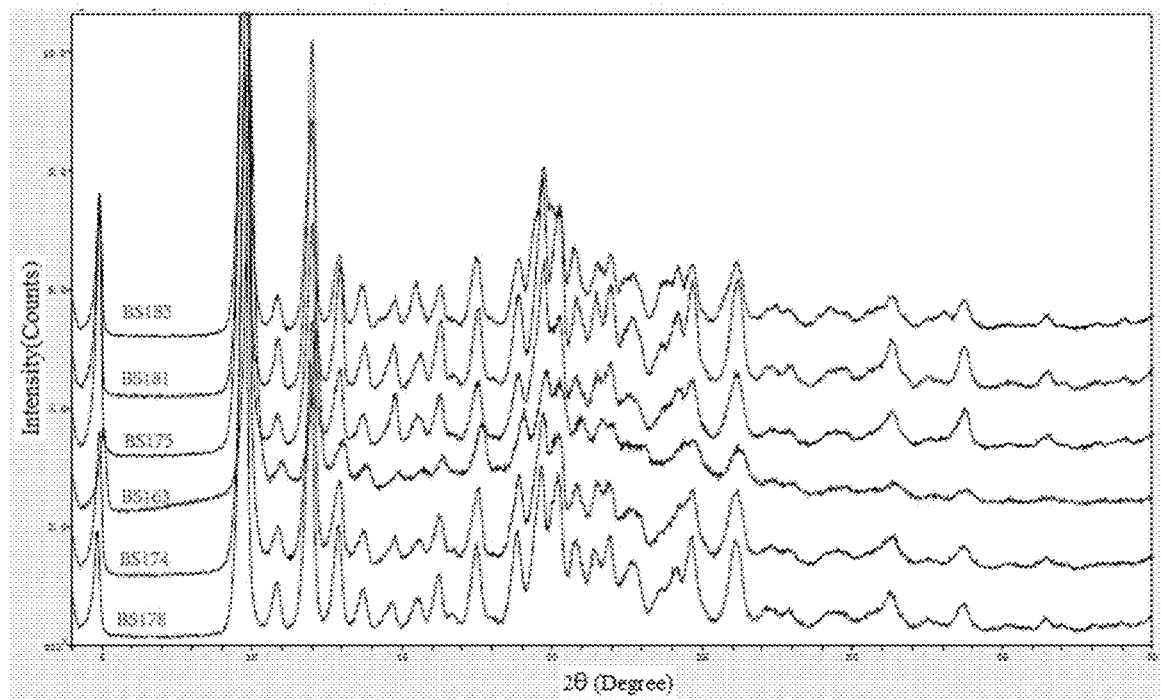
FIG. 12 shows a comparative X-ray powder diffraction pattern of bis(bupivacaine) pamoate having a polymorph A.

The X-ray powder diffraction patterns are as shown in FIG. 1 (polymorph A) and BS178 of FIG. 12.

Preparation Example 16. Preparation of Bis(Bupivacaine) Pamoate, Polymorph A 50.5 g (175 mmol) of bupivacaine was dissolved in 1400 mL anhydrous ethanol, and heated to reflux. A solution of pamoic acid in dimethyl sulfoxide (27.2 g, 70 mmol) of pamoic acid dissolved in 76 mL dimethyl sulfoxide) was slowly added thereto dropwise. After that, the reaction mixture was kept refluxing for 2 h, then slowly cooled to 30° C., and filtered. The filter cake was washed with a little ethanol, and dried in vacuum at 50° C., to obtain 51.3 g of a yellow solid, i.e., bis(bupivacaine) pamoate, with a yield of 75.9%. It was analyzed and identified through High Performance Liquid Chromatography (HPLC-a) and Nuclear Magnetic Resonance (NMR) that the molar ratio of bupivacaine to pamoic acid was 2:1. It was analyzed through GC that the content of ethanol was 7.48%.

Endothermic Peak: 149.7° C. (Differential Thermal Analysis, SHIMADZU DTG-60A, temperature increasing rate: 10° C./min).

Weight loss when melted (from 105 to 180° C.): 7.137% (Thermalgravimetric Analysis, SHIMADZU DTG-60A, temperature increasing rate: 10° C./min).

It was shown from the X-ray powder diffraction pattern that the product had a polymorph A, as shown in BS181 of FIG. 12.

Preparation Example 17. Preparation of Bis(Bupivacaine) Pamoate, Polymorph A

Bupivacaine (10.08 g, 35 mol) and pamoic acid (3.88 g, 10 mol) were added into 150 mL anhydrous ethanol, heated to reflux for 2 h, slowly cooled to room temperature in 18h with stirring, and filtered. The filter cake was rinsed with a little ethanol, dried in vacuum at 50° C., to obtain 7.18 g of a yellow solid, i.e., bis(bupivacaine) pamoate, with a yield of 74.4%. It was analyzed and identified through High Performance Liquid Chromatography (HPLC) and Nuclear Magnetic Resonance (NMR) that the molar ratio of bupivacaine to pamoic acid was 2:1. The content of ethanol residue was 6.5%.

Endothermic Peak: 142.4° C. (Differential Thermal Analysis, SHIMADZU DTG-60A, temperature increasing rate: 10° C./min).

It was shown from the X-ray powder diffraction pattern that the product had a polymorph A (as shown in BS174 of FIG. 12).

Preparation Example 18. Preparation of Bis(Bupivacaine) Pamoate, Polymorph A 7.21 g (25 mmol) of bupivacaine was dissolved in 200 mL of 95% ethanol, and heated to reflux. A solution of pamoic acid (3.88 g, 10 mmol) in dimethyl sulfoxide (20 mL dimethyl sulfoxide) was slowly added thereto dropwise. After that, the reaction mixture was kept refluxing for 2 h, then slowly cooled to 30° C., and filtered. The filter cake was washed with a little 95% ethanol, and dried in vacuum at 60° C., to obtain 5.4 g of a light yellow solid, i.e., bis(bupivacaine) pamoate, with a yield of 56%. It was analyzed and identified through High Performance Liquid Chromatography (HPLC-a) and Nuclear Magnetic Resonance (NMR) that the molar ratio of bupivacaine to pamoic acid was 2:1. The content of ethanol residue was 5.2%.

Endothermic Peak: 144.2° C. (Differential Thermal Analysis, SHIMADZU DTG-60A, temperature increasing rate: 10° C./min).

From the X-ray powder diffraction pattern, the product was shown to be polymorph A (as shown in BS183 of FIG. 12).

Preparation Example 19. Preparation of Bis(Bupivacaine) Pamoate, Polymorph C 1.5 g of bis(bupivacaine) pamoate (polymorph A) powders obtained in Preparation Example 16 were added into 25 mL purified water, stirred at room temperature for 20 hours, and filtered. The filter cake was rinsed with a little purified water, and the wet product was dried in vacuum at 60° C., to obtain 1.4 g of light yellow solid powders with a yield of 93.3%. It was analyzed and identified through High Performance Liquid Chromatography (HPLC-a) and Nuclear Magnetic Resonance (NMR) that the molar ratio of bupivacaine to pamoic acid was 2:1, without ethanol residue. It was analyzed through Gas Chromatography that the content of ethanol was 0.19%.

Endothermic Peak: 136.2° C. (Differential Thermal Analysis, SHIMADZU DTG-60A, temperature increasing rate: 10° C./min).

Weight loss when melted (from 105 to 185° C.): 3.465% (Thermalgravimetric Analysis, SHIMADZU DTG-60A, temperature increasing rate: 10° C./min).

Figure 9:
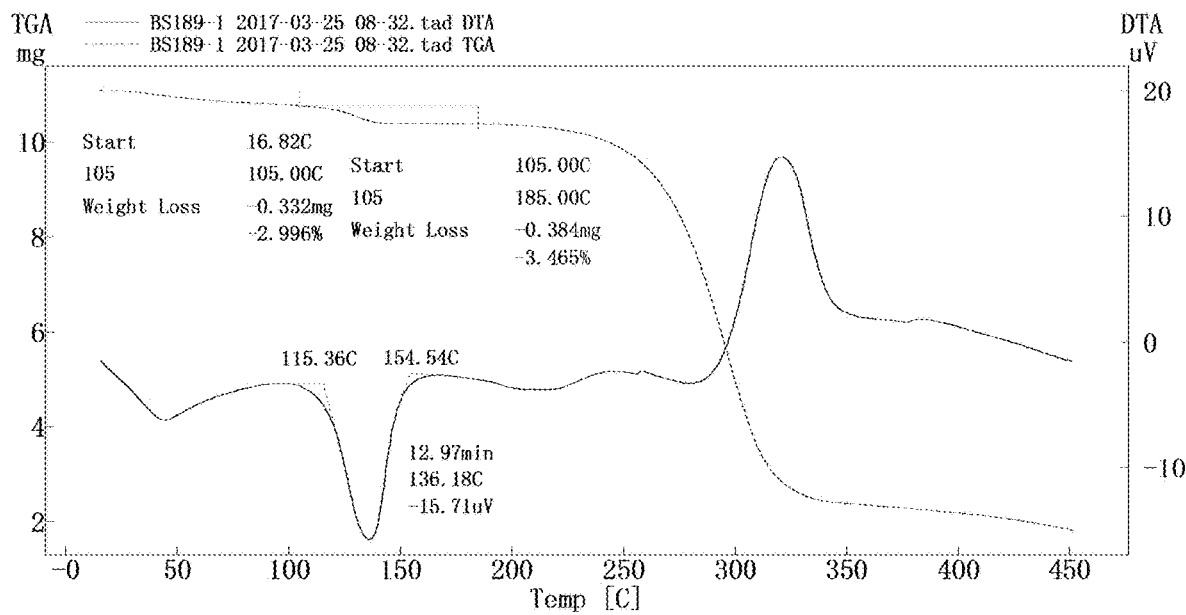
FIG. 9 shows a TGA-DTA graph of bis(bupivacaine) pamoate (polymorph C).

The product was a hydrate of bis(bupivacaine) pamoate. The TGA-DTA diagram is as shown in FIG. 9.

Figure 14:
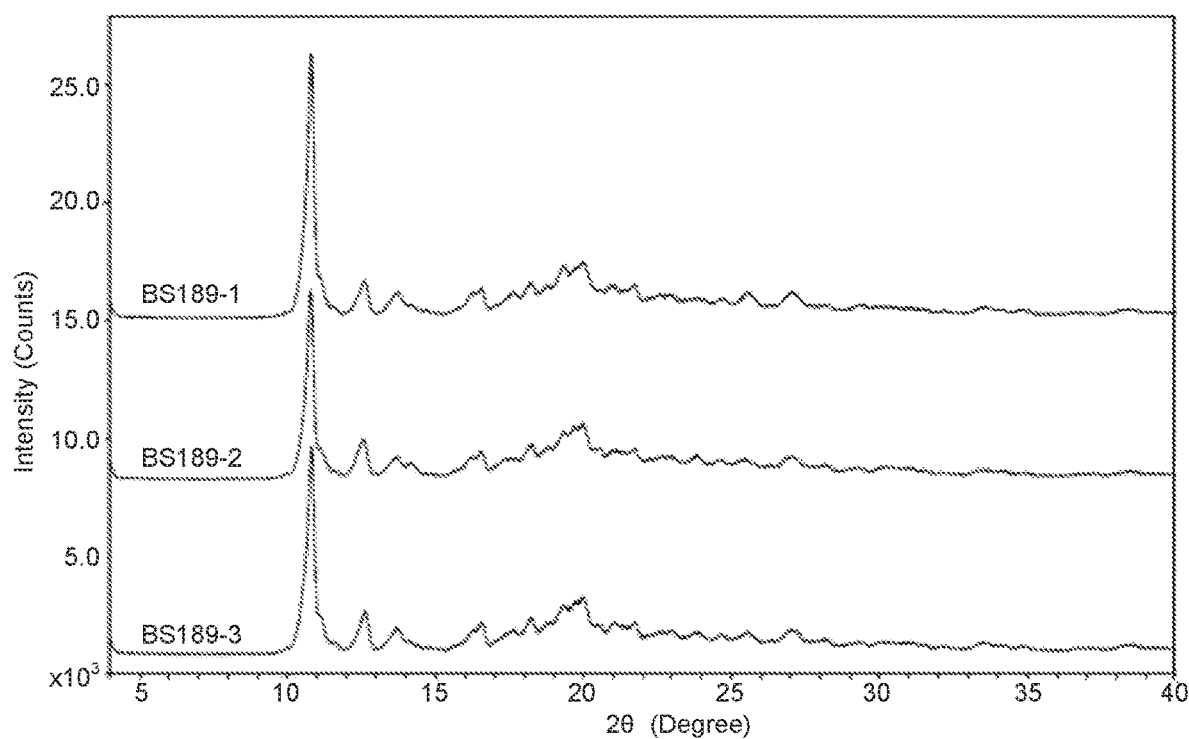
FIG. 14 shows a comparative X-ray powder diffraction pattern of bis(bupivacaine) pamoate having a polymorph C.

The X-ray powder diffraction patterns are as shown in FIG. 3 and FIG. 14 (designated with BS189-1), and the product is defined as polymorph C.

Preparation Example 20. Preparation of Bis(Bupivacaine) Pamoate, Polymorph C 10.3 g of bis(bupivacaine) pamoate (polymorph A) powders obtained in Preparation Example 16 were added into 110 mL purified water, stirred at room temperature for 12 hours, and filtered. The filter cake was rinsed with a little purified water, and the wet product was dried in vacuum at 60° C., to obtain 9.3 g of light yellow solid powders with a yield of 90.3%. It was analyzed and identified through High Performance Liquid Chromatography (HPLC-a) and Nuclear Magnetic Resonance (NMR) that the molar ratio of bupivacaine to pamoic acid was 2:1, without ethanol residue. It was analyzed through Gas Chromatography that the content of ethanol was 0.10%.

Endothermic Peak: 136.7° C. (Differential Thermal Analysis, SHIMADZU DTG-60A, temperature increasing rate: 10° C./min).

Weight loss when melted (from 105 to 185° C.): 3.674% (Thermalgravimetric Analysis, SHIMADZU DTG-60A, temperature increasing rate: 10° C./min). The product was a hydrate of bis(bupivacaine) pamoate.

The X-ray powder diffraction pattern is as shown in FIG. 14 (designated with BS189-2), and the product is defined as polymorph C.

Preparation Example 21. Preparation of Bis(Bupivacaine) Pamoate, Polymorph C 10.0 g of bis(bupivacaine) pamoate (polymorph B) powders obtained in Preparation Example 12 were added into 100 mL purified water, stirred at room temperature for 12 hours, and filtered. The filter cake was rinsed with a little purified water, and the wet product was dried in vacuum at 60° C., to obtain 9.0 g of light yellow solid powders with a yield of 90.0%. It was analyzed and identified through High Performance Liquid Chromatography (HPLC-a) and Nuclear Magnetic Resonance (NMR) that the molar ratio of bupivacaine to pamoic acid was 2:1, without methanol residue. It was analyzed through Gas Chromatography that the content of methanol was 0.15%.

Endothermic Peak: 137.8° C. (Differential Thermal Analysis, SHIMADZU DTG-60A, temperature increasing rate: 10° C./min).

Weight loss when melted (from 105 to 185° C.): 3.575% (Thermalgravimetric Analysis, SHIMADZU DTG-60A, temperature increasing rate: 10° C./min).

The product was a hydrate of bis(bupivacaine) pamoate.

The X-ray powder diffraction pattern is as shown in FIG. 14 (designated with BS189-3), and the product is defined as polymorph C.

The diffraction angle data in the X-ray powder diffraction patterns of Examples 19 to 21 are compared as follows. The results about polymorph are consistent with each other, but there is a difference between the peak numbers. There are peaks at all of the diffraction angles (2θ) of 10.8, 12.6, 13.7, 16.5, 18.2, 19.4, 20.0 and 27.0, the maximum peak is generally at the diffraction angle of 10.8, and three peaks at the diffraction angles of 10.8, 12.6 and 13.7 are typical characteristic peaks.

| BS189-1 | BS189-2 | BS189-3 | Minimum | Average | Maximum |
|---|---|---|---|---|---|
| 10.801 | 10.800 | 10.820 | 10.800 | 10.8 | 10.820 |
| 12.619 | 12.560 | 12.620 | 12.560 | 12.6 | 12.620 |
| 13.701 | 13.640 | 13.700 | 13.640 | 13.7 | 13.701 |
|  | 14.199 |  | 14.199 | 14.2 | 14.199 |
| 16.502 | 16.502 | 16.542 | 16.502 | 16.5 | 16.542 |
| 17.600 | 17.359 | 17.601 | 17.359 | 17.5 | 17.601 |
| 18.200 | 18.221 | 18.240 | 18.200 | 18.2 | 18.240 |
| 19.360 | 19.359 | 19.360 | 19.359 | 19.4 | 19.360 |
| 20.000 | 19.980 | 20.000 | 19.980 | 20.0 | 20.000 |
| 21.020 | 21.040 | 21.021 | 21.020 | 21.0 | 21.040 |
| 21.739 | 21.740 | 21.739 | 21.739 | 21.7 | 21.740 |
| 22.899 | 22.879 | 22.961 | 22.879 | 22.9 | 22.961 |
| 23.920 | 23.801 | 23.899 | 23.801 | 23.9 | 23.920 |
| 24.639 | 24.699 | 24.738 | 24.639 | 24.7 | 24.738 |
| 25.618 | 25.482 | 25.539 | 25.482 | 25.5 | 25.618 |
| 27.040 | 27.060 | 27.060 | 27.040 | 27.1 | 27.060 |
|  | 28.221 | 28.143 | 28.143 | 28.2 | 28.221 |
| 29.338 | 29.282 | 29.340 | 29.282 | 29.3 | 29.340 |
|  | 30.220 | 30.177 | 30.177 | 30.2 | 30.220 |
|  | 31.023 | 31.059 | 31.023 | 31.0 | 31.059 |
| 33.522 | 33.581 | 33.520 | 33.520 | 33.5 | 33.581 |
| 34.819 | 34.159 | 36.678 | 34.159 | 35.2 | 36.678 |
|  | 37.258 |  | 37.258 | 37.3 | 37.258 |
| 38.420 | 38.499 | 38.358 | 38.358 | 38.4 | 38.499 |

Preparation Example 22. Other Preparations and Comparison Between the X-Ray Powder Diffraction Patterns Polymorphs A were prepared in different manners such as different solvent ratio, different material amounts, different crystallization rate and the like. A comparison between the diffraction angles (2θ) in the X-ray powder diffraction patterns indicated that the diffraction patterns were substantially consistent with each other. The averages (bold) of characteristic peak angles common in 6 groups of above patterns were 4.9, 9.8, 10.9, 12.0, 12.9, 13.7, 14.7, 15.6, 16.3, 17.6, 18.9, 19.7, 20.2, 20.8, 21.5, 21.9, 22.7, 24.2, 24.7, 26.1, 27.3, 27.9, 31.0, 33.7, and 36.5 respectively. The underlined angle values existed in all 6 patterns, and had a certain abundance and a certain resolution. The value for the maximum peak was generally 9.8. The batch information and X-ray powder diffraction pattern for each batch are as shown in FIG. 12 and the table below. The peaks at the diffraction angles of 21.9, 22.7, 24.2 and 27.9 for BS163 were not identified, but the comparison between the patterns indicated that the polymorphs were consistent with each other. Four unidentified peaks represented 16% of total 25 peaks. Here, the peak at the diffraction angle of 4.9 is the characteristic peak mostly distinct from other polymorphs; and three peaks at the diffraction angles of 4.9, 9.8 and 12.0 are typical characteristic peaks.

| Batch | Preparation method | Solvent system |
|---|---|---|
| BS163 | Same as Preparation Example 17 | Anhydrous ethanol |
| BS174 | Preparation Example 17 | Anhydrous ethanol |
| BS175 | Same as Preparation Example 15 | Ethanol/dimethylsulfoxide |
| BS178 | Preparation Example 15 | Ethanol/dimethylsulfoxide |
| BS181 | Preparation Example 16 | Ethanol/dimethylsulfoxide |
| BS183 | Preparation Example 18 | Ethanol/dimethylsulfoxide/water |

| Peak No. | BS163 | BS174 | BS175 | BS178 | BS181 | BS183 | Minimum | Average | Maximum |
|---|---|---|---|---|---|---|---|---|---|
| 1 | 5.041 | 4.901 | 4.918 | 4.841 | 4.900 | 4.919 | 4.841 | 4.9 | 5.041 |
| 2 | 9.940 | 9.820 | 9.820 | 9.741 | 9.800 | 9.820 | 9.741 | 9.8 | 9.940 |
| 3 | 10.980 | 10.860 | 10.859 | 10.840 | 10.899 | 10.86 | 10.840 | 10.9 | 10.980 |
| 4 | 12.160 | 12.000 | 12.019 | 11.941 | 12.000 | 12.001 | 11.941 | 12.0 | 12.160 |
| 5 | 13.039 | 12.939 | 12.958 | 12.880 | 12.940 | 12.939 | 12.880 | 12.9 | 13.039 |
| 6 | 13.760 | 13.680 | 13.662 | 13.681 | 13.759 | 13.659 | 13.659 | 13.7 | 13.760 |
| 7 | 14.839 | 14.760 | 14.741 | 14.641 | 14.719 | 14.777 | 14.641 | 14.7 | 14.839 |
| 8 | 15.721 | 15.599 | 15.481 | 15.54 | 15.619 | 15.478 | 15.478 | 15.6 | 15.721 |
| 9 | 16.360 | 16.202 | 16.259 | 16.238 | 16.299 | 16.298 | 16.202 | 16.3 | 16.360 |
| 10 | 17.660 | 17.560 | 17.579 | 17.500 | 17.560 | 17.462 | 17.462 | 17.6 | 17.660 |
| 11 | 19.079 | 18.919 | 18.841 | 18.859 | 18.900 | 18.900 | 18.841 | 18.9 | 19.079 |
| 12 | 19.800 | 19.700 | 19.739 | 19.680 | 19.659 | 19.740 | 19.659 | 19.7 | 19.800 |
| 13 | 20.200 | 20.220 | 20.260 | 20.200 | 20.260 | 20.260 | 20.200 | 20.2 | 20.260 |
| 14 | 20.960 | 20.801 | 20.800 | 20.800 | 20.821 | 20.741 | 20.741 | 20.8 | 20.960 |
| 15 | 21.700 | 21.500 | 21.501 | 21.400 | 21.461 | 21.520 | 21.400 | 21.5 | 21.700 |
| 16 | | 21.841 | 21.959 | 21.920 | 21.940 | 21.921 | 21.841 | 21.9 | 21.959 |
| 17 | | 22.800 | 22.620 | 22.679 | 22.660 | 22.739 | 22.620 | 22.7 | 22.800 |
| 18 | | 24.259 | 24.200 | 24.12 | 24.180 | 24.200 | 24.120 | 24.2 | 24.259 |
| 19 | 24.640 | 24.698 | 24.699 | 24.659 | 24.660 | 24.680 | 24.640 | 24.7 | 24.699 |
| 20 | 26.141 | 26.179 | 26.100 | 26.061 | 26.180 | 26.140 | 26.061 | 26.1 | 26.180 |
| 21 | 27.462 | 27.264 | 27.281 | 27.160 | 27.341 | 27.422 | 27.160 | 27.3 | 27.462 |
| 22 | | 27.860 | 27.903 | 27.900 | 27.881 | 27.960 | 27.860 | 27.9 | 27.960 |
| 23 | 31.322 | 31.261 | 31.340 | 31.241 | 31.339 | 29.701 | 29.701 | 31.0 | 31.340 |
| 24 | 33.819 | 33.721 | 33.760 | 33.739 | 33.720 | 33.720 | 33.720 | 33.7 | 33.819 |
| 25 | 36.482 | 36.556 | 36.560 | 36.423 | 36.540 | 36.517 | 36.423 | 36.5 | 36.560 |

Polymorphs B were prepared in different manners such as different solvent ratio, different material amounts, different crystallization rate and the like. A comparison between the diffraction angles (2θ) in the X-ray powder diffraction patterns indicated that the diffraction patterns were substantially consistent with each other. The averages (bold) of characteristic peak angles common in 4 groups of above patterns were 10.9, 12.6, 13.7, 14.2, 15.7, 16.7, 17.3, 18.3, 18.9, 19.4, 20.4, 22.1, 25.1, 26.4, 27.1, 29.0, 33.6, 34.6 and 39.0 respectively. The underlined angle values existed in all 4 patterns, and had a certain abundance and a certain resolution. The value for the maximum peak was generally 10.9. The batch information and X-ray powder diffraction pattern for each batch are as shown in FIG. 13 and the table below.

It was found from a comparison with polymorph C that all patterns had common characteristic peaks at the diffraction angles of 10.9, 12.6 and 13.7, but the intensity of the characteristic peak at the diffraction angle of 10.9 is low. The relative intensity ratio between three peaks was different from that having a polymorph C. In combination with the Thermogravimetric Analysis and Gas Chromatograph (Preparation Example 12), the product was a methanol solvate, which had a chemical composition different from that having a polymorph C.

| Batch | Preparation method | Solvent system |
|---|---|---|
| BS156 | Same as Preparation Example 12 | Methanol/acetone |
| BS157 | Preparation Example 14 | Methanol/water |
| BS149 | Preparation Example 12 | Methanol/acetone |
| BS166 | Preparation Example 13 | Methanol |

| Peak No. | BS156 | BS157 | BS149 | BS166 | Minimum | Average | Maximum |
|---|---|---|---|---|---|---|---|
| 1 | 10.96 | 10.76 | 10.94 | 10.84 | 10.76 | 10.9 | 10.96 |
| 2 | 12.58 | 12.52 | 12.66 | 12.62 | 12.52 | 12.6 | 12.66 |
| 3 | 13.66 | 13.62 | 13.679 | 13.641 | 13.62 | 13.7 | 13.68 |
| 4 | 14.179 | 14.14 | 14.22 | 14.14 | 14.14 | 14.2 | 14.22 |
| 5 | 15.679 | 15.642 | 15.679 | 15.621 | 15.62 | 15.7 | 15.68 |
| 6 | 16.201 | 16.16 | 16.181 | | 16.16 | 16.2 | 16.20 |
| 7 | 16.661 | 16.621 | 16.68 | 16.66 | 16.62 | 16.7 | 16.68 |
| 8 | 17.28 | 17.201 | 17.278 | 17.319 | 17.20 | 17.3 | 17.32 |

-continued

| Peak No. | BS156 | BS157 | BS149 | BS166 | Minimum | Average | Maximum |
|---|---|---|---|---|---|---|---|
| 9 | 18.341 | 18.3 | 18.321 | 18.36 | 18.30 | 18.3 | 18.36 |
| 10 | 18.901 | 18.881 | 18.901 | 18.90 | 18.88 | 18.9 | 18.90 |
| 11 | 19.38 | 19.32 | 19.379 | 19.419 | 19.32 | 19.4 | 19.42 |
| 12 | 20.44 | 20.361 | 20.439 | 20.46 | 20.36 | 20.4 | 20.46 |
| 13 | 21.601 | | 21.6 | 21.634 | 21.60 | 21.6 | 21.63 |
| 14 | 22.041 | 22.082 | 22.081 | 22.201 | 22.04 | 22.1 | 22.20 |
| 15 | 22.581 | | 22.58 | 22.62 | 22.58 | 22.6 | 22.62 |
| 16 | 25.14 | 25.04 | 25.18 | 25.22 | 25.04 | 25.1 | 25.22 |
| 17 | 26.379 | 26.321 | 26.341 | 26.361 | 26.32 | 26.4 | 26.38 |
| 18 | 27.08 | 27.069 | 27.161 | 27.261 | 27.07 | 27.1 | 27.26 |
| 19 | 28.98 | 28.979 | 28.96 | 29.290 | 28.96 | 29.0 | 28.98 |
| 20 | 33.456 | 33.516 | 33.779 | 33.48 | 33.46 | 33.6 | 33.78 |
| 21 | 34.581 | 34.56 | 34.619 | 34.498 | 34.50 | 34.6 | 34.62 |
| 22 | 35.703 | 35.719 | 35.7 | | 35.70 | 35.7 | 35.72 |
| 23 | 38.982 | 39.002 | 39.059 | 39.021 | 39.00 | 39.0 | 39.06 |

Preparation Example 23. Preparation of Bis(Bupivacaine) Pamoate 6.34 g (22 mmol) of bupivacaine and 3.88 g (10 mmol) of pamoic acid were dissolved in 20 mL dimethyl sulfoxide at room temperature. Anhydrous ethanol (200 mL) was slowly added thereto. A large amount of solid was precipitated, and filtered. The filter cake was washed with a little ethanol, and dried in vacuum at 50° C., to obtain 8.80 g of a yellow solid, i.e., bis(bupivacaine) pamoate, with a yield of 91.3%. It was analyzed and identified through High Performance Liquid Chromatography (HPLC-a) and Nuclear Magnetic Resonance (NMR) that the molar ratio of bupivacaine to pamoic acid was 2:1.

Preparation Example 24. Preparation of Bis(Bupivacaine) Pamoate 6.34 g (22 mmol) of bupivacaine and 3.88 g (10 mmol) of pamoic acid were dissolved in 30 mL N,N-dimethyl formamide at room temperature. Anhydrous ethanol (200 mL) was slowly added thereto. A large amount of solid was precipitated, filtered and filtered. The filter cake was washed with a little ethanol, and dried in vacuum at 50° C., to obtain 8.97 g of a yellow solid, i.e., bis(bupivacaine) pamoate, with a yield of 93.05%. It was analyzed and identified through High Performance Liquid Chromatography (HPLC-a) and Nuclear Magnetic Resonance (NMR) that the molar ratio of bupivacaine to pamoic acid was 2:1.

Preparation Example 25. Preparation of Bis(Bupivacaine) Pamoate 5.76 g (20 mmol) of bupivacaine and 3.88 g (10 mmol) of pamoic acid were dissolved in 20 mL dimethyl sulfoxide at room temperature. Water (100 mL) was slowly added thereto. A large amount of solid was precipitated, filtered and filtered. The filter cake was washed with a little water, and dried in vacuum at 50° C., to obtain 9.6 g of a yellow solid, i.e., bis(bupivacaine) pamoate, with a yield of 99.6%. It was analyzed and identified through High Performance Liquid Chromatography (HPLC-a) and Nuclear Magnetic Resonance (NMR) that the molar ratio of bupivacaine to pamoic acid was 2:1.

Preparation Example 26. Preparation of Bis(Bupivacaine) Pamoate

Bupivacaine (17.3 g, 0.06 mol) and pamoic acid (11.6 g, 0.03 mol) were added into a mixed solvent of 100 mL methanol and 100 mL acetone, and heated to clear. The solution was filtered while it was hot, and then spray dried, to obtain 29 g of a light yellow solid, i.e., bis(bupivacaine) pamoate. It was analyzed and identified through High Performance Liquid Chromatography (HPLC-a) and Nuclear Magnetic Resonance (NMR) that the molar ratio of bupivacaine to pamoic acid was 2:1, with methanol residue.

Preparation Example 27. Preparation of Bis(Bupivacaine) Pamoate

Bupivacaine (5.76 g, 20 mmol) and pamoic acid (3.88 g, 10 mmol) were added into a mixed solvent of 33 mL methanol and 33 mL acetone, and heated to clear. The solution was film evaporated to remove solvent, to obtain 9.64 g of a light yellow solid, i.e., bis(bupivacaine) pamoate. It was analyzed and identified through High Performance Liquid Chromatography (HPLC-a) and Nuclear Magnetic Resonance (NMR) that the molar ratio of bupivacaine to pamoic acid was 2:1, with methanol residue.

Preparation Example 28. Preparation of Bis(Bupivacaine) Pamoate

Bupivacaine (5.76 g, 20 mmol) and pamoic acid (3.88 g, 10 mmol) were added into a reaction flask under the protection of argon, heated (150° C.) to be melted, cooled to be solidified, and then ground, to obtain 9.64 g of a light yellow solid, i.e., bis(bupivacaine) pamoate. It was analyzed and identified through High Performance Liquid Chromatography (HPLC-a) and Nuclear Magnetic Resonance (NMR) that the molar ratio of bupivacaine to pamoic acid was 2:1. No obvious characteristic peak existed in the X-ray powder diffraction pattern, indicating that the product was substantially amorphous. From the TG/DSC, the product was shown to be a single material, rather than a simply physical mixture of two mixed materials. It was also shown from the weight loss calculation that there was no solvate. The above material was substantially consistent with the product obtained in Formulation Example 30.

Preparation Example 29. Preparation of Bis(Bupivacaine) Pamoate, Polymorph C 7.73 kg (26.8 mol) of bupivacaine was dissolved in 160 kg anhydrous ethanol, and heated to reflux and to be dissolved to clear. A solution of pamoic acid in dimethyl sulfoxide (4.16 kg (10.7 mol) of pamoic acid dissolved in 22.9 kg dimethyl sulfoxide) was slowly added thereto dropwise.

After that, the reaction mixture was kept refluxing for 0.5 h, then slowly cooled to room temperature and stirred overnight, and filtered. The filter cake was rinsed with ethanol, and then rinsed with water for injection. The wet filter cake was then transferred to a reaction kettle, supplemented with 220 kg water for injection, stirred at room temperature overnight, filtered, rinsed with water for injection, and sucked to dryness. The wet product was blow dried at 60° C. to weight loss on drying less than 5%. 9.3 kg of a light yellow solid was obtained with a yield of 86.6%, which was a hydrate of bis(bupivacaine) pamoate. It was analyzed and identified through High Performance Liquid Chromatography (HPLC-a) and Nuclear Magnetic Resonance (NMR) that the molar ratio of bupivacaine to pamoic acid was 2:1. It was analyzed through GC that the content of ethanol was <0.1%. From the TG/DSC analysis in combination with the X-ray powder diffraction pattern, the product was shown to be polymorph C.

Preparation Example 30. Preparation of Non-Solvate of Bis(Bupivacaine) Pamoate 5 g of the solid having a polymorph C obtained in Preparation Example 29 was placed into an oven at 150° C. for 1 h such that the solid was melted, cooled to room temperature, and ground into fine powders.

From the X-ray powder diffraction pattern (FIG. 16), the product was shown to be amorphous, and there was no obvious diffraction peak.

Figure 17:
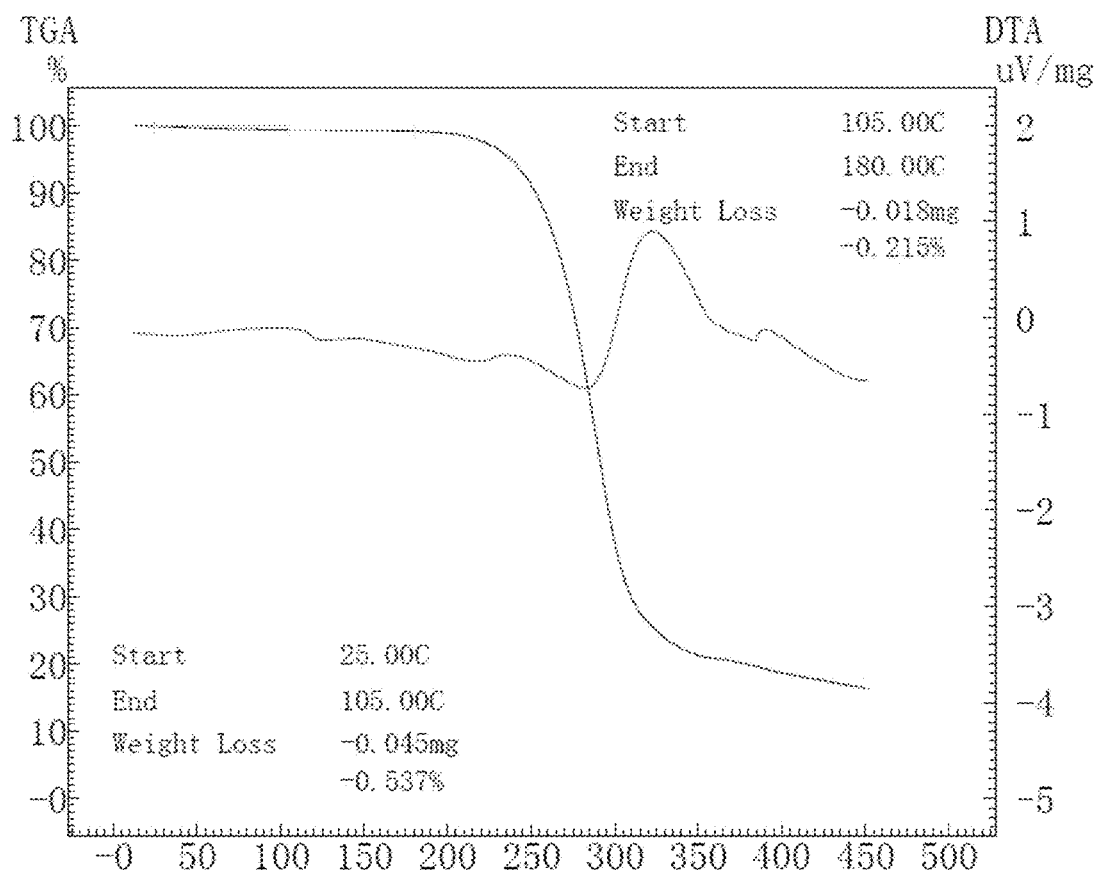
FIG. 17 shows a TG/DSC graph of the amorphous bis(bupivacaine) pamoate prepared in Preparation Example 30.

The TG/DSC analysis (FIG. 17) showed that the melting point was about 112° C.; the melting endothermic peak was at 123° C.; and there were no obvious weight loss (<1%) in two temperature ranges of 25 to 105° C. and 105 to 180° C., indicating that the product was a non-solvate.

The fine powders obtained was supplemented with water, and magnetically stirred for 24 hours, filtered and dried. From the TG/DSC analysis in combination with the X-ray powder diffraction pattern, the product was shown to be polymorph C.

The above results indicated that the polymorph and the amorphous form were interconvertible.

Preparation Example 31. Preparation of Non-Solvate of Bis(Bupivacaine) Pamoate 5 g of the solid having a polymorph B obtained in Preparation Example 12 was placed into an oven at 150° C. for 1 h such that the solid was melted, cooled to room temperature, and ground into fine powders. From the TG/DSC analysis in combination with the X-ray powder diffraction pattern, the product was shown to be amorphous, which was consistent with the non-solvate obtained in Example 30.

Preparation Example 32. Preparation of Non-Solvate of Bis(Bupivacaine) Pamoate 5 g of the solid having a polymorph A obtained in Preparation Example 16 was placed into an oven at 150° C. for 1 h such that the solid was melted, cooled to room temperature, and ground into fine powders. From the TG/DSC analysis in combination with the X-ray powder diffraction pattern, the product was shown to be amorphous, which was consistent with the non-solvate obtained in Example 30.

Preparation Example 33. Co-Crystal of Bupivacaine and Pamoic Acid

Bupivacaine and pamoic acid were mixed in a molar ratio of 1:1, 2:1 and 4:1, respectively. A portion of each mixture was taken as the physical mixture. The remaining portion was placed into an oven, heated (150° C.) to be melted, cooled to be solidified, and then ground, to obtain a light yellow solid as co-crystal by melting. Additionally, the single component of bupivacaine and that of pamoic acid were heat treated in the same manner respectively. Their X-ray powder diffraction and TG/DSC were tested respectively (FIG. 19), and the results are as shown in the table below.

| | | Bupivacaine:pamoic acid (1:1) | Bupivacaine:pamoic acid (2:1) | Bupivacaine:pamoic acid (4:1) | Bupivacaine | Pamoic acid |
|---|---|---|---|---|---|---|
| Physical mixture | X-ray powder diffraction | The diffraction peaks of two components were overlapped with each other | The diffraction peaks of two components were overlapped with each other | The diffraction peaks of two components were overlapped with each other | | |
| Co-crystal by melting | X-ray powder diffraction | The characteristic peaks of bupivacaine disappeared, and some of the characteristic peaks of pamoic acid remained | Amorphous form, without obvious characteristic peak | Amorphous form, without obvious characteristic peak | Waxy, undetected | Crystalline, without change in peaks |
| Physical mixture | TG/DSC | Bupivacaine peak was at 93.53 C.; pamoic acid peak was interfered, and has a gentle negative peak at 200 to 300 C.; and the integration was not accurate (about 260.97) | Bupivacaine peak was at 104.52 C.; pamoic acid peak was interfered, and has a gentle negative peak at 200 to 300 C.; and no integration could be carried out | Bupivacaine peak was at 106.34 C.; pamoic acid peak was interfered, and has a gentle negative peak at 200 to 300 C.; and no integration could be carried out | 105.98 C. | 326.83 C. (batch 20171208) |

-continued

|  | Bupivacaine:pamoic acid (1:1) | Bupivacaine:pamoic acid (2:1) | Bupivacaine:pamoic acid (4:1) | Bupivacaine | Pamoic acid |
|---|---|---|---|---|---|
| Co-crystal TG/DSC by melting | Bupivacaine has no endothermic peak; pamoic acid has a gentle negative peak at 200 to 300 C.; and no integration could be carried out | Bupivacaine has no endothermic peak; pamoic acid peak was interfered, and has a gentle negative peak at 200 to 300 C.; and no integration could be carried out | Bupivacaine has no endothermic peak; pamoic acid peak was interfered, and almost has no negative peak of endothermic peak; and no integration could be carried out | 99.61 C., (there was a small endothermic peak at 50.34 C.) | 326.04 (batch 20171208, dried) |

Figure 19:
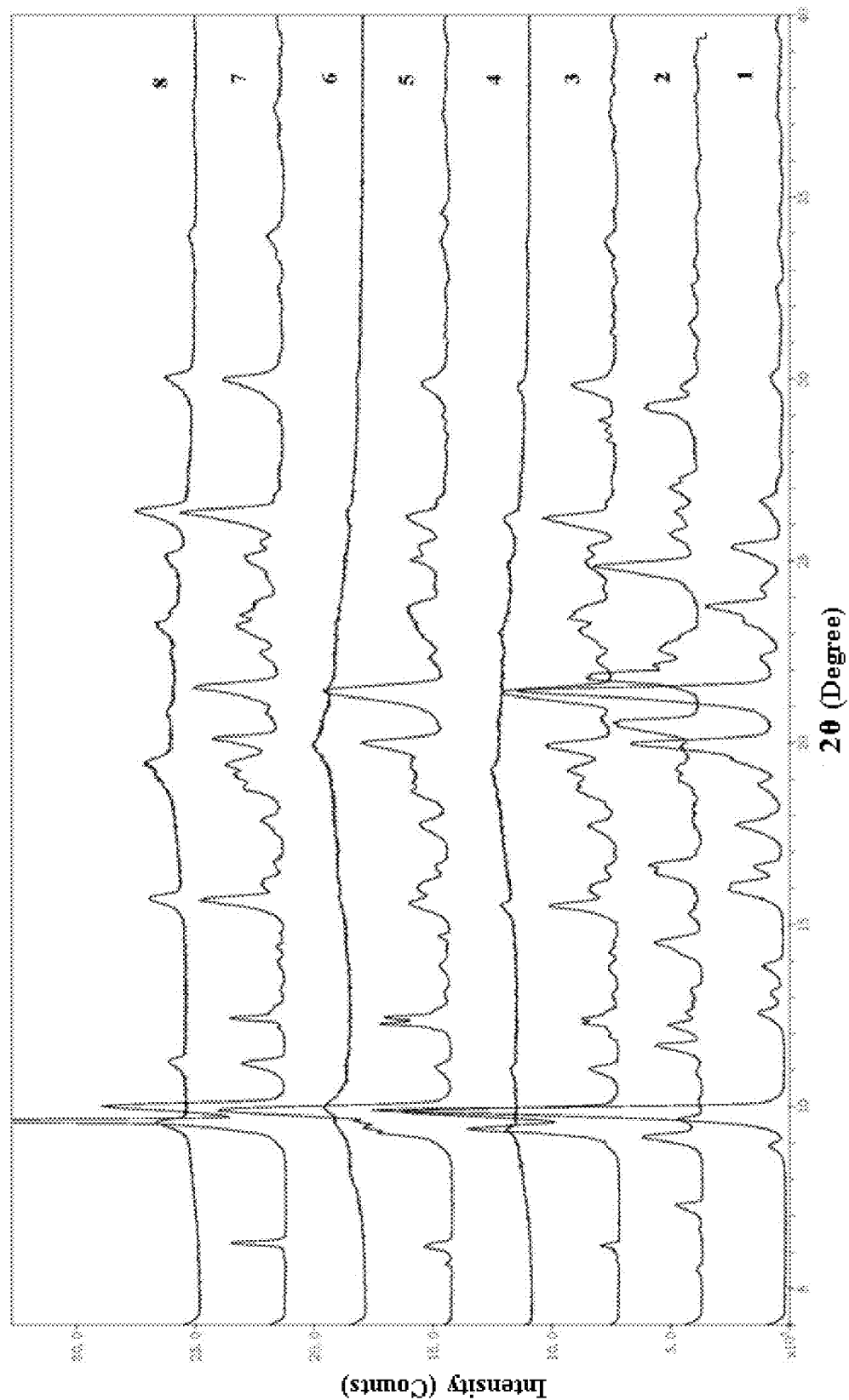
FIG. 19 is an X-ray powder diffraction pattern of 8 samples in Preparation Example 33, wherein the designations 1 to 8 from bottom to top represent bupivacaine, pamoic acid, a physical mixture of bupivacaine and pamoic acid (in a ratio of 2:1), a co-crystal of bupivacaine and pamoic acid (in a ratio of 2:1), a physical mixture of bupivacaine and pamoic acid (in a ratio of 4:1), a co-crystal of bupivacaine and pamoic acid (in a ratio of 4:1), a physical mixture of bupivacaine and pamoic acid (in a ratio of 1:1), and a co-crystal of bupivacaine and pamoic acid (in a ratio of 1:1), respectively.

It can be seen that there are several differences between the co-crystal and a single material or a physical mixture thereof. The X-ray powder diffraction pattern for the physical mixture equals to a simple addition of those of two single materials. In the TG/DSC diagram, bupivacaine has an endothermic peak, and the pamoic acid peak shifts to an earlier time. The reason may be that bupivacaine has been melted with time increasing in the test, which has a certain co-melting effect on pamoic acid before pamoic acid is melted, thereby affecting the melting peak of pamoic acid. The X-ray powder diffraction pattern for the melting co-crystal almost has no obvious diffraction peak (some of the characteristic peaks of pamoic acid remain for the 1:1 co-crystal), and the endothermic peak of bupivacaine substantially disappears in the TG/DSC diagram. FIG. 19 is an X-ray powder diffraction pattern of 8 samples, wherein the designations 1 to 8 from bottom to top represent bupivacaine, pamoic acid, a physical mixture of bupivacaine and pamoic acid (in a ratio of 2:1), a co-crystal of bupivacaine and pamoic acid (in a ratio of 2:1), a physical mixture of bupivacaine and pamoic acid (in a ratio of 4:1), a co-crystal of bupivacaine and pamoic acid (in a ratio of 4:1), a physical mixture of bupivacaine and pamoic acid (in a ratio of 1:1), and a co-crystal of bupivacaine and pamoic acid (in a ratio of 1:1), respectively.

Formulation Example 1

10 g of the compound of Preparation Example 10 and 20 g of mannitol were added in a 10 mmol/L sodium phosphate buffered solution (pH7.4), stirred appropriately for suspending, and homogenized with a Panda Plus 2000 homogenizer. The effects of the particle size of the raw materials by homogenization pressure and number of cycles were investigated. The volume was set to 100 mL, and the solution after treatment was a first suspension. The particle size was determined with a laser particle size analyzer (BT9300, Liaoning Dandong Bettersize Instrument Ltd.), and the results were as follows:

| Pressure and number of cycles | $D_{10}$ (μm) | $D_{50}$ (μm) | $D_{90}$ (μm) |
|---|---|---|---|
| untreated | 11.870 | 34.800 | 78.610 |
| 6 cycles at 800 bar | 0.892 | 4.244 | 8.767 |
| 2 cycles at 1200 bar | 0.932 | 3.028 | 6.922 |
| 4 cycles at 1200 bar | 0.776 | 2.770 | 6.108 |
| 6 cycles at 1200 bar | 0.610 | 1.343 | 6.579 |

Further, a long-acting suspension injection was prepared according to the table below:

|  | 1a | 1b |
|---|---|---|
| First suspension (1200 bar, 6 cycles, homogenization) | 100 mL | 100 mL |
| Sodium carboxymethyl cellulose (CMC 7L2P) | 1.5 g | 2 g |
| Tween-80 | 0.5 g | 1 g |
| Mannitol | 15 g | 20 g |
| 10 mmol/L sodium phosphate buffer (pH 7.4) | to 200 mL | to 200 mL |

Formulation Example 2

10 g of the compound of Preparation Example 12 and 20 g of mannitol were added in a 10 mmol/L sodium phosphate buffered solution (pH7.4), stirred appropriately for suspending, and homogenized with a Panda Plus 2000 homogenizer. The effects of the particle size of the raw materials by homogenization pressure and number of cycles were investigated. The volume was set to 100 mL, and the solution after treatment was a first suspension. The particle size was determined with a laser particle size analyzer (BT9300, Liaoning Dandong Bettersize Instrument Ltd.), and the results were as follows:

| Particle size | $D_{10}$ | $D_{50}$ | $D_{90}$ |
|---|---|---|---|
| untreated | 3.767 | 18.767 | 42.287 |
| 2 cycles at 400 bar | 1.990 | 8.306 | 17.280 |
| 4 cycles at 400 bar | 1.586 | 7.107 | 14.890 |
| 6 cycles at 400 bar | 1.524 | 4.885 | 11.199 |
| 2 cycles at 800 bar | 1.374 | 4.221 | 8.196 |
| 4 cycles at 800 bar | 1.218 | 4.088 | 8.107 |
| 6 cycles at 800 bar | 1.268 | 3.502 | 6.994 |
| 2 cycles at 1200 bar | 1.418 | 4.450 | 9.324 |
| 4 cycles at 1200 bar | 1.338 | 4.238 | 8.798 |
| 6 cycles at 1200 bar | 1.245 | 3.807 | 8.744 |

Further, a long-acting suspension infection was prepared according to the table below:

|  | 2a | 2b |
|---|---|---|
| First suspension (6 cycles, homogenization) | (1200 bar), 100 mL | (800 bar) 100 mL |
| Sodium carboxymethyl cellulose (CMC 7M31F PH) | 4 g | 0.5 g |
| Tween-80 | 1 g | 0.5 g |
| Mannitol | 20 g | 15 g |
| 10 mmol/L sodium phosphate buffer (pH 7.4) | to 200 mL | to 200 mL |

Formulation Example 3

10 g of the compound of Preparation Example 12 and 0.1 g of Tween-80 were added in a 10 mmol/L sodium phosphate buffered solution (pH 7.4) and diluted to 100 mL with the buffer solution, stirred for suspending, and homogenized with a Panda Plus 2000 homogenizer, this suspension was named "first suspension". The particle size of the compound after homogenization was as follows: $D_{10}$ was 1.18 μm, $D_{50}$ was 4.06 μm, and $D_{90}$ was 15.29 μm.

Further, a suspension was prepared according to the table below. The suspension was dispensed into vials in 10 mL per bottle, and lyophilized (LGJ-18S lyophilizer). 9 mL of water for injection was added for reconstruction and suspending before use.

| First suspension (1200 bar, 6 cycles, homogenization) | 100 mL |
|---|---|
| Sodium carboxymethyl cellulose (CMC 7M31F PH) | 1 g |
| Tween-80 | 0.4 g |
| Mannitol | 35 g |
| 10 mmol/L sodium phosphate buffer (pH 7.4) | to 200 mL |

Formulation Example 4

10 g of the compound of Preparation Example 12 and 0.5 g of Tween-80 were added in a 10 mmol/L sodium phosphate buffered solution (pH 7.4) and diluted to 100 mL with the buffer solution, stirred for suspending, and homogenated with a T18 digital homogenizer, this suspension was named "first suspension". The particle size of the compound after homogenization (measured for three times) was as follows: $D_{10}$ was between 3.70 and 4.08 μm, $D_{50}$ was between 13.28 and 16.80 μm, and $D_{90}$ was between 28.44 and 49.01 μm.

Further, a long-acting suspension injection was prepared according to the table below. The suspension was dispensed into vials in 10 mL per bottle, and lyophilized by using a LGJ-18S lyophilizer according to the lyophilization temperature increasing procedure as shown in the table below. 9 mL of water for injection was added for reconstruction and suspending before use.

| First suspension | 100 mL |
|---|---|
| Sodium carboxymethyl cellulose (CMC 7M31F PH) | 1 g |
| Tween-80 | 0.5 g |
| Mannitol | 35 g |
| 10 mmol/L sodium phosphate buffer (pH 7.4) | to 200 mL |

Lyophilization temperature increasing procedure:

|  | Temperature | Maintaining time |
|---|---|---|
| pre-freezing | −40° C. | 2 h |
| First drying | −20° C. | 2 h |
|  | −13° C. | 15 h |
| Second drying | −5° C. | 2 h |
|  | 5° C. | 2 h |
|  | 30° C. | 15 h |

Formulation Examples 5-7

10 g of the compound of Preparation Example 29 was pulverized with a jet mill (J-20 type jet mill, Tecnologia Meccanica Srl, Italy).

0.1 g of Tween-80, 0.6 g of sodium carboxymethyl cellulose, 5.0 g of mannitol, and 0.28 g of sodium dihydrogen phosphate dihydrate were added in 90 mL water, and stirred to dissolution, to obtain a matrix solution.

4.82 g of pulverized or unpulverized compound (Preparation Example 29) was added in 90 mL of the matrix solution, stirred to make a uniform suspension, adjusted to pH 6.5 to 7.5 with 1 mol/L sodium hydroxide, then diluted to 100 mL with water, and stirred for suspending, to obtain a long-acting suspension injection.

| Raw material | Formulation Example 5 | Formulation Example 6 | Formulation Example 7 |
|---|---|---|---|
| compound of Preparation Example 29 (HYR-PB21) | Prescribed amount (g) 4.82 | Prescribed amount (g) 4.82 | Prescribed amount (g) 4.82 |
| Treatment method | Jet milling | Jet milling | Unpulverized |
| Pulverization parameter: | Feeding pressure: 4 kg, Pulverization pressure: 4 kg, Rotation rate of feeder motor: 500 rpm | Feeding pressure: 3 kg, Pulverization pressure: 3 kg, Rotation rate of feeder motor: 500 rpm | — |
| Particle size $D_{10}$ (μm) | 0.997 | 1.689 | 5.314 |
| $D_{50}$ (μm) | 2.845 | 5.873 | 25.088 |
| $D_{90}$ (μm) | 5.963 | 11.466 | 70.305 |
| Excipients |  |  |  |
| Tween-80 | 0.10 | 0.10 | 0.10 |
| Sodium carboxymethyl cellulose (CMC 7M31F PH) | 0.60 | 0.60 | 0.60 |
| Mannitol | 5.00 | 5.00 | 5.00 |
| $NaH_2PO_4 \cdot 2H_2O$ | 0.28 | 0.28 | 0.28 |
| Sodium hydroxide | q.s. | q.s. | q.s. |
| Water | to 100 mL | to 100 mL | to 100 mL |
| pH | 7.06 | 7.04 | 7.05 |
| Needle passing ability | 0.45 mm | 0.45 mm | 0.7 mm |
| Content | 88.31% | 91.83% | 99.02% |
| Sample state | Suspension | Suspension | Suspension |

Formulation Examples 8-10

Figure 18:
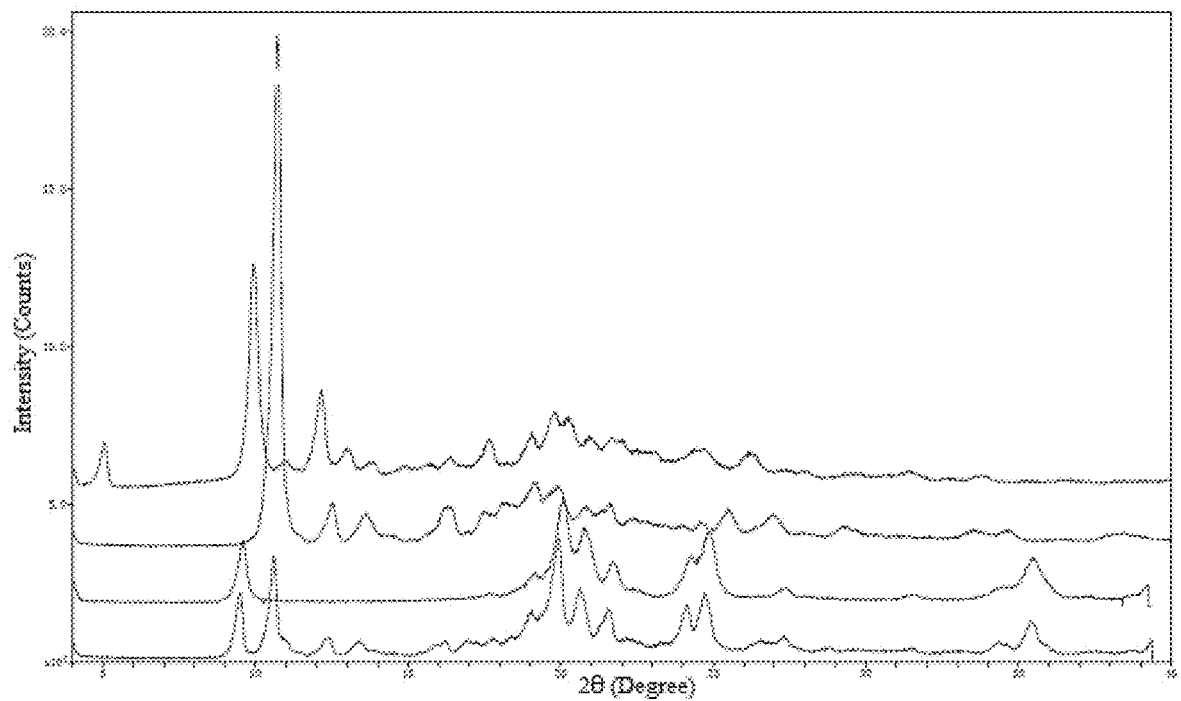
FIG. 18 shows a comparative powder diffraction pattern of the Formulation Examples, wherein the four diffraction curves are attributed to polymorph A, polymorph C, the excipient, and Formulation Example 11 from top to bottom respectively.

The compound of Preparation Example 29 was weighed in the amount as shown in the table below to prepare a first suspension and a second solution respectively. The first suspension was homogenized with a Panda Plus 2000 homogenizer, added the second solution in the first suspension-, and stirred to make a uniform suspension. The suspension was adjusted to pH 6.5 to 7.5 with 1 mol/L sodium hydroxide, and diluted to 1000 mL with water, mixed to make a uniform suspension. The blank excipient was formulated once in the second suspending manner. The suspension or blank excipient solution was filled into vials in 10 mL per bottle, and lyophilized according to the lyophilization procedure in Example 4. The lyophilization was tested and the results were as follows.

diffractions of the product and Preparation Example 11 (excipients blank) were determined. It was found from the comparison between them and an excipients blank sample, polymorph A and polymorph C (see FIG. 18 (four X-ray diffraction patterns are attributed to polymorph A, polymorph C, the excipients blank, and Formulation Example 11 from top to bottom respectively)) that the characteristic peak having a polymorph A at the diffraction angle of 4.9°/9.8°

|  |  | Formulation Example 8 | Formulation Example 9 | Formulation Example 10 |
|---|---|---|---|---|
| Strength (stated amount of bupivacaine) | | 100 mg | 300 mg | Excipient blank |
| Raw material | | Prescribed amount (g) | Prescribed amount (g) | Formulated once and unhomogenized |
| First suspension | compound of Preparation Example 29 (HYR-PB21) | 17.36 | 52.09 | — |
|  | Tween-80 | 1.0 | 1.0 | 1.0 |
|  | Mannitol | 20 | 20 | — |
|  | Water | 150 | 150 | — |
| Second solution | Sodium carboxymethyl cellulose (CMC 7M31F PH) | 6.0 | 6.0 | 6.0 |
|  | Mannitol | 25.0 | 25.0 | 45.0 |
|  | Sodium dihydrogen phosphate (dihydrate) | 1.56 | 1.56 | 1.56 |
|  | Water | 800 | 800 | 900 |
| Sodium hydroxide | | S.q | S.q | S.q |
| Water | | to 1000 mL | to 1000 mL | to 1000 mL |
| Tested after lyophilization | | | | |
| Quality properties | pH | 7.15 | 7.25 | 6.80 |
|  | Needle passing ability | Passing through a φ0.5 mm needle | Passing through a φ0.5 mm needle | — |
|  | Content | 93.02% | 98.30% | — |
|  | Sample state | Pale yellow mass | Pale yellow mass | White mass |
|  | Water content | 2.47% | 1.52% | 2.98% |
|  | Reconstruction time | 30 seconds | 40 seconds | 40 seconds |
| Particle size distribution | $D_{10}$ (μm) | 0.850 | 0.825 | — |
|  | $D_{50}$ (μm) | 2.232 | 2.050 | — |
|  | $D_{90}$ (μm) | 4.447 | 3.917 | — |

Formulation Example 11

10 g of the compound of Preparation Example 16 was added in 30 mL water, stirred for suspending, and homogenized with a Panda Plus 2000 homogenizer (1000 bar, 3 cycles). The particle size was determined with a laser particle size analyzer (BT9300, Liaoning Dandong Bettersize Instrument Ltd.), and $D_{10}$, $D_{50}$ and $D_{90}$ were 0.923, 3.887 and 8.025 μm respectively. This suspension was named "first suspension". Further, a long-acting suspension injection was prepared according to the table below:

| First suspension (1000 bar, 3 cycles, homogenization) | As described above |
|---|---|
| Sodium carboxymethyl cellulose (CMC 7M31F PH) | 1.2 g |
| Tween-80 | 0.2 g |
| Mannitol | 9 g |
| $NaH_2PO_4 \cdot 2H_2O$ | 0.312 g |
| 10 mmol/L sodium phosphate buffer (pH 7.4) | to 200 mL |

The above suspension was lyophilized according to the lyophilization procedure in Example 4. The powder X-ray substantially disappeared, while the characteristic peak having a polymorph C (10.8°/12.6°) was obvious, indicating that polymorph A was converted into polymorph C during the suspension preparation and the lyophilization.

Formulation Example 12

2.17 g of the compound of Preparation Example 30, 0.045 g of Tween-80, and 2.25 g of mannitol were added in 15 mL water and mixed uniformly. Zirconia pellets were added thereto, and the mixture was milled with a ball mill (puiverisette 7 ball mill, PRITSCH). The parameters for ball milling were as follows: rotation rate: 1200 rpm, time: 3 min, interval time: 15 min, and number of cycles: 10. A first suspension was obtained. The particle size of the compound after ball milling was as follows: $D_{10}$ was 2.050 μm, $D_{50}$ was 6.795 9 μm, and $D_{90}$ was 12.480 μm.

1.0 g of sodium carboxymethyl cellulose (CMC 7MF PH) and 0.128 g of sodium dihydrogen phosphate were added in 27 mL water, stirred to dissolution, mixed with the ball milled first suspension, stirred for uniformly suspending, adjusted to pH 6.5 to 7.5 with 1 mol/L sodium hydroxide, then diluted to 45 mL with water, and stirred for suspending, to obtain a long-acting suspension injection.

Formulation Example 13

100 g of the compound of Preparation Example 29 was pulverized with a jet mill (J-20 type jet mill, Tecnologia Meccanica Srl, Italy). The parameters for pulverization were as follows: feeding pressure: 4 kg, pulverization pressure: 4 kg, and feeder motor rotation rate: 500 rpm. The particle size after pulverization was as follows: $D_{10}$=1.125 µm, $D_{50}$=3.017 µm, $D_{90}$=6.224 µm.

0.1 g of Tween-80, 1.0 g of sodium carboxymethyl cellulose (7L2P), 2.5 g of mannitol, 2.0 g of polyethylene glycol 400, and 0.28 g of sodium dihydrogen phosphate dihydrate were placed into 100 mL water, stirred to dissolution, and adjusted to pH 6.5 to 7.5 with 1 mol/L sodium hydroxide, to obtain a dedicated solvent.

0.174 g of pulverized or unpulverized compound and 10 mL of the dedicated solvent were filled into a package container respectively, and formulated immediately before use, to prepare a long-acting suspension injection.

Formulation Example 14

100 g of the compound of Preparation Example 29 was pulverized with a jet mill (J-20 type jet mill, Tecnologia Meccanica Srl, Italy). The parameters for pulverization were as follows: feeding pressure: 4 kg, pulverization pressure: 4 kg, and feeder motor rotation rate: 500 rpm. The particle size after pulverization was as follows: $D_{10}$=1.125 µm, $D_{50}$=3.017 µm, $D_{90}$=6.224 µm.

0.1 g of propylene glycol, 1.0 g of sodium carboxymethyl cellulose (7L2P), 2.0 g of polyethylene glycol 400, and 0.16 g of sodium dihydrogen phosphate dihydrate were placed into 100 mL water, stirred to dissolution, and adjusted to pH 6.5 to 7.5 with 1 mol/L sodium hydroxide, to obtain a dedicated solvent.

0.174 g of pulverized or unpulverized compound was mixed with 2.5 g of mannitol to obtain solid powders. 0.314 g of the mixed solid powders and 10 mL of the dedicated solvent were filled into a package container respectively, and formulated immediately before use, to prepare a long-acting suspension injection.

Tests on the Properties of the Compound

In the present application, the insoluble complex represented by formula (I) or a solvate thereof and a formulation thereof according to the present invention were tested for the in vitro solubility, dissolution, systemic pharmacokinetics in animal body, and the like.

Test Example 1

Test on the Solubility in a Simulated Body Fluid

Figure 10A:
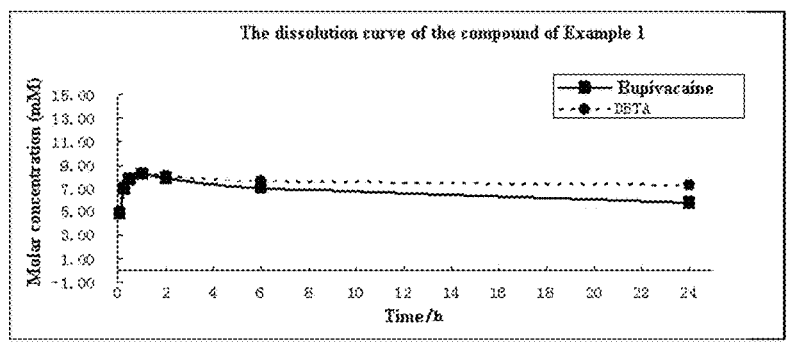
FIGS. 10a-10c show dissolution curve graphs of the compounds of the Preparation Examples in PBS.
Figure 10A:
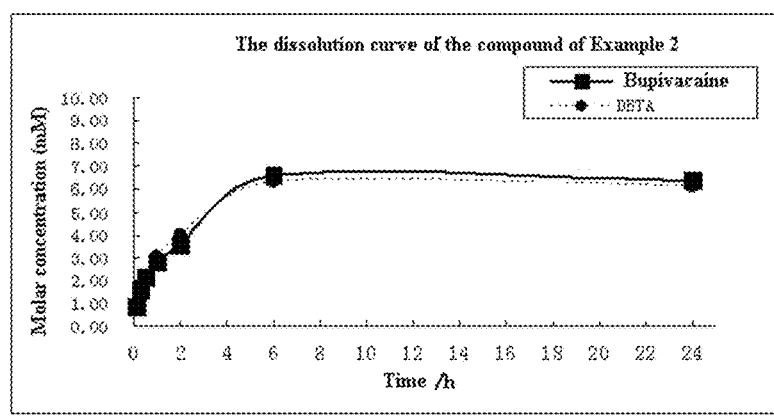
Figure 10A:
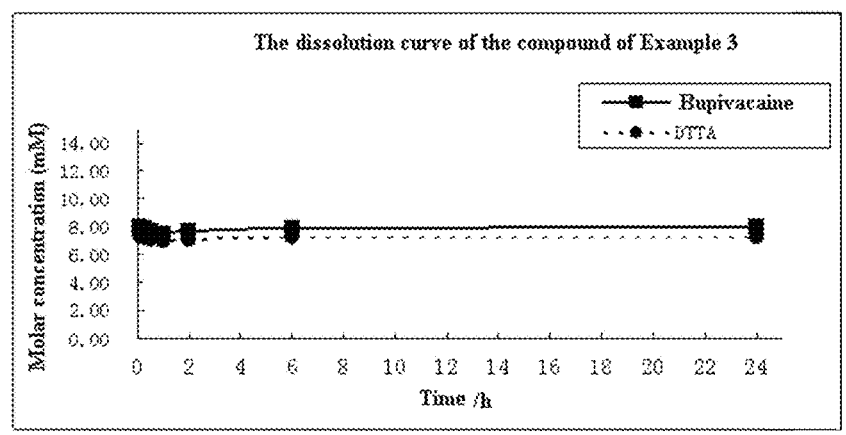
Figure 10A:
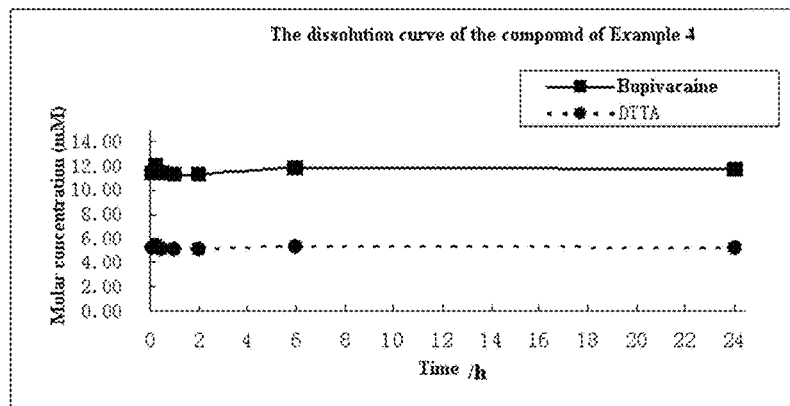
Figure 10B:
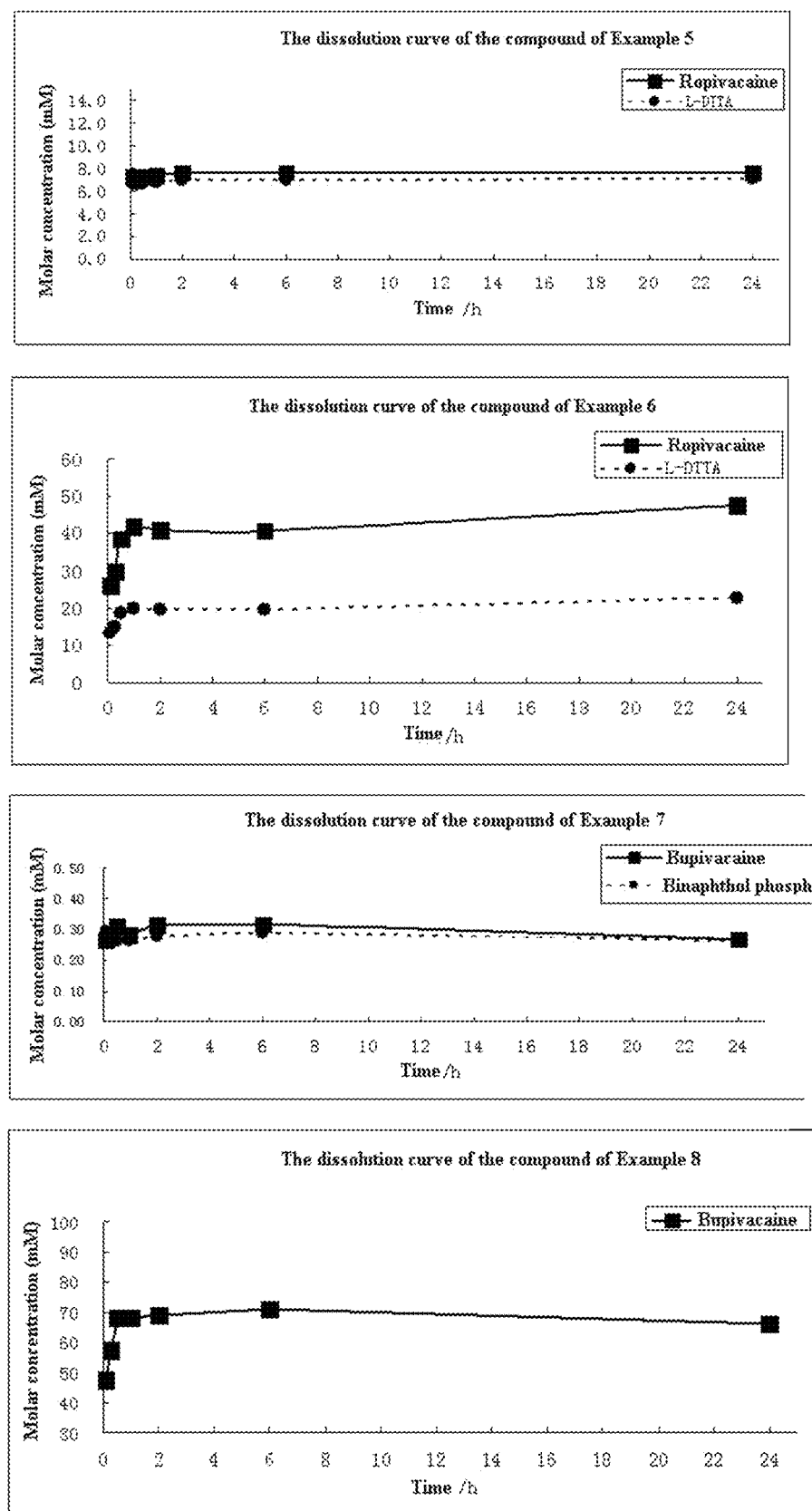
Figure 10C:
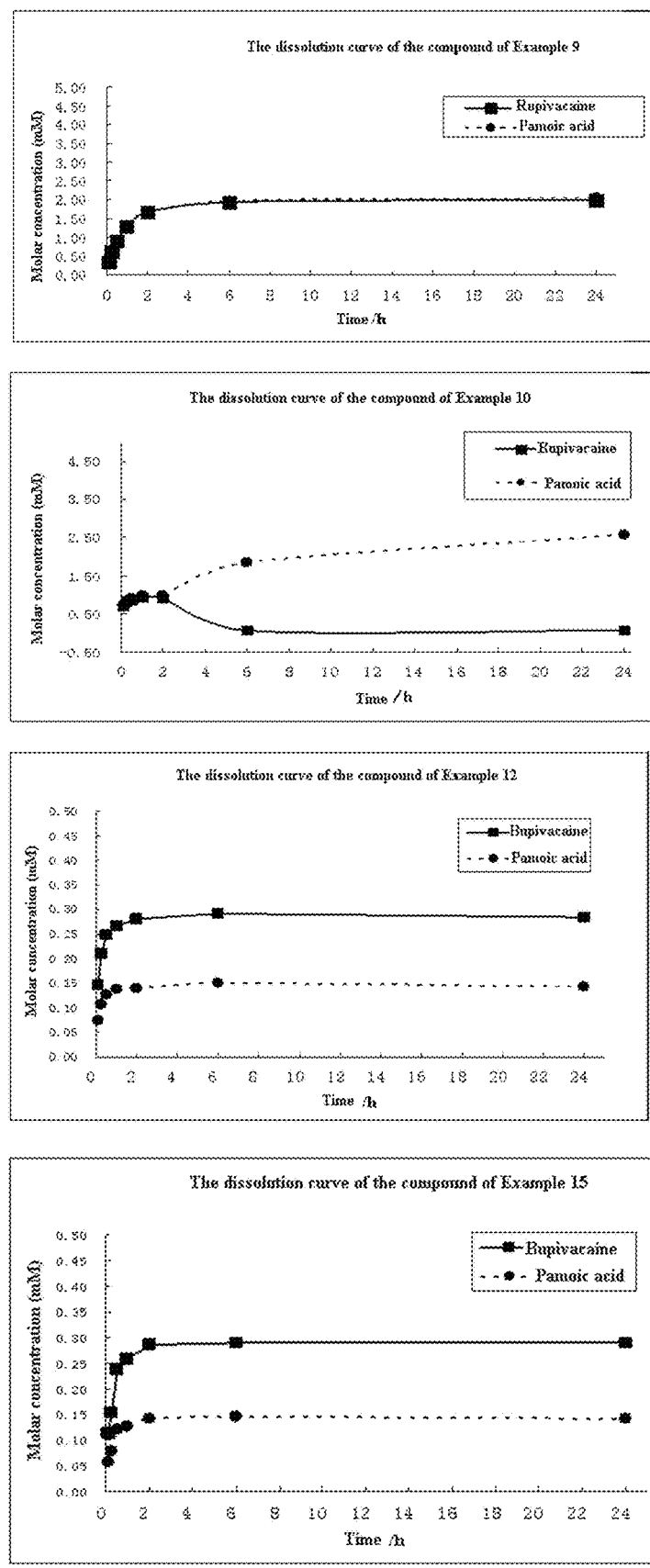

About 200 mg of solid powders of the example was suspended in a 50 mL phosphate buffered saline at pH 7.4 (0.01 M PBS, containing 8 mM $Na_2HPO_4$, 2 mM $KH_2PO_4$, 136 mM NaCl, and 2.6 mM KCl), and stirred at 37° C. for 24 hours. Appropriate amounts of the suspension were taken out at 5 min, 15 min, 30 min, 1 h, 2 h, 6 h, and 24 h respectively, quickly filtered, and diluted with methanol by a factor of two. The concentration of the drug dissolved in the PBS buffered solution was determined with an HPLC-a method. The results for the compounds of the Preparation Examples are as shown in the table below (table 1) and FIG. 10a-c.

TABLE 1

Data for the solubility of the compounds of the examples in a simulated body fluid

| Compound concentration (mM) | 5 min | 15 min | 30 min | 1 h | 2 h | 6 h | 24 h | |
|---|---|---|---|---|---|---|---|---|
| Bupivacaine free base | Saturated solubility: 1.45 mM | | | | | | | |
| Ropivacaine free base | Saturated solubility: 1.36 mM | | | | | | | |
| Preparation Example 1 | 4.8846 | 6.9872 | 7.7552 | 8.1960 | 7.9117 | 7.0061 | 5.7679 | Bupivacaine DBTA |
| | 4.9920 | 7.1077 | 8.6666 | 8.2846 | 8.0155 | 7.5905 | 7.3037 | |
| Preparation Example 2 | 0.8190 | 1.5937 | 2.1332 | 2.8487 | 3.5654 | 6.5770 | 6.3896 | Bupivacaine DBTA |
| | 0.7696 | 1.5504 | 2.1838 | 3.0359 | 3.9533 | 6.3363 | 6.1227 | |
| Preparation Example 3 | 7.9476 | 7.8626 | 7.6622 | 7.5190 | 7.7193 | 7.8832 | 7.9178 | Bupivacaine DTTA |
| | 7.3163 | 7.2446 | 7.0122 | 6.9006 | 7.0481 | 7.2117 | 7.2490 | |
| Preparation Example 4 | 11.3894 | 12.0091 | 11.4269 | 11.2567 | 11.2781 | 11.8518 | 11.6933 | Bupivacaine DTTA |
| | 5.1610 | 5.3995 | 5.1350 | 5.0848 | 5.0683 | 5.3120 | 5.2197 | |
| Preparation Example 5 | 7.2687 | 7.2155 | 7.2872 | 7.3437 | 7.6304 | 7.6041 | 7.6489 | Ropivacaine DTTA |
| | 6.6768 | 6.6128 | 6.7040 | 6.7521 | 6.9880 | 6.9718 | 7.0738 | |
| Preparation Example 6 | 26.0585 | 29.8888 | 38.6576 | 41.9836 | 41.0111 | 40.7778 | 47.4453 | Ropivacaine DTTA |
| | 13.3808 | 15.0173 | 18.5864 | 19.9901 | 19.6790 | 19.6172 | 22.8439 | |
| Preparation Example 7 | 0.2630 | 0.2714 | 0.3105 | 0.2807 | 0.3148 | 0.3177 | 0.2684 | Bupivacaine naphthol phosphate |
| | 0.2935 | 0.2756 | 0.2643 | 0.2633 | 0.2789 | 0.2884 | 0.2646 | |
| Preparation Example 8 | 47.6783 | 57.1254 | 68.3149 | 68.1958 | 68.9026 | 71.2539 | 66.0200 | Bupivacaine Camphorsulonic acid |
| | — | — | — | — | — | — | — | |
| Preparation Example 9 | 0.3479 | 0.6026 | 0.8870 | 1.2856 | 1.6608 | 1.9440 | 1.9720 | Ropivacaine Pamoic acid |
| | 0.3459 | 0.6015 | 0.8803 | 1.2808 | 1.6684 | 1.9539 | 2.0523 | |
| Preparation Example 10 | 0.7220 | 0.8330 | 0.8859 | 0.9387 | 0.9097 | 0.0833 | 0.0670 | Bupivacaine Pamoic acid |
| | 0.7427 | 0.8579 | 0.9168 | 0.9816 | 0.9957 | 1.8673 | 2.5605 | |
| Preparation Example 12 | 0.1475 | 0.2101 | 0.2474 | 0.2672 | 0.2802 | 0.2908 | 0.2848 | Bupivacaine Pamoic acid |
| | 0.0736 | 0.1070 | 0.1274 | 0.1375 | 0.1400 | 0.1497 | 0.1429 | |
| Preparation Example 15 | 0.1128 | 0.1538 | 0.2394 | 0.2574 | 0.2875 | 0.2901 | 0.2903 | Bupivacaine Pamoic acid |
| | 0.0572 | 0.0779 | 0.1202 | 0.1278 | 0.1415 | 0.1467 | 0.1430 | |
| Preparation Example 29 | 0.1598 | 0.1969 | 0.2415 | 0.2699 | 0.2713 | 0.2751 | 0.3050 | Bupivacaine Pamoic acid |
| | 0.0782 | 0.0973 | 0.1221 | 0.1195 | 0.1400 | 0.1450 | 0.1516 | |
| Preparation Example 30 | 0.1423 | 0.2188 | 0.2337 | 0.2805 | 0.2773 | 0.2872 | 0.2869 | Bupivacaine Pamoic acid |
| | 0.0757 | 0.1116 | 0.1285 | 0.1356 | 0.1308 | 0.1379 | 0.1402 | |

Conclusion:

It can be seen from the results that since different insoluble salts have different solubility, and the solubility of most salts is larger than that of the free base, so the preparation of the insoluble salts cannot be determined by reasoning from conventional technology, and the ratio between the acid radical and the basic group in the suspension is not stable for some of the insoluble salts in a simulated body fluid, which cannot be predicted from any technology and principle. In comparison, the compound of Preparation Example 7 (naphthol phosphate, about 0.3 mM), the compound of Preparation Example 9 (ropivacaine pamoate, about 2.0 mM) and the compounds of Examples 12, 15, 29 and 30 (bis(bupivacaine) pamoate, about 0.3 mM) have a very low solubility, and the suspensions thereof are stable.

Test Example 2

A good insoluble salt also should have a stable dissolution property at different pH values.

Test on the Solubility in Media at Different pH

About 200 mg of solid powders of Preparation Example 10 and Preparation Example 15 were added in a 500 mL phosphate buffered solution at different pH values (50 mmol/L, pH 5.5, pH 6.5, pH 7.4, and pH 8.0) respectively, placed into a dissolution tester, kept at a constant temperature of 37° C., and paddle stirred at 50 rpm for 72 hours. Appropriate amounts of the suspension were taken out at 15 min, 30 min, 45 min, 1 h, 2 h, 4 h, 6 h, 8 h, 24 h, 32 h, 48 h, and 72 h respectively, and centrifuged immediately (15000 rpm, 5 min). The supernatant was diluted with methanol by a factor of two. The concentration of the drug dissolved in the PB buffer solution was determined with an HPLC-b method. The results of the solubility of the examples are as shown in the table below:

The solubility table of mono(bupivacaine) pamoate (in a ratio of 1:1)

| Molar concentration (mmol/L) of Compound of Preparation Example 10 | | pH 5.5 | | pH 6.5 | | pH 7.4 | | pH 8.0 | |
|---|---|---|---|---|---|---|---|---|---|
| | | Bupivacaine | Pamoic acid | Bupivacaine | Pamoic acid | Bupivacaine | Pamoic acid | Bupivacaine | Pamoic acid |
| Time/h | 0.25 | 0.047 | 0.046 | 0.05 | 0.053 | 0.0555 | 0.0605 | 0.0575 | 0.063 |
| | 0.5 | 0.078 | 0.076 | 0.084 | 0.09 | 0.095 | 0.105 | 0.099 | 0.110 |
| | 0.75 | 0.106 | 0.103 | 0.115 | 0.124 | 0.1315 | 0.1465 | 0.1375 | 0.154 |
| | 1 | 0.136 | 0.132 | 0.148 | 0.160 | 0.170 | 0.190 | 0.178 | 0.200 |
| | 2 | 0.188 | 0.182 | 0.274 | 0.296 | 0.288 | 0.320 | 0.308 | 0.344 |
| | 4 | 0.222 | 0.218 | 0.384 | 0.414 | 0.386 | 0.430 | 0.416 | 0.468 |
| | 6 | 0.234 | 0.232 | 0.396 | 0.424 | 0.428 | 0.476 | 0.494 | 0.554 |
| | 8 | 0.234 | 0.23 | 0.404 | 0.448 | 0.440 | 0.486 | 0.558 | 0.624 |
| | 24 | 0.246 | 0.244 | 0.186 | 0.440 | 0.426 | 0.550 | 0.610 | 0.688 |
| | 32 | 0.248 | 0.248 | 0.15 | 0.426 | 0.402 | 0.592 | 0.622 | 0.702 |
| | 48 | 0.198 | 0.236 | 0.14 | 0.428 | 0.204 | 0.498 | 0.592 | 0.694 |
| | 72 | 0.142 | 0.224 | 0.128 | 0.416 | 0.166 | 0.458 | 0.44 | 0.7 |

The solubility table of bis(bupivacaine) pamoate (in a ratio of 2:1)

| Molar concentration (mmol/L) of Compound of Preparation Example 15 | | pH 5.5 | | pH 6.5 | | pH 7.4 | | pH 8.0 | |
|---|---|---|---|---|---|---|---|---|---|
| | | Bupivacaine | Pamoic acid | Bupivacaine | Pamoic acid | Bupivacaine | Pamoic acid | Bupivacaine | Pamoic acid |
| Time/h | 0.25 | 0.050 | 0.020 | 0.046 | 0.024 | 0.038 | 0.020 | 0.036 | 0.020 |
| | 0.5 | 0.070 | 0.034 | 0.076 | 0.038 | 0.080 | 0.042 | 0.092 | 0.050 |
| | 0.75 | 0.140 | 0.070 | 0.138 | 0.076 | 0.192 | 0.100 | 0.252 | 0.138 |
| | 1 | 0.196 | 0.092 | 0.202 | 0.106 | 0.240 | 0.134 | 0.328 | 0.182 |
| | 2 | 0.198 | 0.094 | 0.204 | 0.108 | 0.246 | 0.134 | 0.336 | 0.186 |
| | 4 | 0.198 | 0.092 | 0.202 | 0.106 | 0.242 | 0.134 | 0.338 | 0.192 |
| | 6 | 0.198 | 0.094 | 0.198 | 0.104 | 0.234 | 0.13 | 0.338 | 0.190 |
| | 8 | 0.198 | 0.092 | 0.198 | 0.106 | 0.232 | 0.128 | 0.334 | 0.186 |
| | 24 | 0.192 | 0.088 | 0.198 | 0.106 | 0.226 | 0.124 | 0.326 | 0.182 |
| | 32 | 0.196 | 0.092 | 0.202 | 0.106 | 0.226 | 0.124 | 0.328 | 0.186 |
| | 48 | 0.198 | 0.092 | 0.200 | 0.106 | 0.230 | 0.126 | 0.336 | 0.186 |
| | 72 | 0.190 | 0.084 | 0.196 | 0.100 | 0.224 | 0.120 | 0.336 | 0.184 |

Conclusion:

The molar ratios of the solubility of the salt comprised of bupivacaine and pamoic acid in a molar ratio of 1:1 (the compound of Preparation Example 10) in the media at pH 5.5, pH 7.4, and pH 8.0 remained around 1.0 for 48 hours or less, while the molar ratio in the medium at pH 6.5 only remained for 8 hours, and decreased after a longer time, during which the concentration of bupivacaine decreased and the concentration of pamoic acid increased, that is, the acid and the base were separated from each other. However, the molar ratios of the solubility of the salt comprised of bupivacaine and pamoic acid in a molar ratio of 2:1 (the compound of Preparation Example 15) in the media at pH 5.5, pH 6.5, pH 7.4, and pH 8.0 remained around 2.0 for at least 72 hours, and the concentrations of bupivacaine and pamoic acid did not change substantially, that is, the acid and the base would not be separated from each other.

Test Example 3

Test on the Dissolution of the Injection

A chromatographic column (150*4.6 mm) was washed to remove the filler, serving as a flow through cell. 1.5 mL of samples obtained by redissolving Preparation Examples 3, 4, 6 and 8 were injected into the column. Two ends of the column were screwed tightly. The column was eluted with a high performance liquid phase. The elution medium was an aqueous solution of 1% Tween-80 and 10 mmol/L PBS. The elution flow rate was controlled to be 0.5 mL/min. The eluents were collected at 1 h, 2 h, 3 h, 4 h, 21 h, 27 h, 44 h, 51 h, and 69 h respectively, and diluted with methanol by a factor of two, and shaken up, to serve as a test sample solution. An appropriate amount of bupivacaine control sample was weighed precisely, supplemented with methanol for dissolution, and diluted to a metered volume, to prepare a solution containing 500 μg of bupivacaine per 1 mL as a control stock solution. The control stock solution was diluted to a control solution of 50 μg/mL. 20 μL of each of the control solution and the test sample solution was metered precisely and injected into a liquid chromatograph respectively. The chromatogram was recorded. The results were calculated from the peak area with an external standard method.

The results of the release rate of Preparation Examples 3, 4, 6 and 8 are as shown in the table below:

| Release rate (%) | 0 | 0.5 h | 1 h | 2 h | 4 h | 20 h | 24 h | 30 h | 51 h | 69 h |
|---|---|---|---|---|---|---|---|---|---|---|
| Formulation Example 3 | 0 | 23.9 | 42.6 | 55.1 | 67.7 | 86.7 | 88.7 | 92.0 | 93.2 | 97.2 |
| Formulation Example 4 | 0 | 15.0 | 21.0 | 27.0 | 32.6 | 59.3 | 64.2 | 70.1 | — | — |
| Formulation Example 6 | 0 | 20.2 | 35.4 | 50.0 | 59.7 | 77.7 | 85.4 | 89.3 | | |
| Formulation Example 8 | 0 | 31.3. | 50.4 | 63.3 | 75.5 | 94.0 | 95.2 | | | |

Test Example 4

Systemic Pharmacokinetic Study of a bis(bupivacaine) pamoate Suspension After a Single Subcutaneously Injection at Three Points in a Hind Limb in SD Rats The systemic absorption and exposure of bis(bupivacaine) pamoate in a rat body was further evaluated by performing a systemic pharmacokinetic research on SD rats which were subcutaneously injected with a bis(bupivacaine) pamoate suspension (Formulation Example 3) once at three points in a left hind limb and comparing with a commercial bupivacaine hydrochloride injection. The long-acting sustained release feature of bis(bupivacaine) pamoate was verified by comparing the pharmacokinetic parameters of bis(bupivacaine) pamoate with a commercial formulation.

In the example, 20 healthy SD male rats (Beijing Vital River Laboratory Animal Technology Co., Ltd., 190 to 210 g) were chosen and randomly divided into 2 groups, i.e., a group for Formulation Example 3 and a group for the commercial bupivacaine hydrochloride injection (Wuhu Kangqi Pharmaceutical Co., Ltd.) group, with 10 animals in each group. Detailed administration regimen is as shown in the table below:

TABLE 2

The administration regimen for pharmacokinetic comparison research on SD rats which are subcutaneously injected with a bis(bupivacaine) pamoate suspension

| Group | Method and frequency of administration | Dosage (mg/kg) | Number of animal |
|---|---|---|---|
| Group for formulation Example 3 (suspension) | Subcutaneous injection (single) | 15 | 10 |
| Bupivacaine hydrochloride injection | Subcutaneous injection (single) | 5 | 10 |

About 0.5 mL of venous blood was collected at 30 min, 1 h, 2 h, 6 h, 8 h, 24 h, 48 h, 72 h and 96 h respectively after administration for both groups of laboratory animals for determining the blood drug concentration of bupivacaine.

Figure 11:
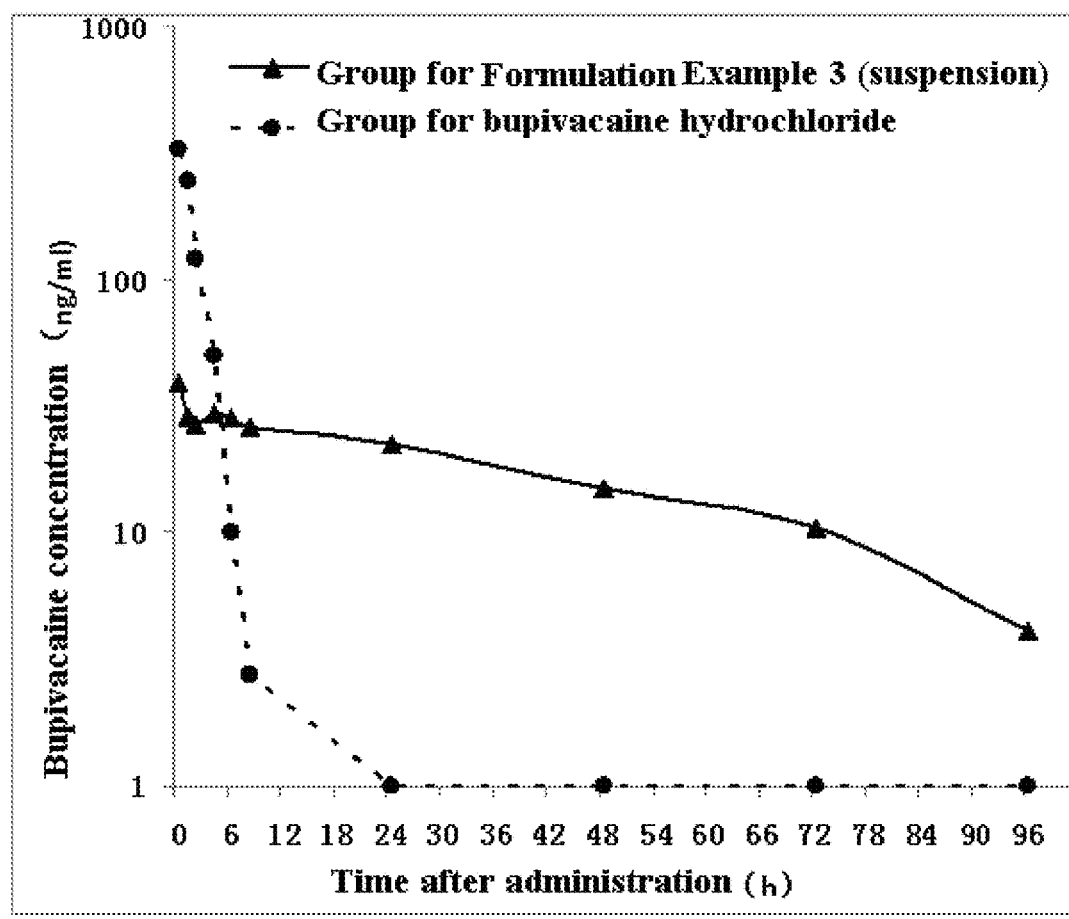
FIG. 11 shows a drug concentration-time curve of a comparison research on SD rats which are subcutaneously injected with a bis(bupivacaine) pamoate suspension and bupivacaine hydrochloride respectively once at three points in left hind limb.

The blood drug concentration-time curve and pharmacokinetic parameters for the group for Formulation Example 3 (suspension) and the group for commercial bupivacaine hydrochloride injection are as shown in FIG. 11 and table 3, respectively. In comparison with the group for commercial formulation (5 mg/kg), the $C_{max}$ value of triple dosages of bis(bupivacaine) pamoate suspension injection (15 mg/kg) was only about 12% of that of the group for commercial formulation, while the half life was as long as 32 hours, more than 30 times longer than that of the group for commercial formulation, and the AUC calculated with respect to the dosage was only 70% of that of the commercial formulation. The average blood drug concentration of the group for Formulation Example 3 (suspension) was more than that of the group for bupivacaine hydrochloride at 6 hours after administration, and the blood drug concentration even at 72 hours after administration was still more than that of the group for bupivacaine hydrochloride at the time point of 6 hours.

The results of the present study indicated that the bis(bupivacaine) pamoate solid suspension formulation has the pharmacokinetic advantages as a sustained-release formulation for the long-acting local postsurgical analgesic development.

TABLE 3

Main pharmacokinetic parameters of the comparison research on SD rats which are subcutaneously injected with a bis(bupivacaine) pamoate suspension and bupivacaine hydrochloride respectively once at three points in left hind limb

| Group | $AUC_{0-t}$ (ng/mL*h) | $C_{max}$ (ng/mL) | $T_{max}$ (h) | $T_{1/2}$ (h) |
|---|---|---|---|---|
| Group for formulation Example 3 (Suspension) | 1496.3 ± 132.1 | 36.2 ± 2.3 | 0.63 ± 0.2 | 32.2 ± 2.4 |
| Group for bupivacaine hydrochloride | 711.1 ± 75.3 | 329.6 ± 39.1 | 0.63 ± 02 | 1.0 ± 0.3 |

Test Example 5

Test on the Needle Passing Ability of the Injection

The needle passing ability of the example formulation was investigated with different types of syringe needles. The needle passing ability was investigated by drawing the suspension injection with a larger needle, fitting 18-22 G needle, and injecting the suspension injection by pushing it through the 18-22 G needles. The results showed that all the suspension injections were suitable for injection.

Scores were evaluated according to the following rating system.

| Score | Result |
|---|---|
| 0 | Blocked |
| 1 | Passing through a 18G needle (with an inner diameter of 0.9 mm) |
| 2 | Passing through a 19G needle (with an inner diameter of 0.7 mm) |
| 3 | Passing through a 20G needle (with an inner diameter of 0.6 mm) |
| 4 | Passing through a 21G needle (with an inner diameter of 0.5 mm) |
| 5 | Passing through a 22G needle (with an inner diameter of 0.4 mm) |

The investigation results are as follows:

| | Formulation Example 1a | Formulation Example 1b | Formulation Example 2a | Formulation Example 2b | Formulation Example 3 | Formulation Example 4 |
|---|---|---|---|---|---|---|
| Score | 5 | 2 | 4 | 4 | 5 | 3 |

Test Example 6

The Effect of the Injection Dosage and the Particle Size on the Rat Pharmacokinetics 15 healthy SD male rats (Beijing Vital River Laboratory Animal Technology Co., Ltd., 190 to 210 g) were chosen and divided into 5 groups, with 3 animals in each group. The drug of each Formulation Example was subcutaneously injected in a single dosage once at multiple points (3 points). About 0.5 mL of venous blood was collected at 5 min, 30 min, 1 h, 2 h, 4 h, 6 h, 8 h, 24 h, 48 h, 72 h, and 96 h respectively after administration for determining the blood drug concentration of bupivacaine. The detail information of group, administration regimen, and pharmacokinetic parameters are summarized as follows.

| Group | Group 17A (20 mg/kg) | Group 17B (40 mg/kg) | Group 17C (60 mg/kg) | Group 18 (20 mg/kg) | Group 19 (20 mg/kg) |
|---|---|---|---|---|---|
| Administration | Formulation Example 5 | | | Formulation Example 6 | Formulation Example 7 |
| Particle size $D_{50}$ (μm) | 2.845 | | | 5.873 | 25.088 |
| Time (h) | Blood drug level (ng/mL) | | | | |
| 0.083 | 20.258 | 36.224 | 38.012 | 16.271 | 12.749 |
| 0.5 | 51.296 | 86.249 | 84.761 | 36.075 | 23.761 |
| 1 | 53.705 | 71.847 | 93.665 | 37.707 | 26.668 |
| 2 | 42.89 | 47.841 | 89.415 | 37.868 | 27.97 |
| 4 | 53.908 | 60.683 | 102.787 | 52.39 | 39.204 |
| 6 | 97.798 | 106.777 | 168.019 | 64.722 | 47.734 |
| 8 | 79.585 | 120.815 | 170.296 | 72.501 | 42.648 |
| 24 | 43.069 | 69.681 | 126.884 | 43.545 | 24.552 |
| 48 | 21.628 | 35.42 | 65.019 | 21.055 | 14.999 |
| 72 | 9.333 | 17.16 | 32.632 | 11.156 | 11.679 |
| 96 | 5.378 | 13.147 | 18.626 | 7.251 | 7.554 |

-continued

| Pharmacokinetic parameter | | | | | |
|---|---|---|---|---|---|
| AUC(0-t) | 2821.85 | 4409.805 | 7431.822 | 2723.385 | 1855.703 |
| AUC(0-∞) | 2966.329 | 4707.339 | 7951.607 | 2990.26 | 2322.823 |
| MRT(0-t) | 26.744 | 29.466 | 30.781 | 30.448 | 33.38 |
| t1/2z | 21.21 | 23.969 | 23.062 | 27.642 | 43.217 |
| Tmax | 6 | 7.333 | 6.667 | 8 | 6.667 |
| Cmax | 97.798 | 134.091 | 175.224 | 72.501 | 48.847 |

The results indicated that all of the particle sizes and each of the dosages had obviously sustained-release pharmacokinetic characteristics, AUCs were substantially in a dose-response linear relationship. However, the linear relationship for $C_{max}$ was weaker, that is, the blood drug concentration was more stable, avoiding the adverse effect due to excessive high blood drug concentration at a large dosage. Additionally, $t_{1/2}$ prolonged along with the particle size increased, and the time of sustained release and the time of maintaining the analgesic efficacy could be controlled by adjusting the particle size.

Test Example 7

The Pharmacokinetic Study of bupivacaine pamoate After a Single Subcutaneously Injection in Rabbit Hernia Models Normal rabbits and hernia surgery model rabbits were administrated with bupivacaine pamoate (Formulation Examples 8 and 9) respectively. In comparison with the hernia model surgery model rabbits injected with the commercial bupivacaine hydrochloride injection, the differences regarding the systemic absorption and exposure of bupivacaine in the hernia surgery model animals injected with bupivacaine pamoate were evaluated, and the differences regarding the absorption and exposure of bupivacaine between normal and the hernia surgery model rabbits after bupivacaine pamoate administration were also investigated The long-acting sustained release feature of bupivacaine pamoate was verified by comparing the pharmacokinetic parameters of bupivacaine pamoate formulation with the commercial formulation.

16 healthy New Zealand white rabbits (Yizheng Anlimao Biological Technology Co., Ltd., 2.5 to 3.5 kg) were chosen and divided into 4 groups, i.e., three groups for Formulation Examples and one group for the commercial bupivacaine hydrochloride injection (Wuhu Kangqi Pharmaceutical Co., Ltd.), with 4 animals in each group, half male and half female. Detailed administration regimen is as shown in the table below:

The administration regimen for pharmacokinetic comparison research on rabbits which are subcutaneously injected with bupivacaine pamoate

| Group | Drug | Method and frequency of administration | Dosage (mg/kg) | Number of Animal |
|---|---|---|---|---|
| Group 1 | Postsurgical Formulation Example 8 group (suspension) | Subcutaneous injection (single) | 10 | 4 |
| Group 2 | Postsurgical Formulation Example 9 group (suspension) | Subcutaneous injection (single) | 30 | 4 |
| Group 3 | Non-operative Formulation Example 9 group (suspension) | Subcutaneous injection (single) | 30 | 4 |
| Group 4 | Postoperative bupivacaine hydrochloride injection | Subcutaneous injection (single) | 10 | 4 |

About 0.3 mL of venous blood was collected at 1 h, 2 h, 4 h, 8 h, 24 h, 48 h, 72 h and 96 h, respectively, after drug administration from all experimental animals for determining the blood drug concentration of bupivacaine.

The blood drug concentration-time curve and pharmacokinetic parameters are shown in the table below. In comparison with the commercial formulation group (10 mg/kg), the $C_{max}$ value of triple dosages of the groups for Formulation Examples (30 mg/kg) was only up to about 15.85% of that of the group for commercial formulation, while the half life was as long as 98 hours, more than 16 times longer than that of the group for commercial formulation. The AUC of Group 1 for Example was about 106% of that of the commercial formulation, and the AUCs of Group 2 and Group 3 for high concentration formulation Examples were about 55% and 50% of that of the commercial formulation, respectively. The average blood drug concentration of the groups for Formulation Examples (suspension) was more than that of the group for bupivacaine hydrochloride at 8 hours after administration. The blood drug concentration of the low dosage group even at 72 hours after administration was still close to that of the group for bupivacaine hydrochloride at the time point of 8 hours, and the blood drug concentration of the high dosage group even at 96 hours after administration was still about 2 times greater than that of the group for bupivacaine hydrochloride at the time point of 8 hours.

The above research results indicated that the solid suspension formulation of bupivacaine pamoate has a good sustained-release pharmacokinetic feature, maintaining an active drug concentration for 96 hours or longer, and thus has a good prospect of being developed to a long-acting sustained release and local postsurgical analgesic; and the plasma bupivacaine exposure in postsurgical animals were not significantly increased than those in non-surgery animals, which ensures the safety of postsurgical administration effectively.

TABLE

Time-dependent drug concentration data of pharmacokinetic comparison research on rabbits which are subcutaneously injected with a bupivacaine pamoate suspension

| Time h | Group 1 Blood drug level | Group 2 | Group 3 | Group 4 |
|---|---|---|---|---|
| 0 | 0.0 | 0.0 | 0.0 | 0.0 |
| 1 | 97.8 | 91.4 | 55.5 | 757.4 |
| 2 | 99.5 | 89.8 | 83.0 | 516.0 |
| 4 | 97.0 | 92.4 | 96.4 | 303.8 |
| 8 | 92.7 | 93.5 | 99.9 | 169.6 |
| 24 | 76.6 | 108.5 | 88.0 | 26.2 |
| 48 | 42.0 | 69.5 | 67.4 | 2.8 |
| 72 | 23.1 | 64.4 | 54.6 | |
| 96 | 14.1 | 47.0 | 45.4 | |
| Pharmacokinetic parameter | | | | |
| $AUC_{0-t}$ (ng/mL*h) | 4730 | 7386 | 6692 | 4442 |
| $C_{max}$ (ng/mL) | 109 | 120 | 104 | 757 |
| $T_{max}$ (h) | 9 | 18 | 6 | 1 |
| $T_{1/2}$ (h) | 34 | 72 | 98 | 6 |

Test Example 8

Local Anesthetic Efficacy Study of Intradermal Administrations of Bupivacaine Pamoate Formulation in Guinea pigs The local anesthetic and analgesic effects of bupivacaine pamoate on the injection site and the intensity were investigated by intradermally injecting bupivacaine pamoate to Hartley-based Guinea pigs. The long-acting local analgesic effect of bupivacaine pamoate was verified by comparing it with the commercial bupivacaine hydrochloride injection.

In this example, 6 healthy Guinea pigs (Qinglong Mountain Breeding Ground, Jiangning District, Nanjing) were chosen and divided into 3 groups, i.e., low concentration group of bupivacaine pamoate (Formulation Examples 8), high concentration group of bupivacaine pamoate (Formulation Examples 9), and commercial formulation group (bupivacaine hydrochloride injection, Shanghai Zhaohui Pharmaceutical Co., Ltd.), with 2 in each group. Detailed administration regimen is shown in the table below:

TABLE 1

Dosage information for each group and animal group information

| Group | Sample | Concentration (mg/mL) | Dose volume (mL/individual) | Number of Animal (n) |
|---|---|---|---|---|
| 1 (low concentration group) | Formulation Example 8 | 10 | 0.4 | 2 |
| 2 (high concentration group) | Formulation Example 9 | 30 | 0.4 | 2 |
| 3 (commercial formulation control group) | Bupivacaine hydrochloride injection | 5 | 0.4 | 2 |

Before administration, the skin in the middle ⅓ region of the back on the left side of the animal vertebral column was depilated, and the corresponding drug was intracutaneously injected with a 5 gauge needle in the depilated region (close injection sites were chosen at different positions as far as possible). The papule after injection was made round as far as possible. At 0.5, 3, 6, 12, 24, and 48 h after administration, the administration papule region of the Guinea pig was acupunctured with a 3 gauge needle (the acupuncture sites of different animals were made close as far as possible). The acupuncture was performed 9 times for each test. A pain response was recorded when the skin of the Guinea pig contracted or the Guinea pig brayed, or otherwise a painless response was recorded. The total painless response number was recorded to calculate the index of the painless response occurring rate for subsequent comparison of the analgesic effects.

Figure 15:
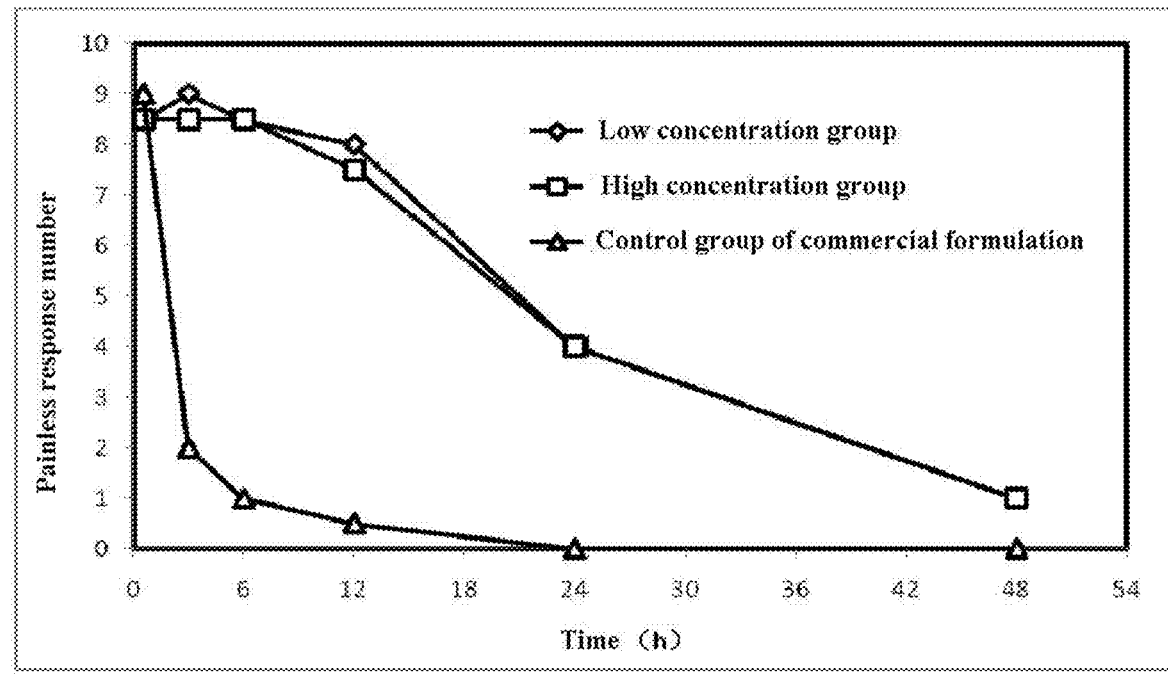
FIG. 15 shows a comparison diagram of the efficacy of Test Example 8.

The painless response number-time curves for the low and high concentration groups for bupivacaine pamoate and the group for bupivacaine hydrochloride for injection are shown in FIG. 15. At 0.5 h after administration, the painless response occurring rates of the low concentration group (10 mg/mL) and high concentration group (30 mg/mL) for bupivacaine pamoate and the group for bupivacaine hydrochloride injection (5 mg/mL) were comparable, between 8 and 9 times (a painless response occurring rate of 89%~100%); At 12 h after administration, the painless response number of the low concentration group and high concentration group for bupivacaine pamoate were between 7.5 and 9 times (a painless response occurring rate of 83%~100%); and at 24 h after administration, all the painless response numbers were maintained 4 times (a painless response occurring rate of 44%); and at 48 h after administration, the painless response numbers were maintained once (a painless response occurring rate of 11%); The painless response numbers of the group for bupivacaine hydrochloride injection reduced to once (a painless response occurring rate of 11%) at 6 h after administration.

The above research results indicated that bupivacaine pamoate had a potentially long-acting local analgesic effect, and the local analgesic efficacy could be maintained for up to 48 hours.

The preferred embodiments of the present invention are described in detail above with reference to the drawings. However, the present invention is not limited to the particular details of the above embodiments. Various simple variations can be made to the technical solutions of the present invention within the technical concept of the present invention, and all these simple variations fall within the protection scope of the present invention.

Further, it should be noted that various particular technical features described in the above particular embodiments can be combined in any suitable manner without contradiction. In order to avoid unnecessary repetition, various possible combinations are not further described in the present invention.

In addition, various different embodiments of the present invention can also be combined in any manner, as long as they do not depart from the spirit of the present invention, and the combinations should also be regarded as being within the present invention.

What is claimed is:

1. A complex of formula (I) or a solvate thereof:

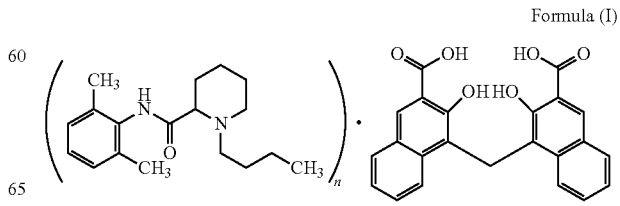

Formula (I)

wherein n is 2.

2. The complex or the solvate thereof according to claim 1, wherein the solvate is a methanol solvate, an ethanol solvate, or a hydrate.

3. The complex or the solvate thereof according to claim 1, wherein the complex or the solvate is an ethanol solvate having a polymorph A, wherein the X-ray powder diffraction pattern thereof, measured with Cu-Kα radiation, has diffraction peaks at about 4.9±0.2, 9.8±0.2, and 12.0±0.2 represented by 2θ.

4. The complex or the solvate thereof according to claim 3, wherein the X-ray powder diffraction pattern of the polymorph A, measured with Cu-Kα radiation, further comprises diffraction peaks at about 10.9±0.2, 12.9±0.2, 13.7±0.2, 14.7±0.2, 15.6±0.2, 16.3±0.2, 17.6±0.2, 18.9±0.2, 19.7±0.2, 20.2±0.2, 24.7±0.2, and 26.1±0.2 represented by 2θ.

5. The complex or the solvate thereof according to claim 1, wherein the complex or the solvate thereof is a methanol solvate having a polymorph B, wherein the X-ray powder diffraction pattern thereof, measured with Cu-Kα radiation, has diffraction peaks at about 10.9±0.2, 12.6±0.2, and 13.7±0.2 represented by 2θ.

6. The complex or the solvate thereof according to claim 5, wherein the X-ray powder diffraction pattern of the polymorph B, measured with Cu-Kα radiation, further comprises diffraction peaks at about 14.2±0.2, 15.7±0.2, 16.7±0.2, 17.3±0.2, 18.3±0.2, 18.9±0.2, 19.4±0.2, 25.1±0.2, 26.4±0.2, 29.0±0.2, and 34.6±0.2 represented by 2θ.

7. The complex or the solvate thereof according to claim 1, wherein the complex or the solvate thereof is a hydrate having a polymorph C, wherein the X-ray powder diffraction pattern thereof, measured with Cu-Kα radiation, has diffraction peaks at about 10.8±0.2, 12.6±0.2, and 13.7±0.2 represented by 2θ.

8. The complex or the solvate thereof according to claim 7, wherein the X-ray powder diffraction pattern of the polymorph C, measured with Cu-Kα radiation, further comprises diffraction peaks at about 16.5±0.2, 18.2±0.2, 19.4±0.2, 20.0±0.2, and 27.0±0.2 represented by 2θ.

9. The complex or the solvate thereof according to claim 1, wherein the complex or the solvate thereof is in an amorphous form.

10. The complex or the solvate thereof according to claim 1, wherein the complex or the solvate thereof has a median particle size $D_{50}$ in a range of 0.1 to 50 μm.

11. A method for preparing the complex or the solvate thereof according to claim 1, comprising mixing bupivacaine and pamoic acid in a molar ratio of greater than 1:1 and less than or equal to 4:1 in a solvent and heating the resultant mixture, wherein the solvent is selected from the group consisting of methanol, acetone, ethanol, dimethylsulfoxide, N,N-dimethylformamide, water and a mixed solvent thereof.

12. The method according to claim 11, wherein the molar ratio between the bupivacaine and the pamoic acid is greater than or equal to 2:1.

13. A method for preparing the complex or the solvate thereof according to claim 3, comprising mixing bupivacaine and pamoic acid in a molar ratio of greater than or equal to 2:1 in a solvent and heating the resultant mixture, wherein the solvent comprises ethanol and optionally comprises one or more selected from the group consisting of methanol, acetone, dimethylsulfoxide, N,N-dimethylformamide and water.

14. A method for preparing the complex or the solvate thereof according to claim 5, comprising mixing bupivacaine and pamoic acid in a molar ratio of greater than or equal to 2:1 in a solvent and heating the resultant mixture, wherein the solvent comprises methanol and optionally comprises one or more selected from the group consisting of acetone, dimethylsulfoxide, N,N-dimethylformamide and water.

15. A method for preparing the complex or the solvate thereof according to claim 7, comprising converting the complex of formula (I) or the solvate thereof into a bis (bupivacaine) pamoate hydrate in water,
wherein
the complex or the solvate is an ethanol solvate having a polymorph A wherein the X-ray powder diffraction pattern thereof, measured with Cu-Kα radiation, has diffraction peaks at about 4.9±0.2, 9.8±0.2, and 12.0±0.2 represented by 2θ, or
the complex or the solvate thereof is a methanol solvate having a polymorph B, wherein the X-ray powder diffraction pattern thereof, measured with Cu-Kα radiation, has diffraction peaks at about 10.9±0.2, 12.6±0.2, and 13.7±0.2 represented by 2θ, or
the complex or the solvate thereof is in an amorphous form.

16. A method for preparing the complex according to claim 9, comprising converting the complex of formula (I) or the solvate thereof into amorphous powders by heating it to remove the solvent; or preparing amorphous powders from bupivacaine and pamoic acid by a melting method,
wherein
the complex or the solvate is an ethanol solvate having a polymorph A, wherein the X-ray powder diffraction pattern thereof, measured with Cu-Kα radiation, has diffraction peaks at about 4.9±0.2, 9.8±0.2, and 12.0±0.2 represented by 2θ, or
the complex or the solvate thereof is a methanol solvate having a polymorph B, wherein the X-ray powder diffraction pattern thereof, measured with Cu-Kα radiation, has diffraction peaks at about 10.9±0.2, 12.6±0.2, and 13.7±0.2 represented by 2θ, or
the complex or the solvate thereof is a hydrate having a polymorph C, wherein the X-ray powder diffraction pattern thereof, measured with Cu-Kα radiation, has diffraction peaks at about 10.8±0.2, 12.6±0.2, and 13.7±0.2 represented by 2θ.

17. A pharmaceutical composition comprising a pharmaceutically effective amount of the complex or the solvate thereof according to claim 1 and a pharmaceutically acceptable excipient.

18. The pharmaceutical composition according to claim 17, wherein the pharmaceutical composition is a suspension, and comprises 1 to 300 mg of the complex or the solvate thereof per 1 mL of the suspension.

19. A method for the prevention or treatment of surgical pain, intraoperative pain, and postsurgical pain, comprising administering to a patient in need thereof the pharmaceutical composition of claim 17, wherein the pharmaceutical composition is administered via subcutaneous injection, intracutaneous injection, or intramuscular injection.

20. The pharmaceutical composition according to claim 17, wherein the pharmaceutically acceptable excipient comprises one or more selected from the group consisting of a suspending agent, a surfactant, a filler, a preservative, an isoosmotic adjusting agent, a pH modifier, a buffer and water.

21. The pharmaceutical composition according to claim 17, wherein the complex or the solvate thereof is solid particles having a median particle size $D_{50}$ in a range of 0.2 to 20 µm.

22. The pharmaceutical composition according to claim 17, wherein the pharmaceutical composition comprises no water, and comprises 10 wt % or more of the complex or the solvate thereof.

23. The pharmaceutical composition according to claim 20, wherein the suspending agent is one or more selected from the group consisting of carboxymethyl cellulose or a sodium salt thereof, hydroxypropyl cellulose, methyl cellulose, hydroxyethyl cellulose, hydroxypropyl methylcellulose, sodium hyaluronate, and polyvinylpyrrolidone; the surfactant is one or more selected from the group consisting of polysorbate-20, polysorbate-40, polysorbate-60, polysorbate-65, polysorbate-80, polysorbate-85, polyoxyethylated castor oil, polyoxyethylated hydrogenated castor oil, lecithin, polyvinylpyrrolidone, polyethylene glycols, polyethylene oxide and polypropylene oxide ethers, and polyethylene glycol 15-hydroxystearate; the filler is one or more selected from the group consisting of mannitol, sucrose, maltose, xylitol, lactose, glucose, starch and sorbitol; the preservative is one or more selected from the group consisting of benzoic acid, benzyl alcohol, butylated hydroxytoluene ether, butylated hydroxytoluene, chlorobutanol, gallate, hydroxybenzoate, ethylenediamine tetraacetic acid and a salt thereof, chlorocresol, m-cresol, methylbenzethonium chloride, myristyl-γ-methylpyridine chloride, phenylmercuric acetate, and thimerosal; the isoosmotic adjusting agent is one or more selected from the group consisting of mannitol, sorbitol, sodium chloride, glucose, sucrose, fructose, and lactose; and the buffer is one or more selected from the group consisting of a phosphate, an acetate, a citrate, and a tris(hydroxymethyl)aminomethane buffer solution.

* * * * *

UNITED STATES PATENT AND TRADEMARK OFFICE
CERTIFICATE OF CORRECTION

PATENT NO. : 11,084,790 B2
APPLICATION NO. : 16/325997
DATED : August 10, 2021
INVENTOR(S) : Zhang et al.

Page 1 of 1

It is certified that error appears in the above-identified patent and that said Letters Patent is hereby corrected as shown below:

In the Claims

In Column 46, Claim 15, Line 17, delete "20," and insert -- 2θ, --, therefor.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*